United States Patent
Yu et al.

(10) Patent No.: US 12,194,322 B2
(45) Date of Patent: *Jan. 14, 2025

(54) WEARABLE DEVICE FOR DELIVERING AIR

(71) Applicant: ResMed Pty Ltd, Bella Vista (AU)

(72) Inventors: Tzu-Chin Yu, Sydney (AU); Emma Anne Connell, Sydney (AU); David Creusot, Sydney (AU); Donald Darkin, Dural (AU); Barton John Kenyon, Sydney (AU); Paul Jan Klasek, Bonnyrigg Heights (AU); Andrew Sims, Sydney (AU); Quangang Yang, Sydney (AU); Phillip Rodney Kwok, Chatswood (AU)

(73) Assignee: ResMed Pty Ltd (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/315,586

(22) Filed: May 11, 2023

(65) Prior Publication Data
US 2023/0405368 A1    Dec. 21, 2023

Related U.S. Application Data

(63) Continuation of application No. 15/529,653, filed as application No. PCT/AU2015/050766 on Dec. 4, 2015, now Pat. No. 11,679,287.
(Continued)

(51) Int. Cl.
*A61M 16/00*    (2006.01)
*A41B 1/00*    (2006.01)
(Continued)

(52) U.S. Cl.
CPC .............. *A62B 18/003* (2013.01); *A41B 1/00* (2013.01); *A41B 3/00* (2013.01); *A41D 20/00* (2013.01);
(Continued)

(58) Field of Classification Search
CPC ....... A62B 9/06; A62B 18/003; A62B 18/006; A63B 71/085; A63F 13/28; A63F 13/30;
(Continued)

(56) References Cited

U.S. PATENT DOCUMENTS

| 968,232 A | 8/1910 | Bentz |
| 1,646,103 A | 10/1927 | Patrick |

(Continued)

FOREIGN PATENT DOCUMENTS

| CN | 2724758 Y | 9/2005 |
| CN | 101365532 A | 2/2009 |

(Continued)

OTHER PUBLICATIONS

Office Action issued in corresponding Japanese Patent Application No. 2022-112135, mailed Jun. 6, 2023, 6 pages.
(Continued)

*Primary Examiner* — Colin W Stuart
*Assistant Examiner* — Matthew D Ziegler
(74) *Attorney, Agent, or Firm* — Botos Churchill IP Law LLP

(57) ABSTRACT

A personal entertainment respiratory apparatus provides air to a user to provide a fully immersive entertainment experience. The personal entertainment system may comprise a flow generator for providing the flow of air. A personal spatial respiratory interface may be coupled to the flow generator. The personal spatial respiratory interface may comprise an outlet for the flow generator. The personal spatial respiratory interface may further be configured to direct the flow of air within an ambient breathing proximity of a user. The personal entertainment respiratory apparatus may further comprise a controller and a sensory particle dispenser. The controller and sensory particle dispenser may be configured to selectively activate release of a sensory (Continued)

particle from the dispenser into the directed flow of air in response to an entertainment triggering signal.

18 Claims, 40 Drawing Sheets

Related U.S. Application Data

(60) Provisional application No. 62/087,500, filed on Dec. 4, 2014.

(51) Int. Cl.

| | |
|---|---|
| A41B 3/00 | (2006.01) |
| A41D 20/00 | (2006.01) |
| A41D 23/00 | (2006.01) |
| A42B 1/006 | (2021.01) |
| A44C 5/00 | (2006.01) |
| A61F 9/02 | (2006.01) |
| A61F 9/04 | (2006.01) |
| A61M 16/06 | (2006.01) |
| A61M 16/08 | (2006.01) |
| A61M 16/10 | (2006.01) |
| A61M 16/16 | (2006.01) |
| A61M 21/00 | (2006.01) |
| A62B 9/06 | (2006.01) |
| A62B 18/00 | (2006.01) |
| A63B 71/08 | (2006.01) |
| A63F 13/28 | (2014.01) |
| A63F 13/30 | (2014.01) |
| F04D 19/00 | (2006.01) |
| F04D 25/08 | (2006.01) |
| F04D 17/02 | (2006.01) |
| F04D 25/06 | (2006.01) |

(52) U.S. Cl.
CPC .............. *A41D 23/00* (2013.01); *A42B 1/006* (2013.01); *A44C 5/0023* (2013.01); *A61F 9/028* (2013.01); *A61F 9/045* (2013.01); *A61M 16/0066* (2013.01); *A61M 16/0069* (2014.02); *A61M 16/0672* (2014.02); *A61M 16/0875* (2013.01); *A61M 16/1055* (2013.01); *A61M 16/107* (2014.02); *A61M 16/1075* (2013.01); *A61M 16/16* (2013.01); *A61M 21/00* (2013.01); *A62B 9/06* (2013.01); *A62B 18/006* (2013.01); *A63B 71/085* (2013.01); *A63F 13/28* (2014.09); *A63F 13/30* (2014.09); *F04D 19/007* (2013.01); *F04D 25/084* (2013.01); *A61M 2016/0039* (2013.01); *A61M 16/1065* (2014.02); *A61M 16/161* (2014.02); *A61M 2021/0016* (2013.01); *A61M 2205/3561* (2013.01); *A61M 2205/3592* (2013.01); *A61M 2205/581* (2013.01); *A61M 2205/583* (2013.01); *A61M 2205/8206* (2013.01); *A61M 2209/088* (2013.01); *A61M 2230/06* (2013.01); *A61M 2230/205* (2013.01); *A61M 2230/42* (2013.01); *A61M 2230/50* (2013.01); *F04D 17/025* (2013.01); *F04D 25/0673* (2013.01)

(58) Field of Classification Search
CPC .. F04D 17/025; F04D 19/007; F04D 25/0673; F04D 25/084; A41B 1/00; A41B 3/00; A41D 20/00; A41D 23/00; A42B 1/006; A44C 5/0023; A61F 9/028; A61F 9/045; A61M 16/00; A61M 16/0003; A61M 16/0057; A61M 16/0063; A61M 16/0066; A61M 16/0069; A61M 16/0672; A61M 16/0875; A61M 16/022; A61M 16/105–107; A61M 16/1075; A61M 16/12–127; A61M 16/16; A61M 16/161; A61M 16/18; A61M 21/00; A61M 2016/0039; A61M 2021/0016; A61M 2205/11; A61M 2205/13; A61M 2205/33; A61M 2205/3303; A61M 2205/3327; A61M 2205/3331; A61M 2205/35; A61M 2205/3561; A61M 2205/3592; A61M 2205/583; A61M 2205/75–759; A61M 2205/8206; A61M 2209/088; A61M 2230/06; A61M 2230/205; A61M 2230/42; A61M 2230/50

See application file for complete search history.

(56) References Cited

U.S. PATENT DOCUMENTS

| | | | |
|---|---|---|---|
| 2,032,101 A | 2/1936 | Sullivan | |
| 2,402,820 A | 6/1946 | Kitchen | |
| 2,469,273 A | 5/1949 | Parker | |
| 2,507,705 A | 5/1950 | Gaddini | |
| 2,560,215 A | 7/1951 | Marinus | |
| 3,168,748 A | 2/1965 | Wayne | |
| 3,291,027 A | 12/1966 | Sterling | |
| 3,566,409 A | 3/1971 | Hopper | |
| 3,649,964 A | 3/1972 | Schoelz et al. | |
| 3,683,907 A | 8/1972 | Cotabish | |
| 3,724,172 A | 4/1973 | Wood | |
| 3,735,423 A | 5/1973 | Droz | |
| 3,804,592 A | 4/1974 | Garbe | |
| 3,813,696 A | 6/1974 | Yeager | |
| 3,881,198 A | 5/1975 | Waters | |
| 3,881,478 A | 5/1975 | Rosendahl et al. | |
| 3,963,021 A | 6/1976 | Bancroft | |
| 4,057,058 A | 11/1977 | Kovacevic | |
| 4,141,083 A | 2/1979 | Waters | |
| 4,195,363 A | 4/1980 | Jenson | |
| 4,267,831 A * | 5/1981 | Aguilar | A62B 23/06 |
| | | | 128/203.14 |
| 4,546,496 A | 10/1985 | Lewis | |
| 4,590,951 A | 5/1986 | O'Connor | |
| 4,680,815 A | 7/1987 | Hirsch et al. | |
| 4,752,974 A | 6/1988 | Haino | |
| 4,846,152 A | 7/1989 | Wampler et al. | |
| 4,893,356 A | 1/1990 | Waters | |
| 4,971,052 A | 11/1990 | Edwards | |
| 5,085,231 A | 2/1992 | Johnson | |
| 5,123,114 A | 6/1992 | Desanti | |
| 5,283,914 A | 2/1994 | James | |
| 5,304,035 A | 4/1994 | Carter | |
| 5,353,605 A | 10/1994 | Naaman | |
| 5,484,472 A | 1/1996 | Weinberg et al. | |
| 5,561,862 A | 10/1996 | Flores | |
| 5,577,494 A * | 11/1996 | Kuypers | D04H 1/54 |
| | | | 128/205.12 |
| 5,577,495 A | 11/1996 | Murphy | |
| 5,591,409 A | 1/1997 | Watkins | |
| 5,610,674 A | 3/1997 | Martin | |
| 5,724,256 A | 3/1998 | Lee et al. | |
| 5,878,742 A | 3/1999 | Figueredo et al. | |
| 5,949,522 A * | 9/1999 | Manne | A61L 9/122 |
| | | | 261/DIG. 65 |
| 6,032,291 A | 3/2000 | Asenguah et al. | |
| 6,065,473 A | 5/2000 | McCombs et al. | |
| 6,119,689 A | 9/2000 | Korman | |
| 6,192,702 B1 | 2/2001 | Shimogori | |
| 6,223,744 B1 | 5/2001 | Garon | |
| 6,247,470 B1 | 6/2001 | Ketchedjian | |
| 6,370,695 B2 | 4/2002 | Paris et al. | |
| 6,371,451 B1 | 4/2002 | Choi | |
| 6,390,453 B1 | 5/2002 | Frederickson et al. | |
| 6,409,338 B1 | 6/2002 | Jewell | |
| 6,412,173 B1 | 7/2002 | Johnson et al. | |
| 6,468,030 B2 | 10/2002 | Kawasaki | |
| 6,554,203 B2 | 4/2003 | Hess et al. | |

(56) References Cited

U.S. PATENT DOCUMENTS

| | | |
|---|---|---|
| 6,619,911 B1 | 9/2003 | Englaender et al. |
| 6,666,647 B1 | 12/2003 | Trask |
| 6,672,827 B2 | 1/2004 | Yamashita et al. |
| 6,772,762 B2 | 8/2004 | Piesinger |
| 6,836,906 B2 | 1/2005 | Holmes |
| 6,993,930 B2 | 2/2006 | Blackstone |
| 7,036,502 B2 | 5/2006 | Manne |
| 7,036,927 B2 | 5/2006 | Kopfer |
| 7,037,188 B2 | 5/2006 | Schmid et al. |
| 7,052,509 B2 | 5/2006 | Lennox et al. |
| 7,154,579 B2 | 12/2006 | Selander et al. |
| 7,331,064 B1 | 2/2008 | Quintal |
| 7,387,265 B2 | 6/2008 | Hess et al. |
| 7,484,716 B2 | 2/2009 | Ford et al. |
| 7,686,869 B2 | 3/2010 | Wiser et al. |
| 7,694,680 B2 | 4/2010 | Brichetto |
| 7,828,524 B2 | 11/2010 | Chen |
| 7,866,944 B2 | 1/2011 | Kenyon et al. |
| 7,921,473 B1 | 4/2011 | Winters |
| 8,029,237 B2 | 10/2011 | Chang et al. |
| 8,087,907 B2 | 1/2012 | Kawasaki et al. |
| 8,172,515 B2 | 5/2012 | Kawashima et al. |
| 8,295,529 B2 | 10/2012 | Petersen et al. |
| 8,327,846 B2 | 12/2012 | Bowditch et al. |
| 8,448,739 B2 | 5/2013 | Kolich |
| 8,636,479 B2 | 1/2014 | Kenyon et al. |
| 8,733,356 B1 | 5/2014 | Roth |
| 2001/0050079 A1 | 12/2001 | Piesinger |
| 2003/0188743 A1 | 10/2003 | Manne |
| 2003/0192959 A1 | 10/2003 | Hess et al. |
| 2004/0055601 A1 | 3/2004 | De et al. |
| 2004/0211422 A1* | 10/2004 | Arcilla .............. A61M 16/20 128/204.19 |
| 2005/0061316 A1 | 3/2005 | Manne |
| 2005/0130747 A1 | 6/2005 | Kubby et al. |
| 2005/0284470 A1 | 12/2005 | Wei et al. |
| 2006/0065986 A1 | 3/2006 | Morie et al. |
| 2006/0237013 A1 | 10/2006 | Kwok |
| 2007/0286720 A1 | 12/2007 | Chang et al. |
| 2008/0307970 A1 | 12/2008 | Augustine et al. |
| 2009/0000618 A1 | 1/2009 | Warren |
| 2009/0194101 A1 | 8/2009 | Kenyon et al. |
| 2009/0246013 A1 | 10/2009 | Kenyon et al. |
| 2010/0309434 A1 | 12/2010 | Van et al. |
| 2011/0118026 A1 | 5/2011 | Lukas et al. |
| 2011/0240011 A1 | 10/2011 | Caldwell |
| 2012/0199124 A1 | 8/2012 | Bowditch et al. |
| 2012/0294876 A1 | 11/2012 | Zimmerman |
| 2013/0112195 A1 | 5/2013 | Smith |
| 2013/0118506 A1 | 5/2013 | Osipov et al. |
| 2013/0296812 A1 | 11/2013 | Bangera et al. |
| 2013/0306060 A1 | 11/2013 | Cota et al. |
| 2013/0316635 A1 | 11/2013 | Sipila et al. |
| 2014/0069420 A1 | 3/2014 | Richter et al. |
| 2014/0069432 A1 | 3/2014 | Mebasser et al. |
| 2014/0193764 A1 | 7/2014 | Pizzini |
| 2015/0101600 A1 | 4/2015 | Miller et al. |
| 2016/0325068 A1 | 11/2016 | Truschel et al. |
| 2017/0113075 A1 | 4/2017 | Reiser et al. |

FOREIGN PATENT DOCUMENTS

| | | | |
|---|---|---|---|
| CN | 101951967 A | | 1/2011 |
| CN | 101975177 A | | 2/2011 |
| CN | 102811772 A | | 12/2012 |
| CN | 103949017 A | | 7/2014 |
| CN | 103961822 A | | 8/2014 |
| EP | 2740377 A2 | | 6/2014 |
| FR | 2109042 A5 | | 5/1972 |
| FR | 2663241 | * | 12/1991 |
| GB | 622486 A | | 5/1949 |
| GB | 2032284 A | | 5/1980 |
| GB | 2173705 A | | 10/1986 |
| GB | 2209474 A | | 5/1989 |
| GB | 2300814 A | | 11/1996 |
| GB | 2416489 A | | 2/2006 |
| JP | 863135651 U | | 9/1988 |
| JP | H08503622 A | | 4/1996 |
| JP | 2003164537 A | | 6/2003 |
| JP | 2003521651 A | | 7/2003 |
| JP | 2007301317 A | | 11/2007 |
| JP | 2008303876 A | | 12/2008 |
| JP | 2011523572 A | | 8/2011 |
| WO | 9324168 A1 | | 12/1993 |
| WO | 9614627 A1 | | 5/1996 |
| WO | 9806449 A1 | | 2/1998 |
| WO | 0143804 A1 | | 6/2001 |
| WO | 03037436 A1 | | 5/2003 |
| WO | 2009035545 A9 | | 5/2009 |
| WO | 2009109013 A1 | | 9/2009 |
| WO | 2013015432 A1 | | 1/2013 |
| WO | 2013020167 A1 | | 2/2013 |
| WO | 2013028148 A1 | | 2/2013 |
| WO | 2013160822 A1 | | 10/2013 |
| WO | 2013163208 A1 | | 10/2013 |
| WO | 2013181080 A1 | | 12/2013 |

OTHER PUBLICATIONS

Chinese Office Action issued in corresponding CN application No. 201580064966.4 on Apr. 3, 2019.
CN Notification of Grant dated Aug. 27, 2021 for Chinese Patent Application No. 2015800649664.
European search report from corresponding European Application No. 22189407.4-1122 dated Feb. 7, 2023.
Final Office Action mailed Jul. 10, 2020—U.S. Appl. No. 16/821,539.
First Office Action issued in corresponding Chinese Patent Application No. 2021113351010, mailed Nov. 3, 2022, 12 pages.
International Search Report for Application No. PCT/AU2015/050766 dated Feb. 24, 2016.
Japanese Office Action for Application No. P2021-014726 dated Jan. 5, 2022.
JP Office Action mailed Jan. 15, 2020 in Japanese Patent Application No. 2017-529300.
New Zealand Examination Report for Application No. 702750 dated Mar. 9, 2015.
Summons to attend oral proceedings issued in corresponding European Patent Application No. 15865965.6, mailed Feb. 6, 2024, 23 pages.
Office Action issued in corresponding Japanese Patent Application No. 2022-112135, mailed Feb. 27, 2024, 8 pages.
Merriam-Webster Dictionary Definition of Sensor Publication date (archived by the Wayback Machine): Sep. 5, 2008, downloaded from internet on Aug. 29, 2024, 1 page.
Submissions filed in response to the Summons to attend Oral Proceedings in corresponding European Patent Application No. 15865965.6, dated Aug. 14, 2024, 29 pages.
Sunon DC Brushless Blower GB0545AFV1-8 as cited by DI 5 Publication date (archived by the Wayback Machine): Jun. 6, 2013, 6 pages.

* cited by examiner

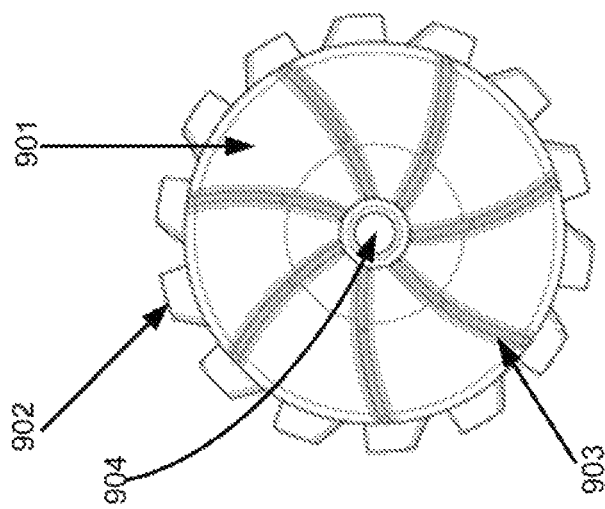
FIG. 9C
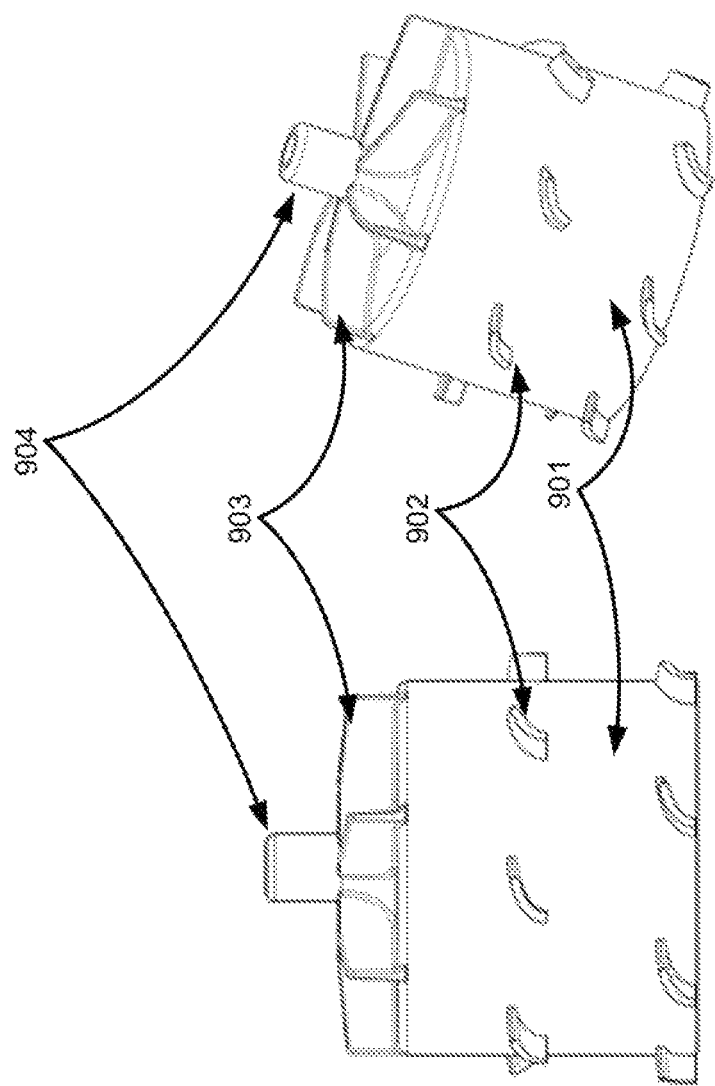
FIG. 9B
FIG. 9A

Air Nozzle Design

Saggital View

Air at 25 C Supply.Mass Fraction
Contour 1

WEARABLE DEVICE FOR DELIVERING AIR

CROSS REFERENCE TO RELATED APPLICATIONS

This application is a continuation of U.S. patent application Ser. No. 15/529,653, filed on May 25, 2017, which is a national phase entry under 35 U.S.C. § 371 of International Application No. PCT/AU2015/050766, filed Dec. 4, 2015, published in English, which claims priority from U.S. Provisional Patent Application No. 62/087,500 filed Dec. 4, 2014, all of which are incorporated herein by reference.

FIELD OF THE INVENTION

The present technology relates to one or more of respiratory influence such as for protection and/or for sensory stimulation. For example, the present technology may concern devices or apparatus, and their use in providing cleaned air. Also, the present technology relates to devices or apparatus, and their use in providing sensory stimulation.

BACKGROUND OF THE TECHNOLOGY

Air, whether indoors or outdoors, may include particles which can be harmful or undesirable to the human body. These particles are seldom visible and may be breathed in by an individual without knowledge that the particles were even present. These particles may come in the form of gas, scents, bacteria, allergens, and viruses, amongst others. Such particles can cause injury, create respiratory disorders, cause general discomfort, and even trigger allergic reactions. Certain occupations may place individuals within environments which contain more harmful particles than others. While all individuals may inadvertently breathe in harmful particles, workers within these occupations with higher exposure to harmful particles may be more susceptible to the negative effects the particles can cause.

BRIEF SUMMARY OF THE TECHNOLOGY

Some versions of the technology include an apparatus for providing cleaned air to a user. The apparatus may comprise a flow generator, the flow generator configured to generate a filtered flow of air. The apparatus may include a user flow interface (e.g. personal spatial respiratory interface) coupled to the flow generator. The personal spatial respiratory interface may comprise an outlet for the flow generator. The personal spatial respiratory interface may be configured to direct the flow of air within an ambient breathing proximity of a user.

In some cases, the apparatus may include an air inlet to the flow generator which includes a filter. The filter may be configured to remove particles from air drawn in through the inlet. The filter may be configured to remove volatile gas and odour from air drawn in through the inlet. The filter may further be configured to remove bacteria and virus from air drawn in through the inlet. The filter may be any one or more of a HEPA filter, an electret filter, an ionizer purifier, a thermodynamic sterilization filter, an activated carbon filter and a catalytic oxidation filter.

In some cases, the personal spatial respiratory interface may comprise a dispersed set of air outlets configured to produce the directed flow of air in an air curtain to separate the ambient breathing proximity of the user from uncleaned environmental air. The personal spatial respiratory interface may further comprise a set of air outlets configured to produce an air shield to separate the directed flow of air in the ambient breathing proximity of the user from uncleaned environmental air. The set of air outlets may comprise a laminarizing nozzle with a honey comb structure. Some versions of the personal spatial respiratory interface include an additional set of air outlets. The additional set of air outlets may produce one or more air curtains to separate the ambient breathing proximity of the user from uncleaned environmental air.

In some versions of the present technology, a personal spatial respiratory interface may comprise a fashion accessory such as a scarf, a shirt, a shirt collar, eye glasses, a visor, googles, a necklace, a hat, a headset, wristband, glove, etc. The personal spatial respiratory interface may comprise a plurality of outlets along a length of the user flow interface to direct the flow of air.

One form of the present technology comprises a personal spatial respiratory interface which provides air to a user without having facial contact. The personal spatial respiratory interface may provide air to a user without having head contact.

One form of the present technology comprises a flow generator which includes a pre-blower filter, blower and a post-blower filter. The blower may include a motor and an impeller. The flow generator may also include a multistage blower. The flow generator may be configured for battery operation. The flow generator may include a battery power source.

In some versions of the present technology, the apparatus may comprise a plurality of impellers in a parallel flow configuration or in a series flow configuration.

One form of the present technology comprises a controller and an aromatic dispenser. The controller may be configured to selectively activate release of an aromatic from the aromatic dispenser into a directed flow of air in response to an entertainment triggering signal. The controller may comprise a communications interface for receiving wirelessly, the entertainment triggering signal. The aromatic dispenser may be adapted to receive replaceable aromatic cartridges containing aromatics. The aromatic dispenser may be further configured to release different aromatics in response to different entertainment triggering signals. The aromatics may comprise smell and/or taste particles. The controller may be configured to generate an entertainment triggering signal for operation of an aromatic dispenser of the apparatus based on detected physiological data.

In some versions of the present technology, the apparatus may include a controller configured to set operation of one or more pollution filters of the apparatus. The apparatus may further and one or more air quality sensors coupled with the controller, the controller configured to set operation of the one or more pollution filters in response to a signal from the one or more air quality sensors.

In some versions of the present technology, the apparatus may comprise a controller. The controller may be configured with a location sensor to detect location of the apparatus and set operation of the one or more pollution filters of the apparatus based upon detection of the location. The controller may include a communications interface, and wherein the controller is configured to request and receive external weather or pollution data and set operation of the one or more pollution filters based on the received external weather or pollution data.

In some versions of the present technology, the apparatus may comprise a controller which may be self-configurable based on its detected environment. In this regard, the controller may be configured with one or more user sensors configured to detect physiological data of the user. The controller may be configured to set an operation of the apparatus based on a signal from the one or more sensors. The physiological data may include any one or more of heart rate data, perspiration data, temperature data, breath rate data, $O_2$ saturation data and the one or more user sensors comprises any one or more of a heart rate sensor, moisture sensor, thermistor, flow sensor, oximeter respectively. The controller may include a communications interface to communicate the physiological data to an entertainment console.

In some versions of the present technology a controller may be configured to control operation of the flow generator. The apparatus may further comprise a communications interface to send and receive data with an external programmable mobile processing device.

In some cases the apparatus comprises a droplet generator, wherein a controller of the apparatus in configured to control the droplet generator to inject droplets into the directed flow of air. The controller may inject the droplets in response to an entertainment signal. The apparatus may receive the entertainment signal from an external entertainment console. The droplets may be water.

In some cases the apparatus comprises at least one heating or cooling element, wherein a controller of the apparatus in configured to change a temperature of the directed flow of air by setting operation of the heating or cooling element. The apparatus changes the temperature in response to an entertainment signal. The apparatus of receives the entertainment signal from an external entertainment console.

In some cases the apparatus may include one or more sensors configured to detect orientation of the personal spatial respiratory interface/or to detect wind direction and wind speed, wherein a controller of the apparatus is configured to adjust operation of the apparatus based on a signal from the sensors. The one or more sensors may include an anemometer to detect wind and accelerometer to detect personal spatial respiratory interface orientation. The apparatus may include a controller configured to control a change in operation of the flow generator based on the detected wind and/or orientation of the personal spatial respiratory interface. The change in operation may comprise any one of a change in flow direction and a change in flow velocity. The apparatus may be configured to determine an optimal air nozzle orientation and/or air flow velocity as a function of detected oncoming wind.

Some versions of the technology include an apparatus for providing air to a user. The apparatus may include a flow generator. The flow generator may be configured to generate a flow of air. The apparatus may further include a personal spatial respiratory interface coupled to the flow generator, the personal spatial respiratory interface comprising an outlet for the flow generator, the personal spatial respiratory interface configured to direct the flow of air within an ambient breathing proximity of a user. The apparatus may further include a controller and sensory particle dispenser. The controller and sensory particle dispense may be configured to selectively activate release of a sensory particle from the dispenser into the directed flow of air in response to an entertainment triggering signal.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

FIG. 1 is a flowchart illustrating example clean air and entertainment systems in accordance with some aspects of the present technology.

FIG. 2 is an example of a blower suitable for the present technology.

FIG. 3A is an isometric example of a blower suitable for the present technology.

FIG. 3B is an example of a blower within a mixing chamber suitable for some embodiments of the present technology.

FIG. 4 is an example of a single-stage blower suitable for some embodiments of the present technology.

FIG. 5A is an example of a dual-stage blower suitable for some versions of the present technology.

FIG. 5B is an example of a three-stage blower suitable for some embodiments of the present technology.

FIG. 6 is an example of an axial blower suitable for some embodiments of the present technology.

FIGS. 7A, 7B, and 7C are examples of a multistage rotor and axial stages which may be formed from the multistage rotor suitable for some versions of the present technology.

FIG. 8A is a cross sectional view of a centrifugal multistage axial suitable for some embodiments of the present technology.

FIG. 8B is an example of a centrifugal multistage axial blower suitable for some embodiments of the present technology.

FIGS. 9A, 9B, and 9C are views of an example rotor compatible with a centrifugal multistage axial blower suitable for some versions of the present technology.

FIGS. 10A and 10B are views of an example outer housing for some versions of the present technology.

FIGS. 11A and 11B are views of example motor housing for some versions of the present technology.

FIG. 12 is an example of an air curtain system suitable for some embodiments the present technology.

FIG. 13 is a flowchart illustrating a system for delivering aromatics suitable for some versions of the present technology.

FIG. 14 is an example a schematic for a flow generator device suitable for some embodiments of the present technology.

FIG. 15 is an example schematic for a flow generator device with a sensory stimulant injection device suitable for some embodiments of the present technology.

FIG. 16 is an example of a user flow interface with glasses for delivery of air suitable for some versions of the present technology.

FIG. 17 is an illustration of a user flow interface including a headset for delivery of air suitable for some embodiments of the present technology.

FIG. 18 is an illustration of a delivery nozzle suitable for some embodiments of the present technology.

FIG. 19 is an illustration of a user flow interface including a headset for delivery and removal of air suitable for some versions of the present technology.

Figure 43B:
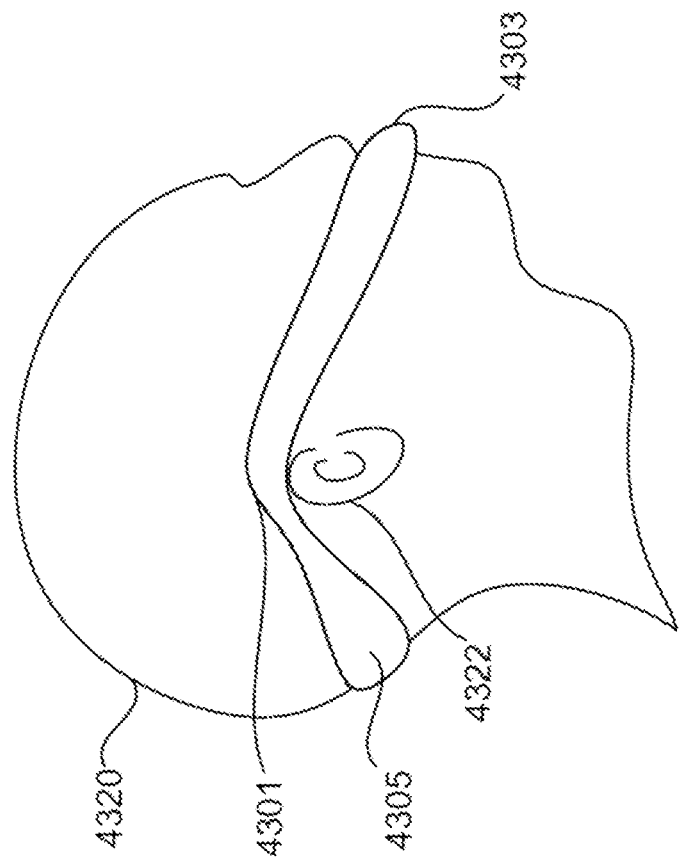
Figure 43A:
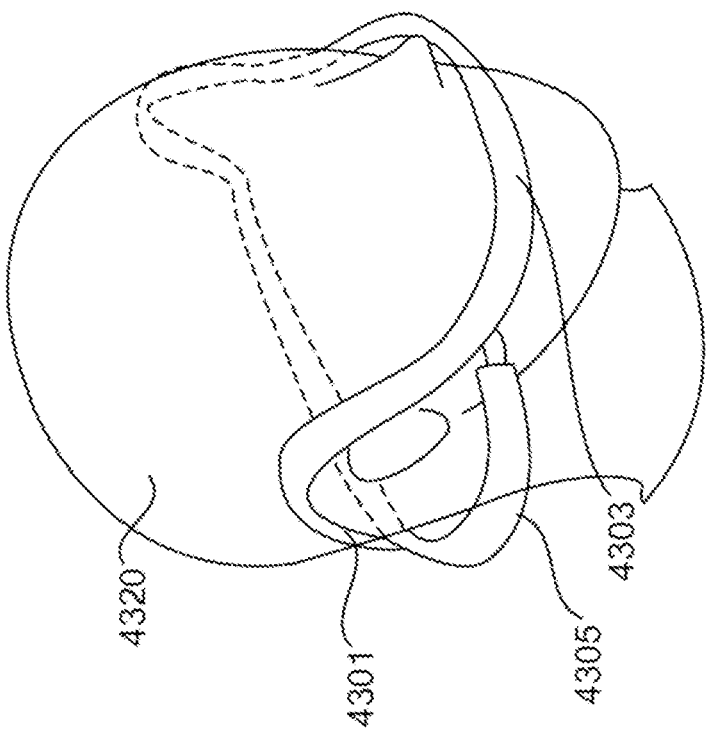

FIGS. 43A and 43B include an illustration of a user flow interface including a sports band suitable for some versions of the present technology.

Figure 44:
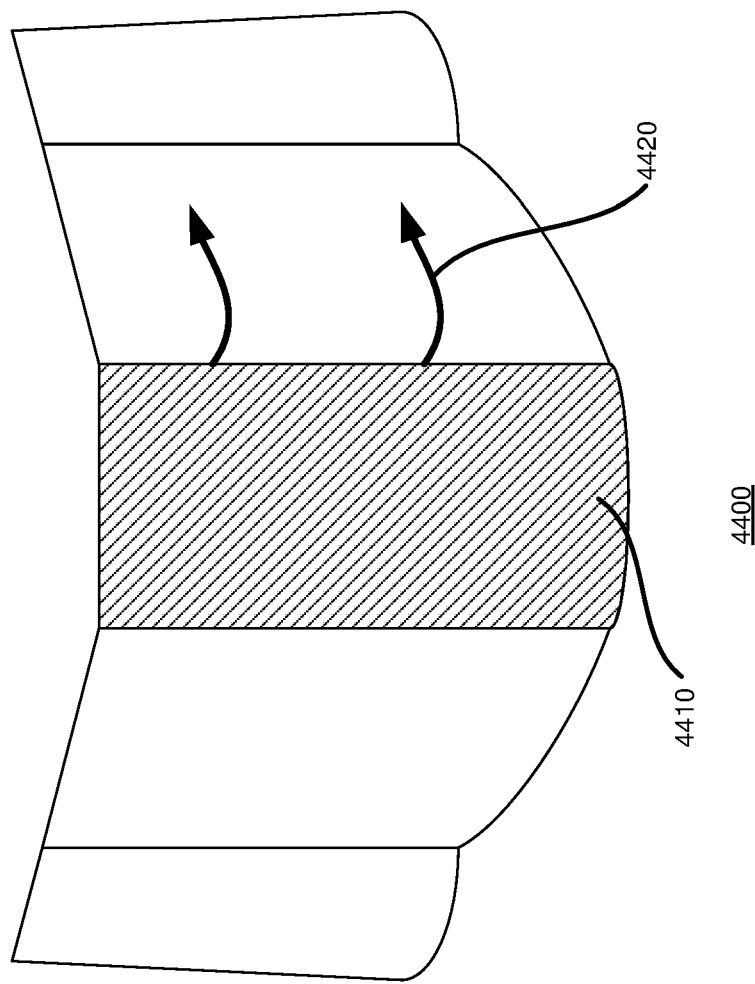

FIG. 44 is an illustration of a user flow interface including a sliding mask suitable for some versions of the present technology.

Figure 45:
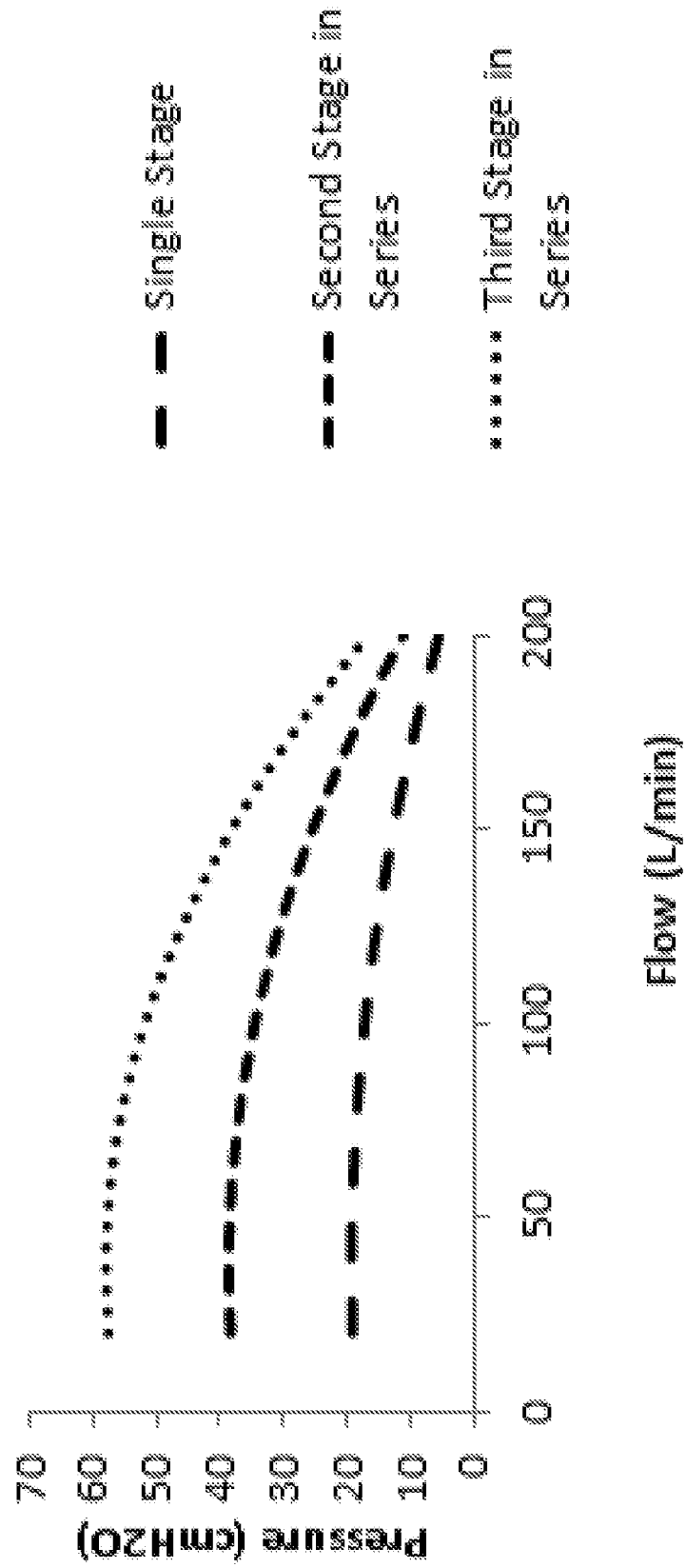

FIG. 45 is a table of an exemplary fan curve of a blower comprising one or more stages connected in series suitable for some versions of the present technology.

Figure 46:
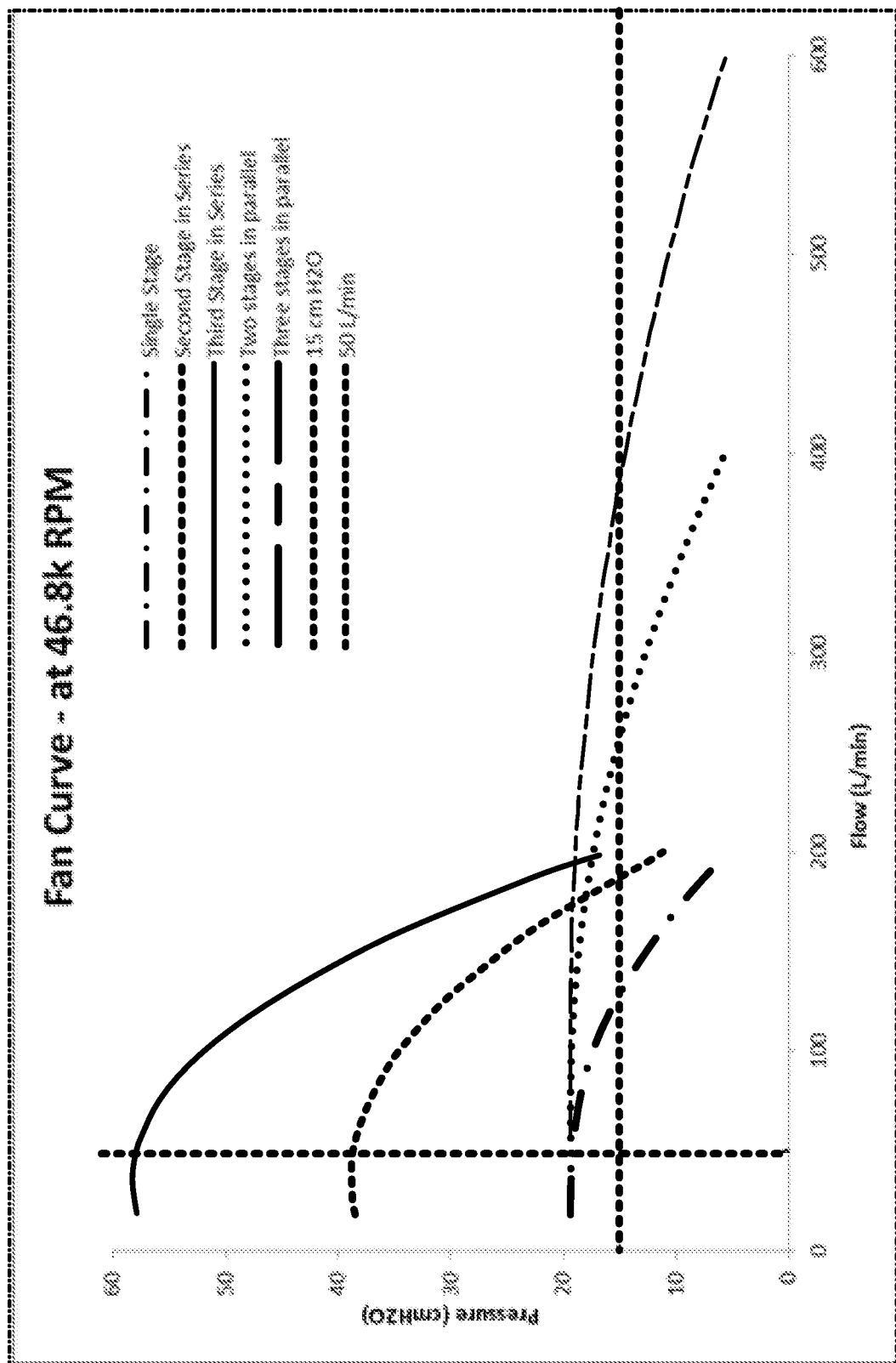

FIG. 46 is an exemplary fan curve of various blowers comprising one or more stages connected in series and/or parallel suitable for some versions of the present technology.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing the particular examples discussed herein, and is not intended to be limiting.

Overview

In one form, the present technology is directed to providing air, such as cleaned air, to a user. Depending on a user's needs, certain apparatuses may be used to provide a flow of cleaned air. For example, a clean air system (CAS) 101 in FIG. 1 may include a filter 103, and flow generator 1603 for supplying pressurized respiratory gas, such as air, to the user via an air delivery conduit 1604, such as a tube, leading to a user interface 104 which may output the air to the user.

In some cases the technology may be implemented to provide a more immersive "fourth dimensional" (4D) entertainment experience. Such a system may provide sensory experiences beyond the visual and auditory senses. For example, the system may provide entertainment through the stimulation of smell, touch, or taste. Further, the system may provide changes in humidity and temperature to the user. An example entertainment system 102 in FIG. 1 may include a flow generator 1603 connected to a filter 103 such as, for example, those implemented for a CAS 101. However, user flow interface 104 and the air flow generator 1603 may also be connected to a sensory monitoring and stimulation unit 105. The sensory monitoring and stimulation unit 105 may be implemented to adapt the air provided to the user flow interface 104 so as to manipulate the user's experience such as in conjunction with a form of entertainment (e.g., movie, game, advertisement, etc.).

In some examples, a system of the technology may employ filters 103 to filter particles from a flow of air prior to providing the flow of air to a user. A filter 103 may be capable of removing volatile gases as well as odours, bacteria, and viruses from the ambient air. The air which has been passed through the filter may then be provided to a user. The filters may come in the form of a cartridge which can easily be placed into and removed from the system. Different filters may provide different type of filtration depending on the needs of the user. For example, some filters may provide odour elimination while other cartridges provide bacteria removal. In some examples, multiple filters 103 may be utilized. For example, a pre-filter may be placed on the inlet of the flow generator 1603 and a primary filter at the outlet of the flow generator 1603.

In some embodiments, a user flow interface 104 is intended to deliver the air to the user by generation of an air curtain. The air curtain may divide the ambient environment into two separate environments, an inner environment and an outer environment. The inner environment may allow cleaned air or air with controlled sensory characteristics such as particles, scent, humidity, temperature, etc. to be delivered to the user's airways. Optionally, the user flow interface 104 of the CAS 101 may be hidden in an item of clothing (e.g. scarf or turtle neck sweater). Alternatively, it may be camouflaged to visually appear like a fashion accessory rather than a medical device. The user flow interface 104 can be implemented so as to avoid or eliminate contact with the face or head. Thus, there will typically be no seal formed against the user's face. Accordingly, the user flow interface 104 could then minimize interference with the user's line of sight (i.e., it may be out of the line of sight of the user), and not be noticeable by third parties.

Sensors may be located on or proximal to the user flow interface 104 or flow generator 1603 to sense the ambient environment, such as ambient wind conditions and the level of pollution. Further, the sensors may be able to measure health metrics such as heart rate and body temperature. The information read by the sensors may be logged in real-time and may be later recalled. These sensors may be contained in the same or different housing as the flow generator 1603. Like the user flow interface 104 of the CAS 101, sensors may be hidden in an item of clothing (e.g. scarf or turtle neck sweater). Alternatively, sensors may be camouflaged to visually appear like a fashion accessory rather than a medical device. The sensors should not make unnecessary contact with the face or head. Accordingly, the sensors should not limit the user's line of sight.

Information may be received from the sensors or from an online resource. Such information may be utilized to provide feedback to a user such as through a smart phone, online profile or other internet connected device. In one example, the system may consult the weather forecast or local air quality indicators to assess the intensity of filtration required for the day. Further, information received by the sensors may be utilized to cause the system to automatically adjust or provide a warning for a user to adjust certain parameters. For example, an anemometer and accelerometer may be used to cause the user flow interface 104 and/or flow generator 1603 to modify their operation in real-time by adjusting the directional angle of an air curtain or the air speed. The information recorded by the sensors may also be used to notify a user when a filter should be replaced. For example, a filter for removing odour may be in the system, but a filter for removing pollen may be recommended due to a high pollen reading. Accordingly the system may notify a user to swap filters.

In some embodiments of the technology, a sensory monitoring and stimulation unit 105 may be utilized. A sensory monitoring and stimulation unit 105 may include scent cartridges or other sensory cartridges for providing a physical effect carried by air to the user flow interface 104. These scent and sensory cartridges may be easily replaceable. Further, the cartridges may contain a variety of stimulants including projectable substances with different scents, textures, and temperatures. These projectable substances may be of any viscosity, air/moisture ratio, moisture content, or particle size.

The flow generator 1603 may be built as an affordable, portable unit. Accordingly, the flow generator 1603 may be small, lightweight, and battery powered. The flow generator 1603 may be worn or mounted to the user's body. It may also be attached to the user's belt or strap worn on the user's arm. In some embodiments of the technology the filter 103, sensors, sensory monitoring and stimulation unit 105, and flow generator 1603 can be contained in the same or different housing. An air delivery conduit 1604 may also connect the flow generator to the user flow interface 104 which may be housed within or outside of the housing.

In some examples, the flow generator 1603 may have wireless connectivity to upload/download data relating to usage, weather, and ambient conditions. Further, data from the flow generator 1603 may be recorded for quantifying self-functionality. The quantity of cleaned air breathed in by the user may be recorded and the remaining expected life for the filter cartridge/aromatic cartridge/sensory particle cartridge used may be recorded.

In some examples of the technology, a 4D entertainment system may be connected to any game consoles, such as Sony's Playstation, Microsoft's Xbox, or other media playback devices like Blu-Ray players or Smart TV's. Connection to these devices may be through wireless or wired connections. The 4D entertainment system may upload and/or download data to these devices.

Flow Generator

Introduction

Clean air systems (CAS) and 4D entertainment systems may both create air curtains to provide air to a user. Air curtain systems typically require significantly higher air flow rates than those provided for positive airway pressure (PAP) therapy provided from a typical mask interface. A positive air pressure, relative to an ambient air pressure, may be maintained in the enclosure maintained by the air curtain to prevent ingress of air from outside of the enclosure. Typically such a positive pressure may be lower at the user's face than those achieved by PAP therapy, as a low positive pressure may be sufficient, whereas for PAP therapy the pressure must be sufficient to open a user's airways and maintain them in an open state.

Air flow provided by a system which creates an 'air curtain' may provide air at a high flow rate. Additionally, the required pressure across the blower (i.e. pressure gain from an inlet of the blower to an outlet of the blower) may be large. For example, as the blower may still need to overcome pressure losses within the system. For example, the air pressure may significantly drop between the outlet of the blower and the user's face, as the air flow travels through one or more of, filters 103, air delivery conduits 1604, user flow interfaces 104 and connectors there between. The differences in pressure between the outlet of the blower and the user's face may further vary according to a number of other parameters, including, but not limited to, the geometry of the pneumatic path (e.g. cross-sectional shape and area, length of path), the type of filters used, and the dimensions of the filters used.

As such, a flow generator 1603 which generates a high flow rate while creating a positive air pressure at a user's face is desirable. Accordingly, certain motors and blowers may be more suited for the task than others.

Motor-Blower

Blowers may be configured to have multiple stages in series. That is, having one blower stage configured to receive an air flow exiting another blower stage. By having such a configuration, the pressure of the air flow may be increased, but the same flow rate may be maintained. Examples of such blowers include those disclosed in PCT Patent Application WO2013020167 and WO199806449, which disclose blowers configured in two, three, four or more stage designs.

Blowers configured with multiple stages in series may be more suitable for PAP applications where the aim is to provide sufficient pressure to open a user's airways, such as by providing up to 30 $cmH_2O$ at the patient interface. Blowers typically comprise a motor to provide rotational motion, and a maximum rotational speed of the motor is often predetermined as a part of the design of the motor. Thus, to achieve a desired air pressure, additional blower stages may be introduced in series to increase the air pressure at the same rotational speed. FIG. 45 is an exemplary fan curve of a blower rotating at 46.8 k RPM, comprising one or more stages connected in series to increase the pressure of the air flow exiting the blower for a predetermined rotational (e.g., motor) speed. As can be seen in FIG. 45, as additional stages are introduced in series to increase the air pressure increases even though rotation of the blower does not.

For an application where larger flow rates are desirable, a series blower arrangement may not be suitable. For example, an air curtain arrangement may be implemented with a flow rate exceeding typical, or maximum predicted flow rate of a PAP device, with a lower pressure characteristic as described below. Further, an air filtration system comprising a mask and vent (e.g. continuous vents or variably configured vents) may require higher flow rates as a user who is awake utilizes higher tidal volumes than a sleeping PAP user. A user's tidal volume may be even higher, if the user is performing a physical activity, such as moderate exercise (e.g. walking, bike riding, golfing). Also, a worker may require a higher tidal volume, and the worker may be working in a potentially polluted environment like a construction site. The pressure provided may be much lower within an air curtain arrangement, than those provided to a patient undergoing a PAP therapy. The pressure off an air-current arrangement need only provide filtered air at a positive relative pressure to the ambient to prevent air ingress, rather than a PAP device which needs to open one's airways through pneumatic pressures.

FIG. 46, is an exemplary fan curve of various blower implementations, such as multiple blower stages in parallel implemented to increase the flow rate of the air flow exiting the blower for a predetermined rotational (e.g., motor) speed.

FIG. 46 shows that for a predetermined flow rate (e.g. 50 L/min as shown in the graph), introduction of additional blower stages connected in series significantly increase the pressure at the blower outlet, whereas where the additional blower stages are connected in parallel, the pressure at the blower outlet remains largely unchanged. The introduction of additional blower stages connected in parallel significantly increase the flow rate at the blower outlet for a predetermined pressure (e.g. 15 cmH2O as shown in the graph) whereas the additional blower stages connected in series do not significantly impact the flow rates at the blower outlet. Accordingly, blowers connected in parallel may be more beneficial to an air curtain arrangement as greater flow is provided without an increase in pressure.

Figure 2:
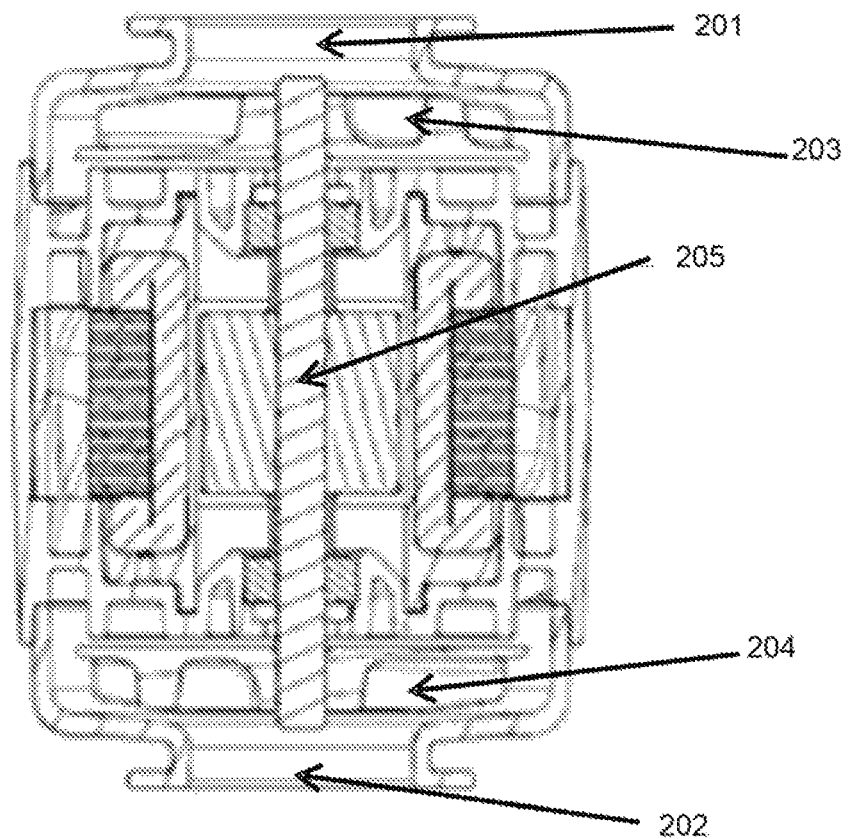

An example of a suitable blower for an air filtration application may be a blower with a plurality of stages in parallel and driven by a single shaft as shown in FIG. 2. Such a blower may comprise a first inlet 201 at a first end, and a second inlet 202 at a second end, and a shaft 205. The shaft 205 may be fixedly coupled to a first impeller 203 and a second impeller 204. The first 203 and second impeller 204 may be driven by the shaft 205. The blower may also comprise first and second outlets (not shown), to deliver the air flow received by the first 201 and the second inlets 202, respectively at an increased pressure. Within a high-flow low pressure application, scroll outlets may be used. Scroll outlets may offer an increase in efficiency and thereby enable lower power consumption for battery-based uses. Further, a scroll outlet may allow a smaller size to be achieved in packaging.

Figure 3A:
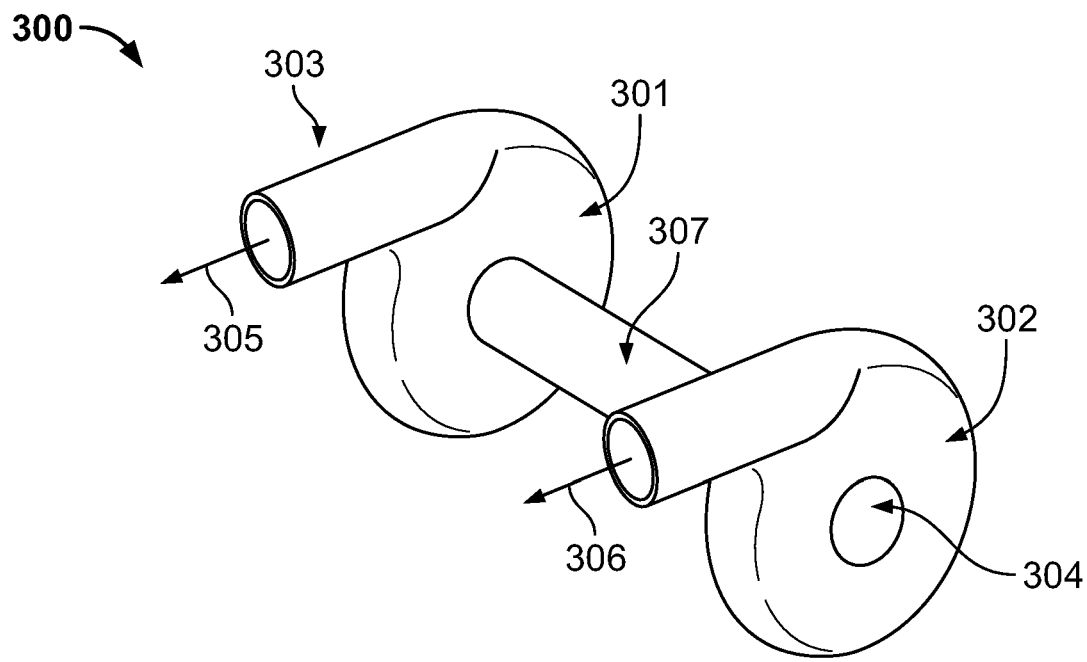

FIG. 3A shows an isometric schematic representation of a blower 300 with two stages in parallel. The blower may have two stages 301 and 302 and a motor 307. Air may be drawn in from two inlets 303 and 304 and pushed out through two outlets 305 and 306. The flows of air exiting the blower may, in some implementations, be combined to form one flow, or remain separate, for example to be directed to different areas of the user. In some forms, an air curtain type device may comprise multiple outlets, such as one to provide an air curtain and one to provide a flow of fresh air to the user for breathing. In such a form, the flow of air from a first outlet may provide an air curtain flow and the flow of air from the second outlet may provide a fresh air flow to the user.

Figure 3B:
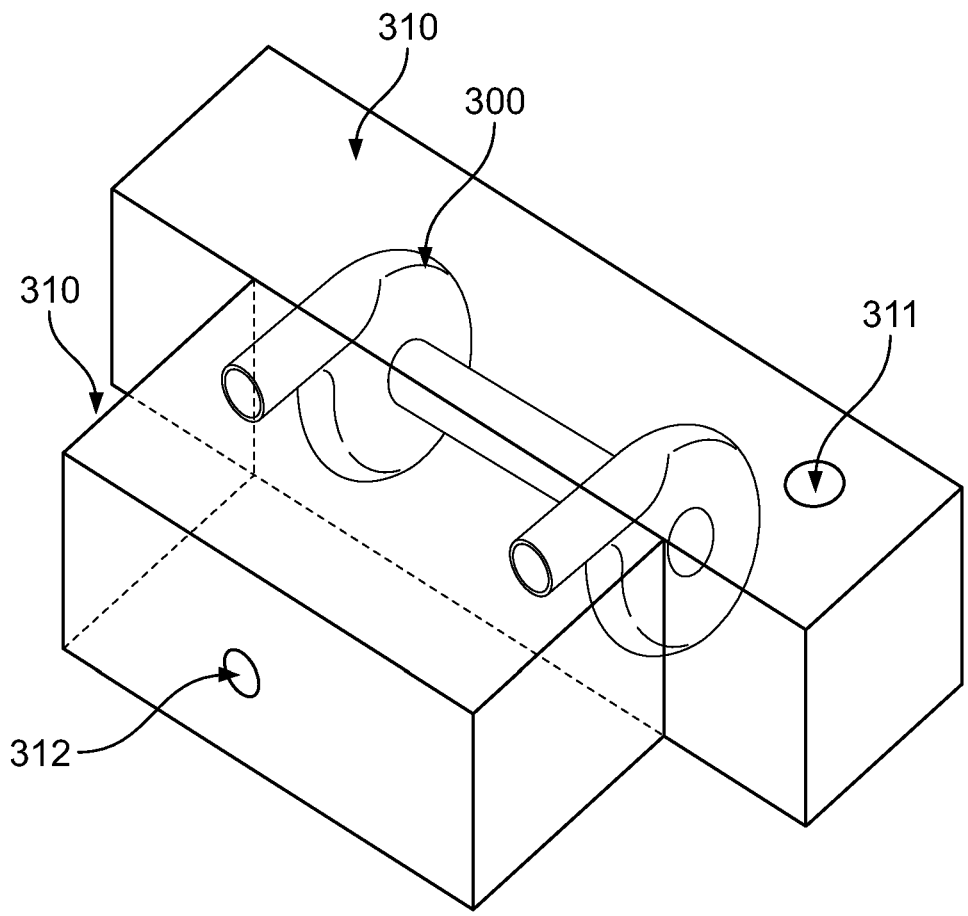

In another example, the blower may comprise a mixing chamber downstream of the individual outlets as shown in FIG. 3B. The mixing chamber 310, may house the blower 300, and receive a plurality of flows from the blower stages 301 and 302, and combine the flows to form one flow of air. The air provided to the blower stages 301 and 302 may be received through an inlet 311 in the mixing chamber. The one flow of air may be output through an outlet 312. In some forms, the mixing chamber may be configured to reduce an amount of noise produced, such as by being configured to act as a muffler. The mixing chamber may thus comprise one or more of acoustic foam, Helmholtz chambers, and baffles, etc. The mixing chamber may be configured to reduce tonal noise and/or noise output by the blower.

Figure 4:
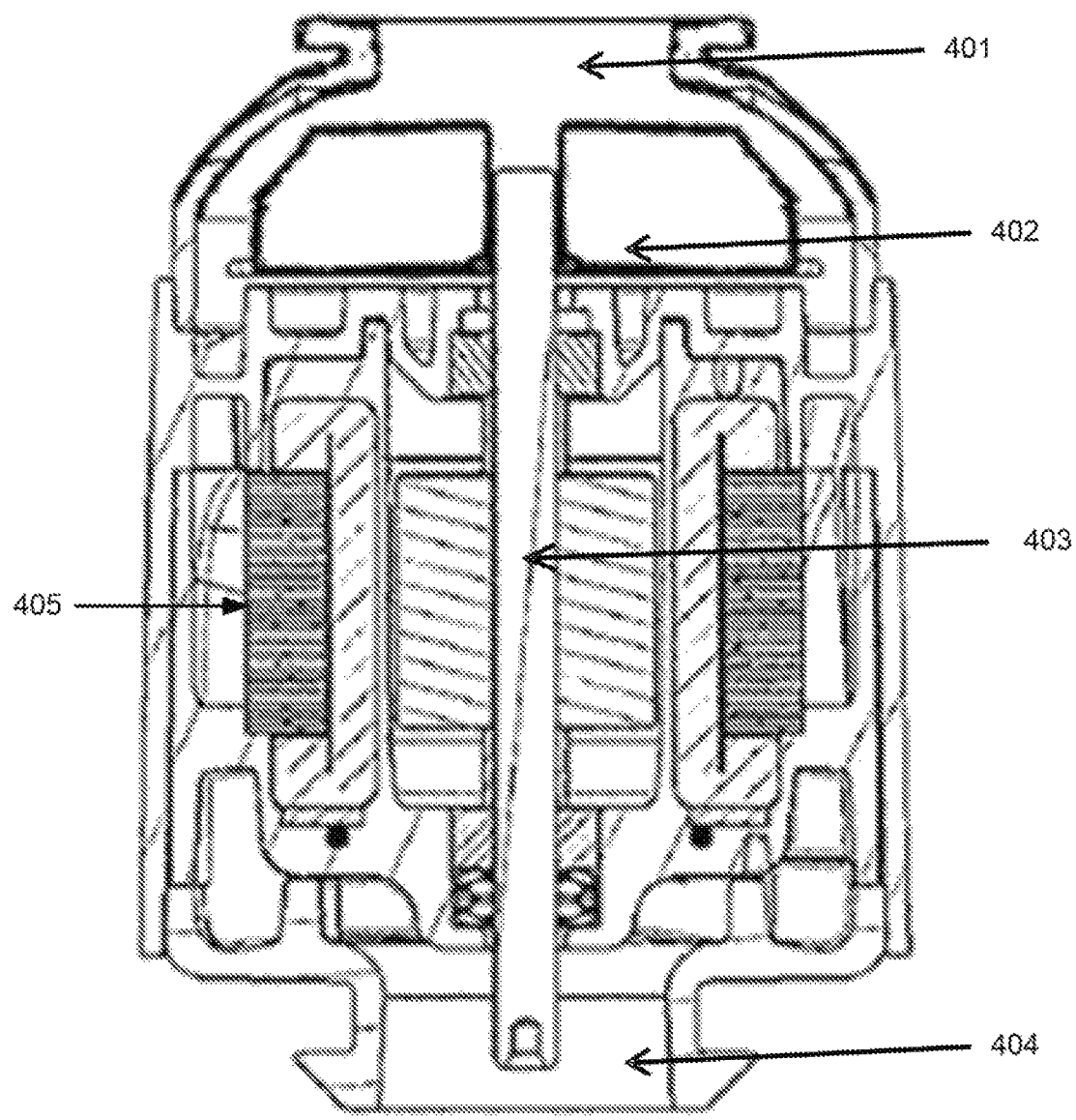

Another suitable example of a motor suitable for providing an air curtain may be a single-stage blower as shown in FIG. 4. The single-stage blower may comprise a motor 405, a single impeller vane 402 with a relatively small aspect ratio between the height and the radius, a shaft 403, an inlet 401, and an outlet 404. In some embodiments, the impeller may have a height which is greater than a portion of the radius of the impeller, to deliver a large volume flow rate of the air flowing through the blower at a predetermined rotational speed.

Figure 5:
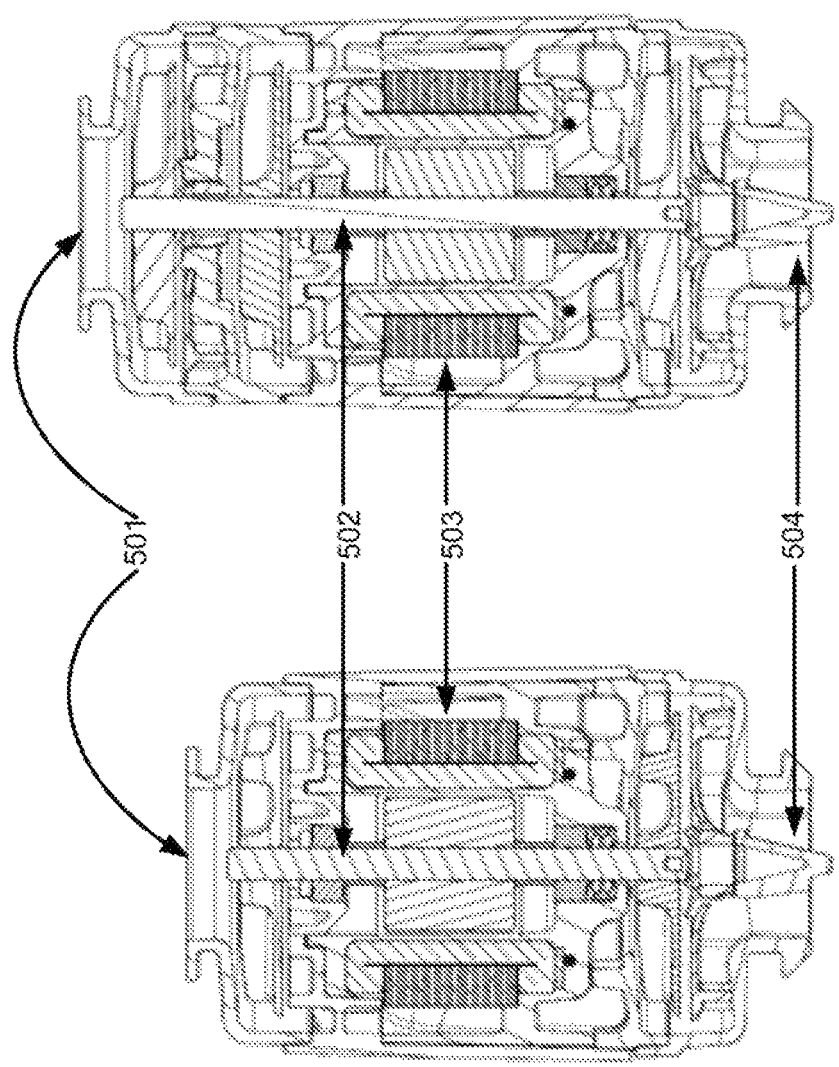

As discussed above, motors with multiple blower stages may be used. FIGS. 5A and 5B show motors with multiple blower stages. FIG. 5A shows a two stage blower and FIG. 5B shows a three stage motor. Such blowers may be centrifugal blowers with inlets 501, outlets 504, shafts 502 and motors 503. Examples of similar blowers are described in more detail in PCT Patent Application WO2013020167. Such blowers include blower stages arranged in series, and thus may be suitable for applications wherein the pressure required at the outlet is relatively high, in comparison to arrangements comprising similarly configured blower stages in series.

Figure 6:
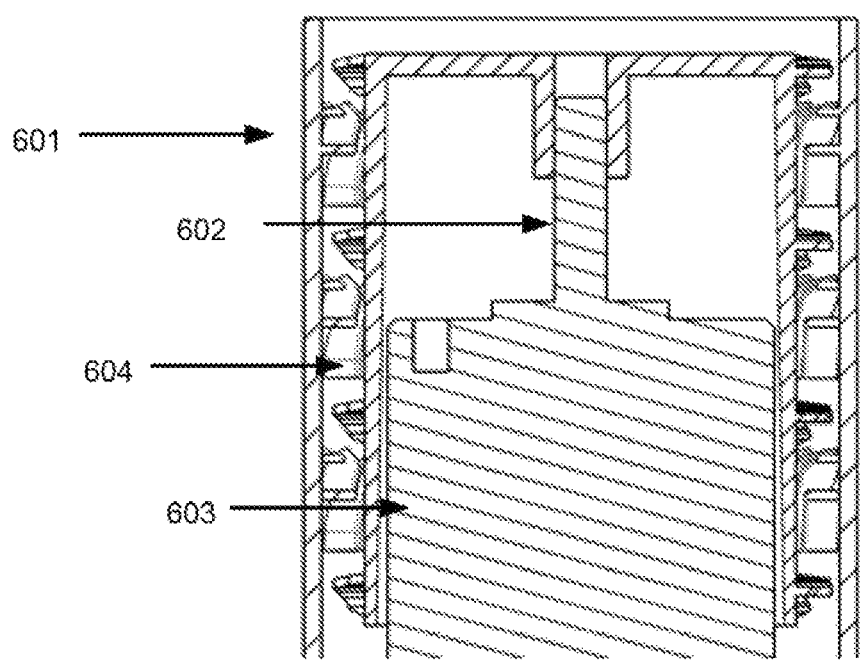

An axial blower, as shown in FIG. 6, may be suitable for the present application. An axial blower may typically produce a high flow rate against a relatively low pressure in comparison to a centrifugal fan. As shown in FIG. 6 the axial blower comprises a rotor 603 coupled to the motor shaft 602, and a blower housing 601 surrounding the rotor and comprising the stator vanes. The blower may comprise a plurality of stages 604, each of which may be located on one or more separate components or a plurality of stator or rotor stages may be located on a single component as shown below, separated axially.

Figure 7A:
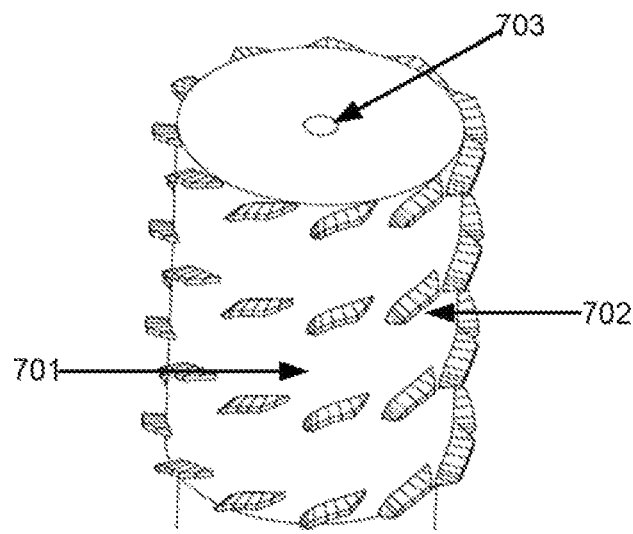
Figure 7B:
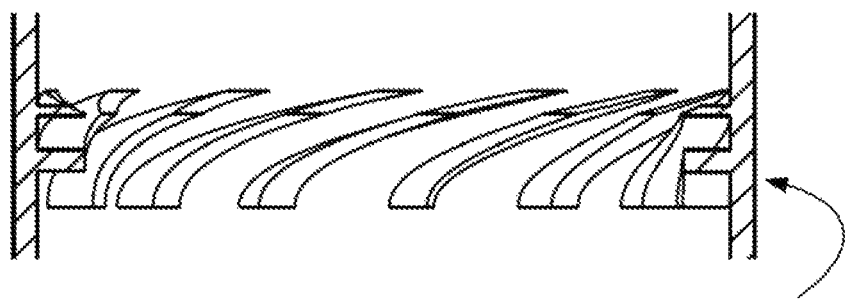
Figure 7C:
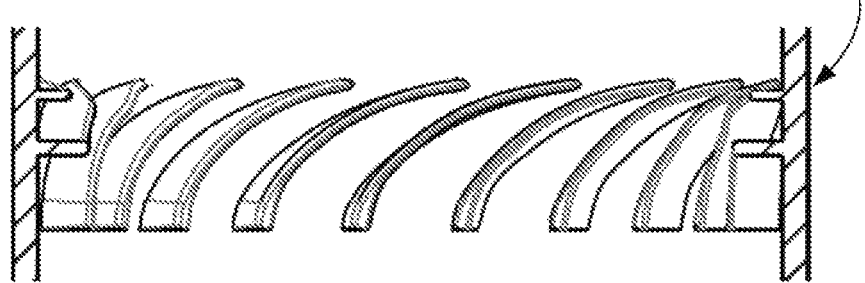

FIG. 7A is an example of a rotor compatible with the axial blower shown in FIG. 6. The multi-stage rotor may be formed on a single, moulded body 703 that includes an axial recess 703 for coupling with the motor. Multiple rotor stages are integrally formed on a single body of the rotor. An integrally formed single body rotor may reduce manufacturing cost, reduce the number of components, and also reduce the manufacturing tolerances. Each stage 702 is shown to be axially aligned with each other and of same geometry. FIGS. 7B and 7C show axial stator stages which may be formed by the rotor of FIG. 7A. The rotor stages 704 may align with the blower housing 705 to form an axial stator stage. In some forms, the stages need not be axially aligned, and each individual stage may be differently arranged from another stage.

Figure 8B:
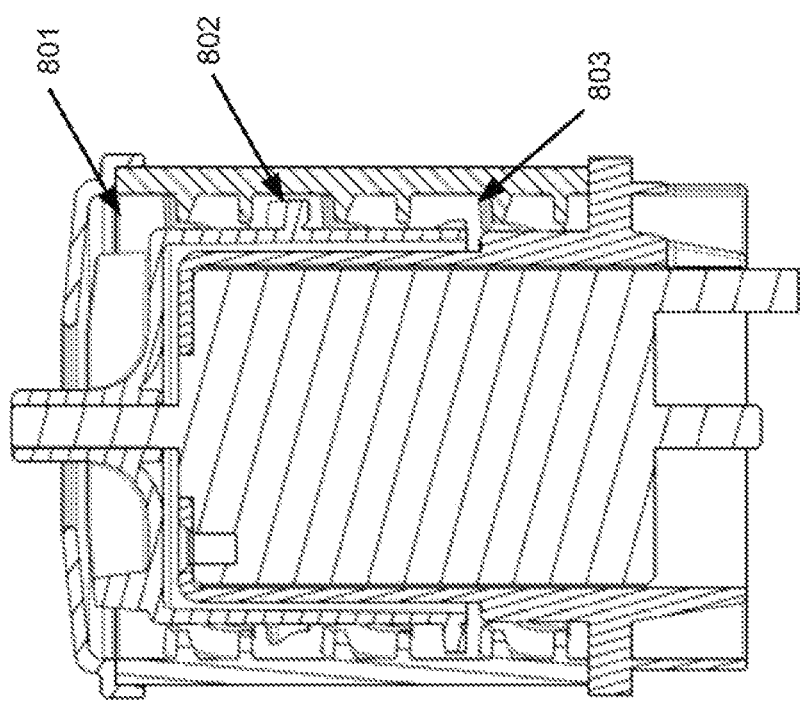
Figure 8A:
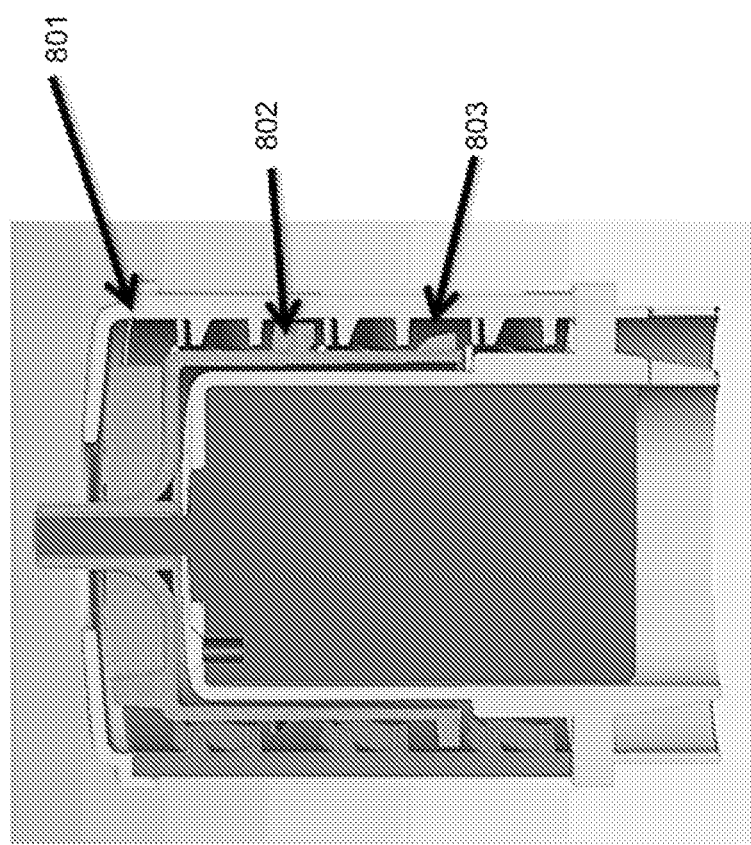

Another example of a suitable blower may be one that comprises both a centrifugal stage and an axial stage, as shown in the FIGS. 8A and 8B. As shown in FIGS. 8A and 8B, a blower may comprise a centrifugal stage 801 as the first stage. From the centrifugal stage air may travel downstream along an annular path formed in the blower through the two axial stages 802 and 803. This configuration may provide a combination of pressure and flow increase to the air flow to suit certain examples of the present technology.

A rotor, which comprises a centrifugal stage at the top positioned towards an inlet, is shown in FIGS. 9A-9C. The rotor may comprise impeller blades 903 and an impeller shroud disc. Further, the rotor may comprise an axially-extending wall 901 on which axial blades 902 are formed. The axially-extending wall may also form a part of the annular flow path through which the air flow travels. The rotor in this form may also comprise a circular cavity 904, through which the rotor is coupled to the motor.

Figures 10A, 10B:
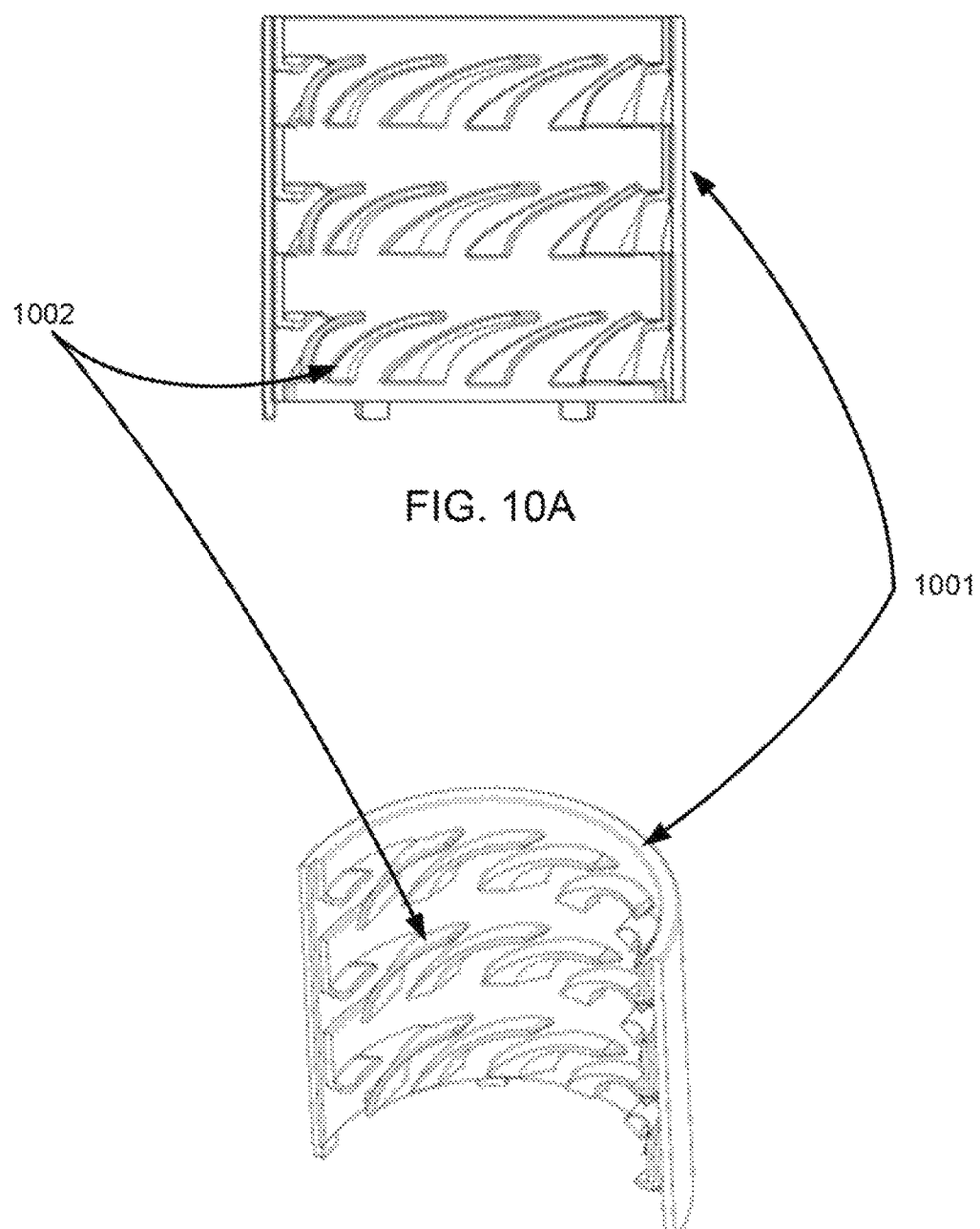

FIGS. 10A and 10B show a first half of the outer housing 1001 with an inner wall. Stator vanes 1002 may be formed on the inner wall. The outer housing 1001 is configured such that the stator vanes 1002 for the centrifugal stage and the axial stage of the blower are both formed on a straight wall. Such a construction may improve manufacturability of the housing. Each of the two halves of the outer housing 1001 may comprise a key and a complementary recess configured to engage with each other. Construction of the outer housing 1001 in multiple parts allows each part to be moulded with stator vanes 1002 integrally formed and projecting inwards from the inner wall.

Figure 11A:
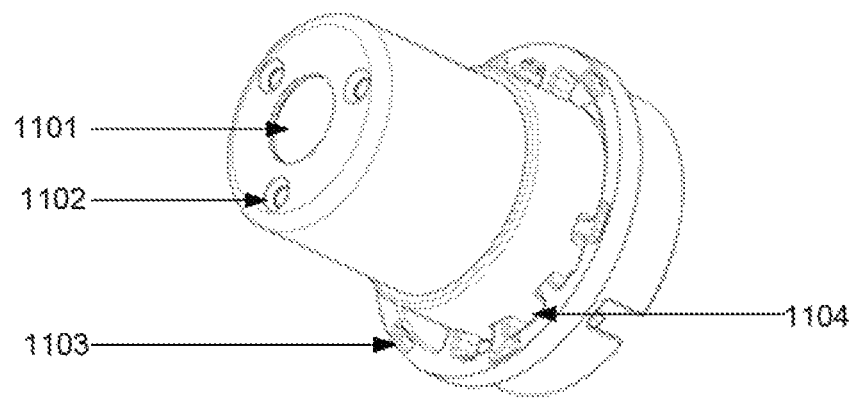
Figure 11B:
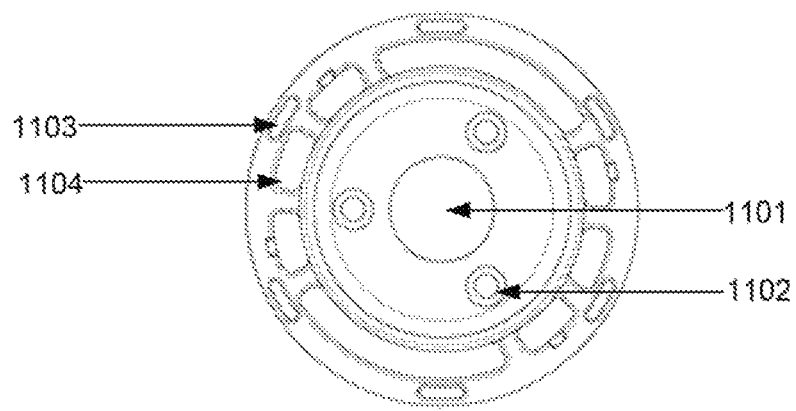

The motors may be housed with a motor house. FIGS. 11A and 11B show example motor housings. The motor housings may include a cavity 1101 which a shaft can protrude out of. Further, the motor housing may include a set of outlet cavities 1104 for the air flow. The motor housings may also include connection points 1102 and 1103, for connecting the motor housing to the motor.

Another example of a motor which may be used in an air curtain system may be a tesla blower. A tesla blower may have thin flat discs which may provide the blower with a slim profile. Accordingly, the blower may be easily concealed and can be unobtrusive. A tesla blower may operate without producing a tonal noise output, as a Tesla blower is blade-less.

Motor-Blowers for the Present Technology

One or more of the above blowers may be suitable for use with examples of the present technologies such as an air curtain device, an air filtration device with a patient interface or an entertainment air system.

The design and selection of an appropriate blower may vary according to the intended use and shape or size of the system. A blower may be increased or decreased in size to change an output flow and/or pressure. However, design of an appropriate blower configuration would allow design of a blower for the present technology which would present the least obtrusiveness to its user and maximising its operating time by minimising the power consumption. For example, a blower with too many stages in series may result in too large of a blower for practical use.

If a blower is located proximal to the point of delivery of the flow of air to the user, for example on a shoulder of the user, and the air delivery conduit is of a relatively large diameter, for example 19 mm inner diameter, a blower capable of providing the desired flow rate at a low pressure may be sufficient. Such a blower may be a single-stage centrifugal blower or a multi-stage axial blower. However, if higher flow rates are desired, a centrifugal blower may comprise a plurality of blower stages connected in parallel.

In another example, a blower may be located distal to the point of delivery of the flow of air to the user, for example on a user's hip. If the blower is connected to a user flow interface by a narrow tube a blower will need to be capable of providing a high pressure. Accordingly a hybrid axial and centrifugal blower may be appropriate.

Air Curtain

An air curtain may be generated to divide the ambient environment into two separate environments, an inner and an outer environment. The inner environment substantially contains the air coming out of an air curtain system (e.g., user flow interface), while the outer environment contains air which has not gone through the air curtain system. A positive, or equivalent, air pressure, relative to an ambient air pressure, may be maintained in the inner environment maintained by the air curtain to prevent ingress of air from outside of the air curtain "enclosure".

Figure 12:
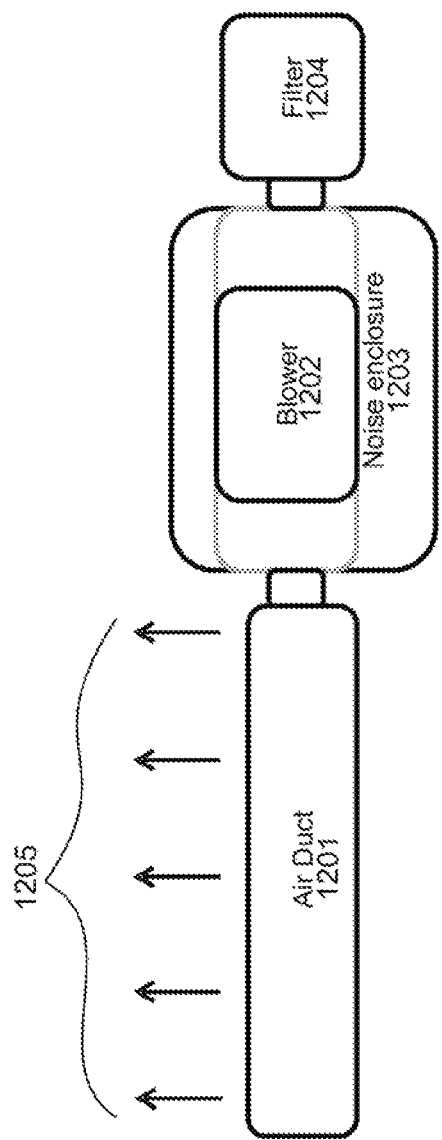
Figure 13:
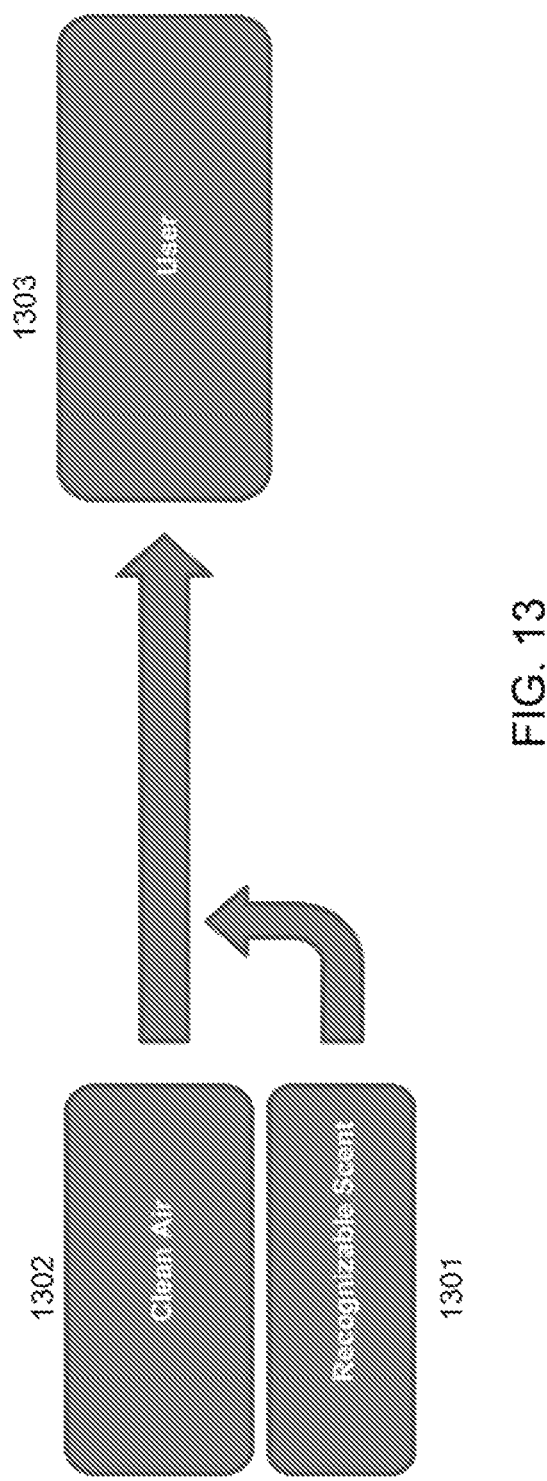

A schematic for an 'air curtain' system is shown in FIG. 12. In the schematic a blower 1202 is positioned close to the air duct 1201. The blower 1202 is positioned close to the air duct 1201 to minimise pressure drop and maximise battery life. For example, the air pressure may significantly drop between the outlet of the blower and the user's face, as the air flow travels through filter 1204, conduits, and air duct 1201. The differences in pressure between the outlet of the blower and the user's face may further vary according to a number of other parameters, including, but not limited to, the geometry of the pneumatic path (e.g. cross-sectional shape and area, length of path), the type of filters used, and the dimensions of the filters used. The blower 1202 and filter 1204 may be part of a flow generator.

In the system of FIG. 12, the air-duct 1201 may be, for example, 25 cm long and 19 mm diameter and the blower 1202 is suspended within a noise enclosure 1203, with a large inlet filter 1204. The system of FIG. 12 may have a constant flow of, for example, 150 L/min and a pressure across the blower of, for example, 12 $cmH_2O$. The estimated power consumption may be 13 W. The filter 1204, conduits, and air duct 1201 may cause pressure losses. In the example air curtain system, the air duct 1201 may have a pressure loss of may be, for example, 0.25 $cmH_2O$ and the filter 1204 may have a pressure loss of 4 $cmH_2 0$. Further, each air delivery conduit may suffer pressure loss of 0.1 $cmH_2O$. Accordingly, assuming quiescent power of 1 W, a 6 cell battery (12 Wh cell capacity) could last 4.8 hours out-of-box. It is noted that the numbers provided are exemplary and other numbers and ranges with the same technology are possible.

Figure 31:
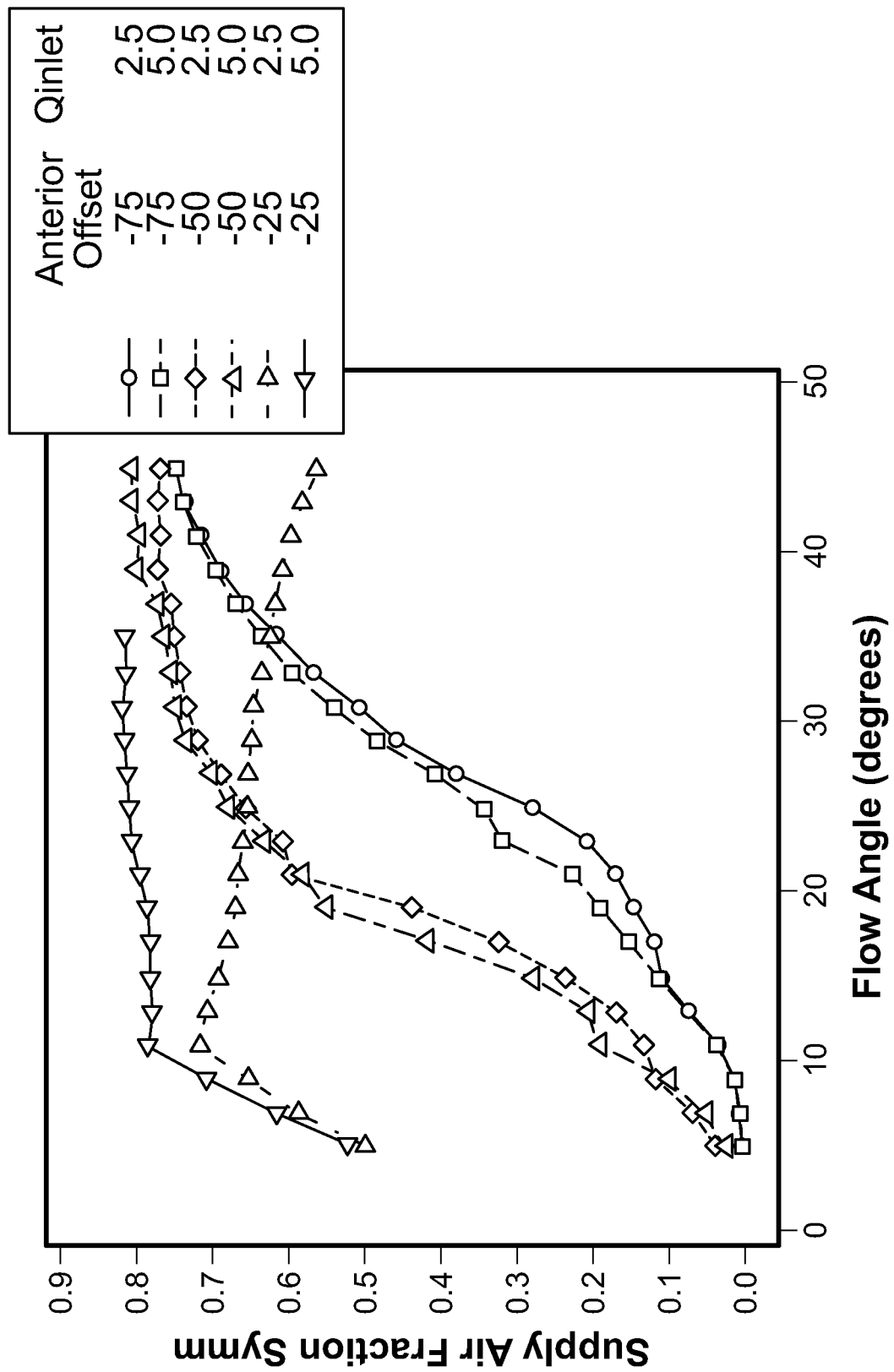
FIG. 31 is a scatterplot of air supply illustrating an embodiment of the present technology.
Figure 32:
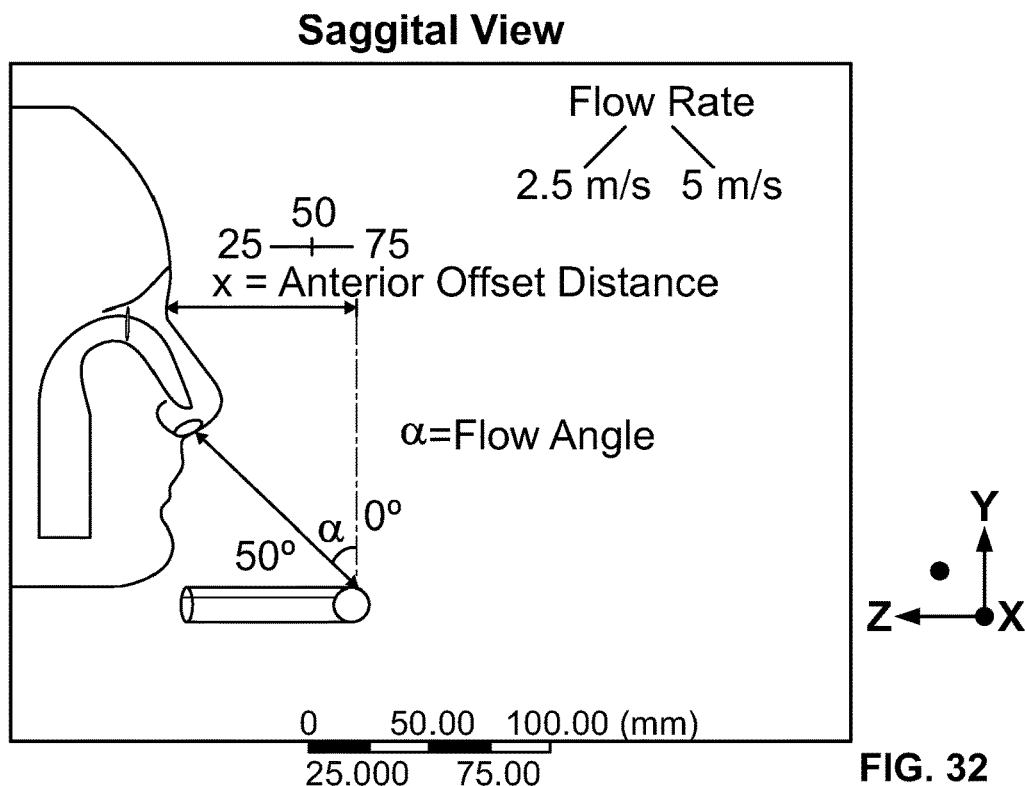
FIG. 32 is an illustration of a sagittal view of a user and user flow interface suitable for an embodiment of the present technology.

A proper flow angle may provide higher efficiency in providing air from an air curtain system. The flow rate of the air may have less impact than the flow angle in terms of increasing the percentage of air breathed in by a user of an air curtain system. Turning to FIG. 31, results of a simulation showing the percentage of air provided by an air curtain system which is breathed in by a user, ranging from 0% to 90% is presented on the Y-axis. During the simulation readings were taken at a variety of angles, distances, and flow rates. As shown in FIG. 31 two flow rates at 150 Litres/minute (2.5 metres per second) and 300 Litres/minute (5 metres per second), labelled as Qinlet, were used. Each of the two flow rates was applied at three different distances measured in mm between the user flow interface such as an air duct and the nares of the user. These distances are labelled as AnteriorOffset within FIG. 31. For each distance, a range of flow angles of the outlet of the user flow interface to the nares is measured in degrees and shown on the X-axis labelled as FlowAngle (α). All the measurements of the simulation were taken at an ambient air temperature of 25 degrees Celsius with no ambient air velocity. FIG. 32 shows a sagittal view of how the anterior offset distance (AnteriorOffset) and flow angle (α) were measured.

As can be seen in the scatterplot of FIG. 31, the priority of significance on percentage of cleaned air breathed in by the user is angle (FlowAngle), distance (AnteriorOffset), then flow rate (Qinlet). As flow is directed towards a user's airways with a flow angle of about 40 degrees the percentage of cleaned air breathed in by the user is higher than 60% in most simulations.

Figure 33:
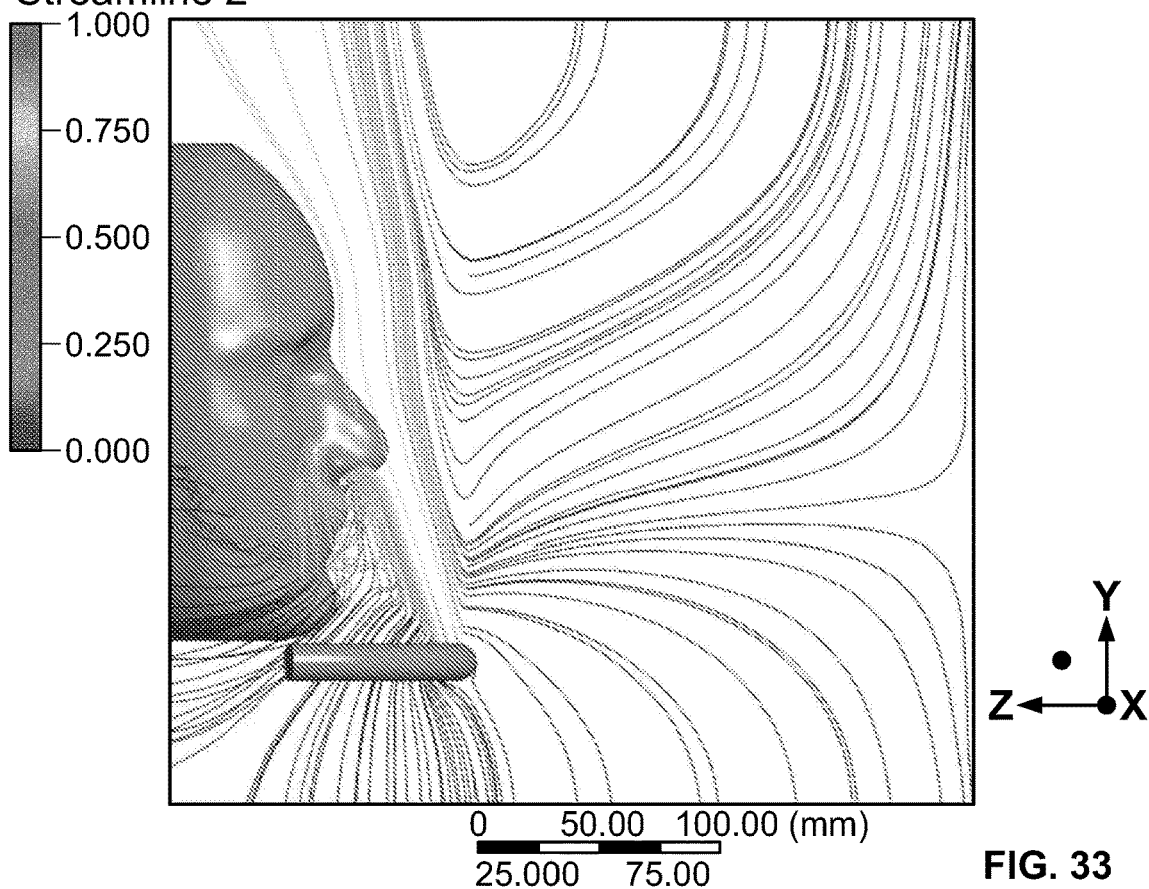
FIGS. 33 and 34 are illustrations of supply mass fraction simulations for embodiments of the present technology.
Figure 34:
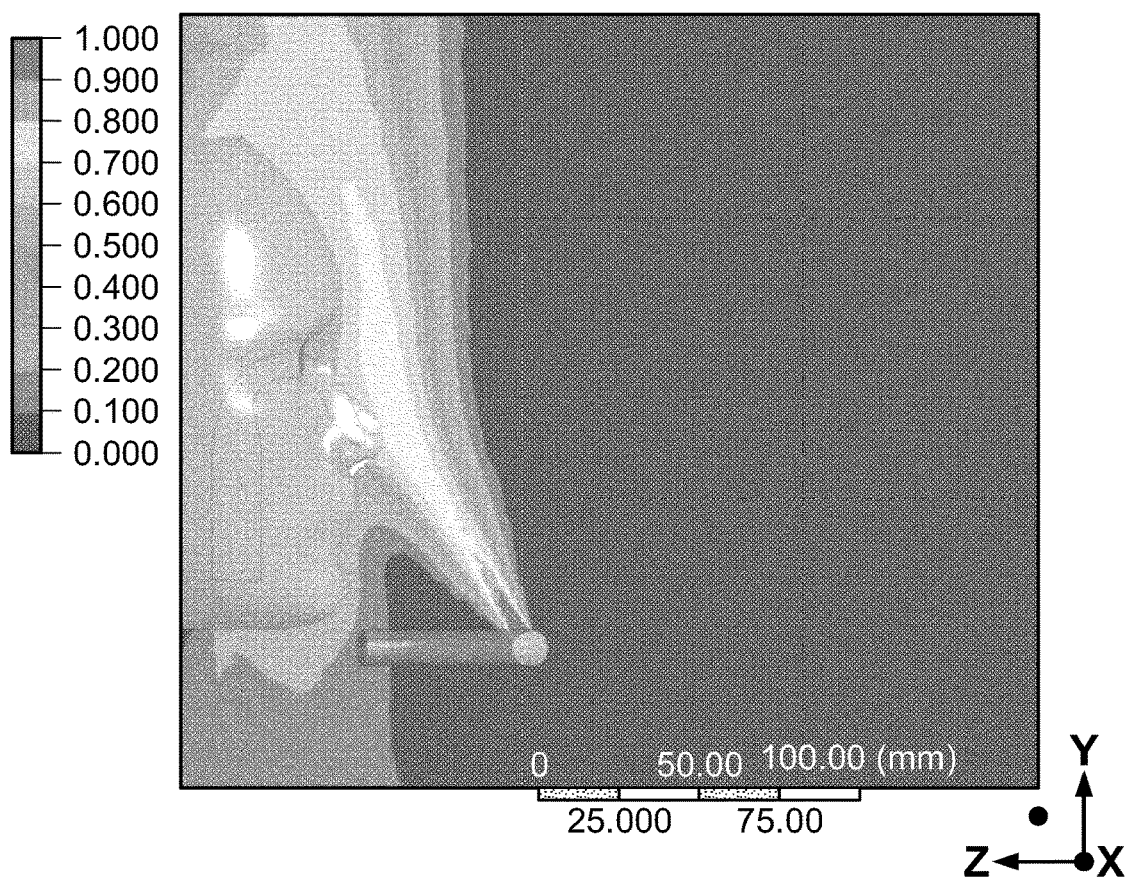

The supply of air from an air curtain system with an anterior offset of 50 mm is shown in FIG. 33. The flow angle is at 17 degrees and flow rate is 2.5 meters/second. As can be seen in FIG. 33, the air supply from an air curtain system at the user's nares is about 50%. In FIG. 34 an air curtain system with an anterior offset of mm is shown. The flow angle is 30 degrees and flow rate is 2.5 meters/second. As can be seen in FIG. 34, the air supply from an air curtain system at the user's nares is about 75%. The higher flow angle provided for in FIG. 34 supplies the user with a higher percentage of cleaned air from an air curtain system.

Smart Air Cleaning Technologies

An air curtain system can be used to create a clean air system (CAS). The CAS may comprise multiple filters to remove particulates and gases from air prior to providing the filtered air to a user. The CAS may also be capable of removing volatile gases as well as odours, bacteria, and viruses from the ambient air. After filtering the air, the CAS may then provide the filtered air to a user through a user flow interface 104. The air provided may be in the form of at least one air curtain. In some examples, the CAS may communicate all data on a display. The CAS may have control functions directly on the housing. In other examples, the CAS may communicate all data to a smartphone or computer program and may also present the data through an online database. The CAS may also be controlled by a graphical user interface (GUI) displayed on a smartphone, tablet, computer, etc.

Figure 1:
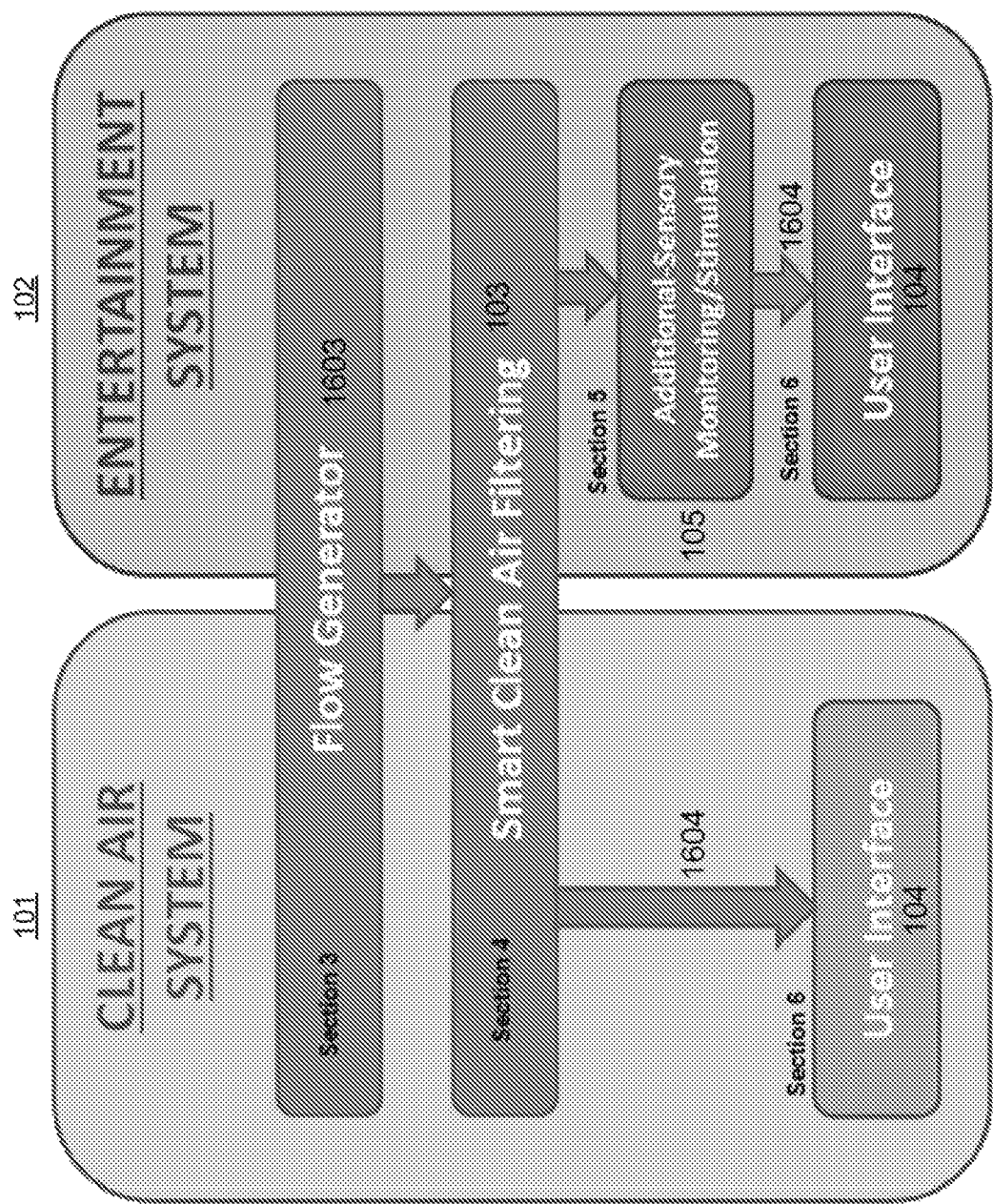
Figure 14:
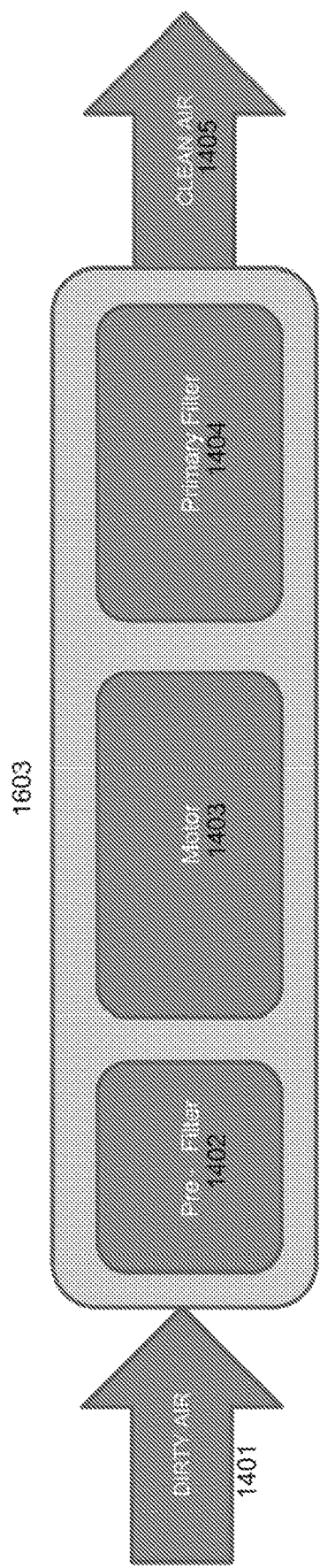

As shown in FIG. 1 an active clean air system may include a flow generator 1603, smart clean air filtering 103, and a user flow interface 104. The flow generator may be any motor as described above and can include filters and sensors. An example implementation of a CAS is shown in FIG. 14. Dirty air 1401 may be pulled into a flow generator by first being passed through a pre-filter 1402. The pre-filter 1402 removes particles from the ambient air which may damage the motor 1403. The motor 1403, as shown in FIG. 14, may then push the air through a primary filter 1404. The primary filter 1404 may remove unwanted particulates and/or volatiles from the ambient air. The filtered air may then be output to a user through a user flow interface 104 as cleaned air 1405.

Figure 35:
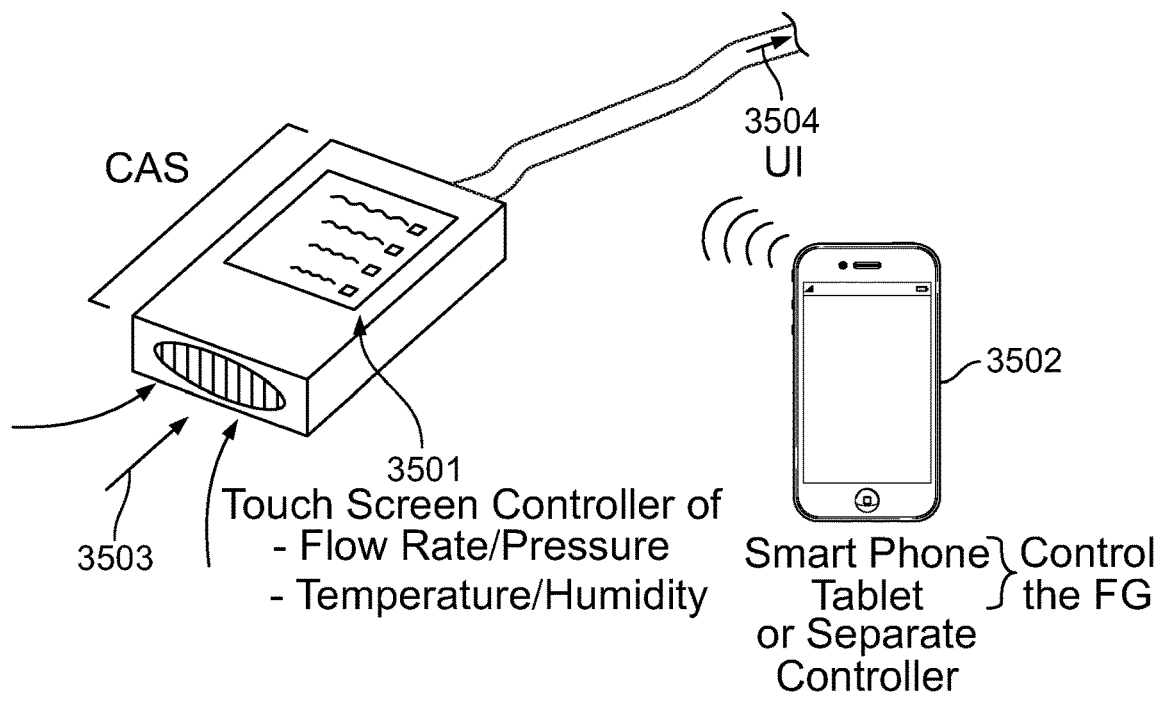
FIG. 35 illustrates an example controller in some versions of the present technology.

The CAS may further comprise a controller, 3501, to control operation of the flow generator 1603, as shown in FIG. 35. The controller 3501 may be used, for example, to adjust the flow rate of the flow generator as well as adjust the air pressure generated by the flow generator. The controller 3501 may be housed in the same housing as the CAS. A user flow interface 3504 may be directly coupled to the CAS housing the controller 3501. Dirty air 3503 may then be filtered through the CAS housing the controller 3501, and the cleaned air may then be delivered to the user flow interface 3504. The controller 3501 may include a touch-screen to allow for a user to adjust settings of the CAS such as flow rate, flow pressure, flow temperature, and flow humidity. Alternatively, the controller 3501 may be operated by a controller device 3502, which may be a smartphone, tablet, computer, standalone device, etc. The controller device 3502 may wirelessly communicate with the controller 3501 to allow for a user to remotely control the controller 3501.

Figure 36A:
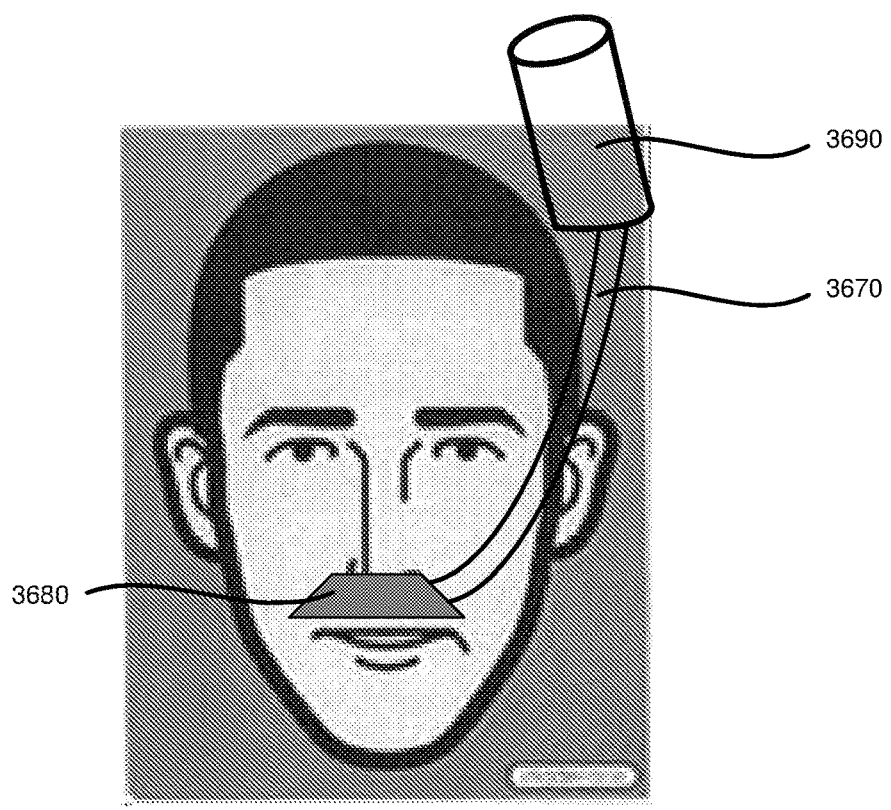
FIGS. 36A and 36B are illustrations of a passive clean air system suitable for embodiments of the present technology.
Figure 36B:
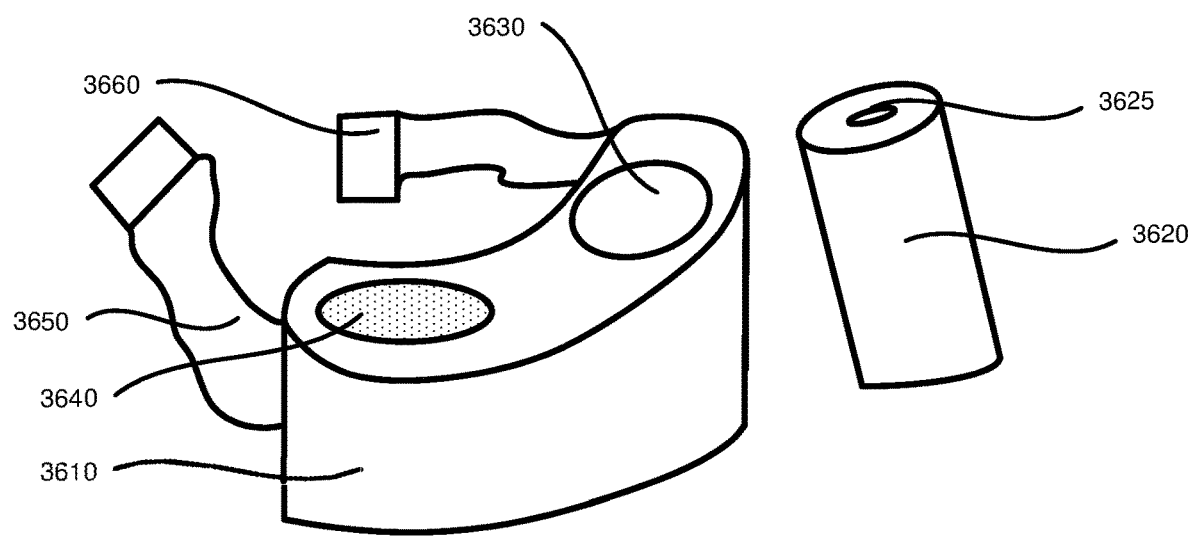

In some embodiments the CAS may be configured to operate passively, without the need for a blower or controller. For example, as shown in FIG. 36A, the CAS may be comprised of a delivery system including a cartridge holder 3690, delivery conduit 3670 and a flow interface 3680. The cartridge holder may hold a cartridge 3620, as shown in FIG. 36B. The cartridge 3620 may be comprised of one or more material including metals or plastics, which are light in weight and capable of withstanding high internal pressures. The cartridge 3620 may be charged with clean, compressed air which may release air through the delivery conduit 3670 to the user interface 3680.

A regulator valve on the delivery system (not shown) may control the flow rate of the compressed air through the delivery conduit 3670 to the user interface 3680. Such a delivery system may be small, light, and quite in operation as no blower or controller may be necessary. In some embodiments the passive cartridge delivery system may be used to supplement an active CAS by providing increased airflow when required by a user. Further, the passive CAS may also be used as a backup to an active CAS. In this regard, the valve regulator may be automatically or manually opened in the event the active CAS becomes inoperable.

The cartridge 3620 may be filled with compressed, clean air by a recharging purifier base 3610. In this regard, the recharging purifier base 3610 may filter, compress, and optionally humidify and/or scent the air. The cartridge 3620 may be placed into a charging port 3630, within the recharging purifier base 3610. The charging port 3630 may open a valve 3625, such as a spring valve, on the cartridge 3620. The recharging purifier base 3610 may then inject the filtered, compressed, and optionally humidified air into the cartridge 3620 through the open valve 3625. Upon removing the cartridge 3620 from the charging port 3630, the valve 3625 may seal. The cartridge 3620 may store enough compressed air to operate for an hour, or more or less, until it needs to be recharged.

The recharging purifier base 3610 may compress the air by using an impeller blower. In this regard, the impeller blower may draw air in through port 3640, which may include an initial filter, to filter large particles from the air before the air passes the impeller blower. The impeller blower may then push air into the charged canister 3620, compressing the air as more air is pushed into the charged canister. In some embodiments straps 3650 and clips 3660 may be attached to the recharging purifier base to allow the base to be secured to a user or other object for portability. In this regard, the recharging purifier base may be powered via battery or a wired power source.

In some embodiments, the impeller blower may push the air past one or more heating elements, which may vaporize a liquid, such as water, thereby adding humidity to the air. In other embodiments, humidity can also be introduced to the system via a separate water wick cartridge within the recharging purifier base 3610.

Figure 37A:
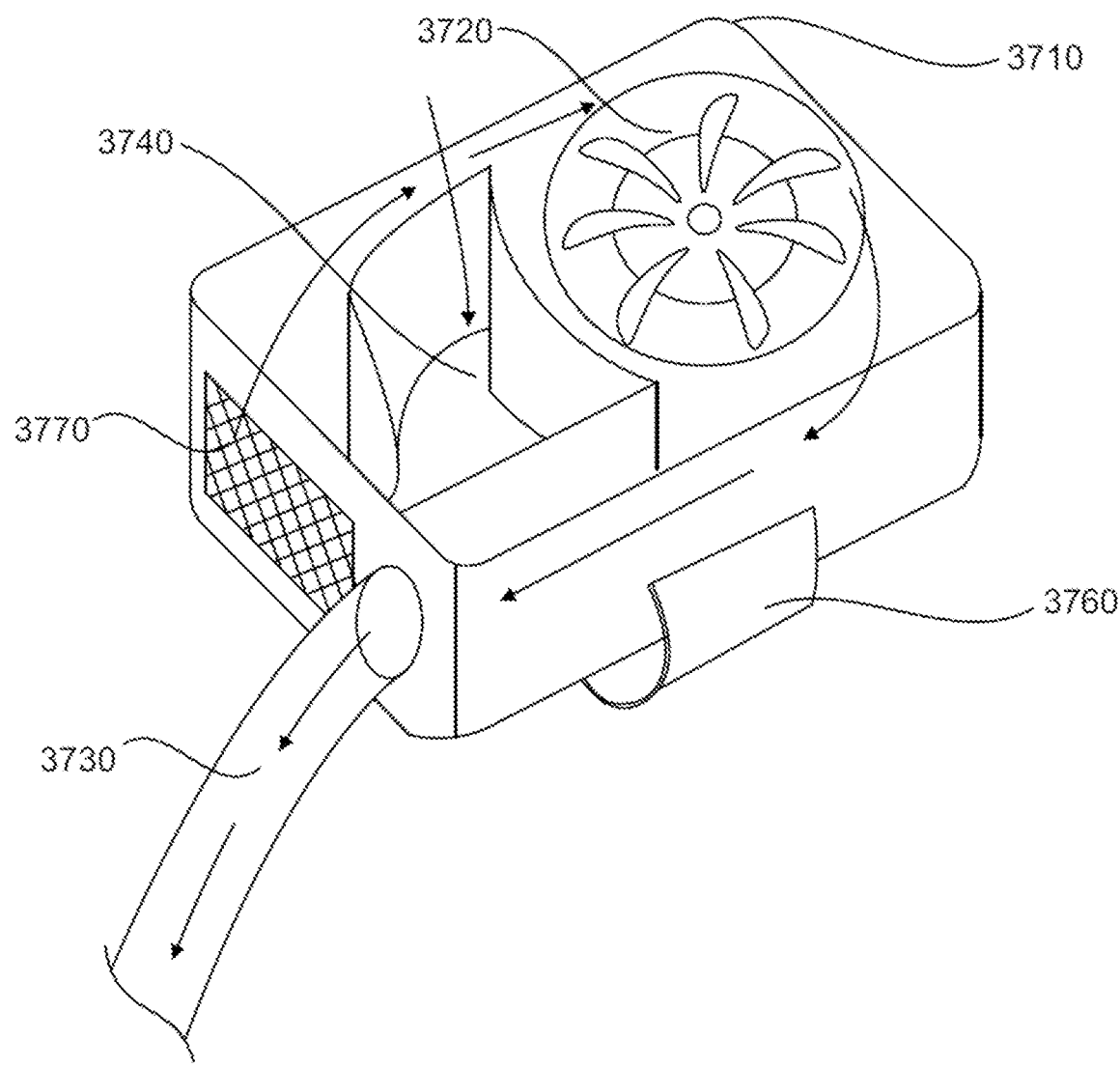
FIGS. 37A and 37B are illustrations of a compact blower suitable for embodiments of the present technology.

In some embodiments the delivery system may include an antimicrobial material lining and/or antimicrobial packets to reduce any bacteria and/or odours which may develop within the device. Such antimicrobial material may include silver thread, merino wool, or bamboo charcoal to absorb bacteria and odours. Such material lining and/or packets may be removable, replaceable, and/or washable. An air curtain system may be designed as portable and compact so that it may be carried or worn. For example, a compact blower, as shown in FIG. 37A, may include an impeller 3720 for generating airflow, a conduit 3730 for delivering the air to a patient interface, and attachment space 3740 where controllers, batteries, and/or sensors may be positioned. Additionally, the compact blower 3710 may also include an intake filter 3770, to remove airborne particles drawn in by the impeller 3720. The compact blower may be attached to a user or other object with a strap 3760.

Figure 37B:
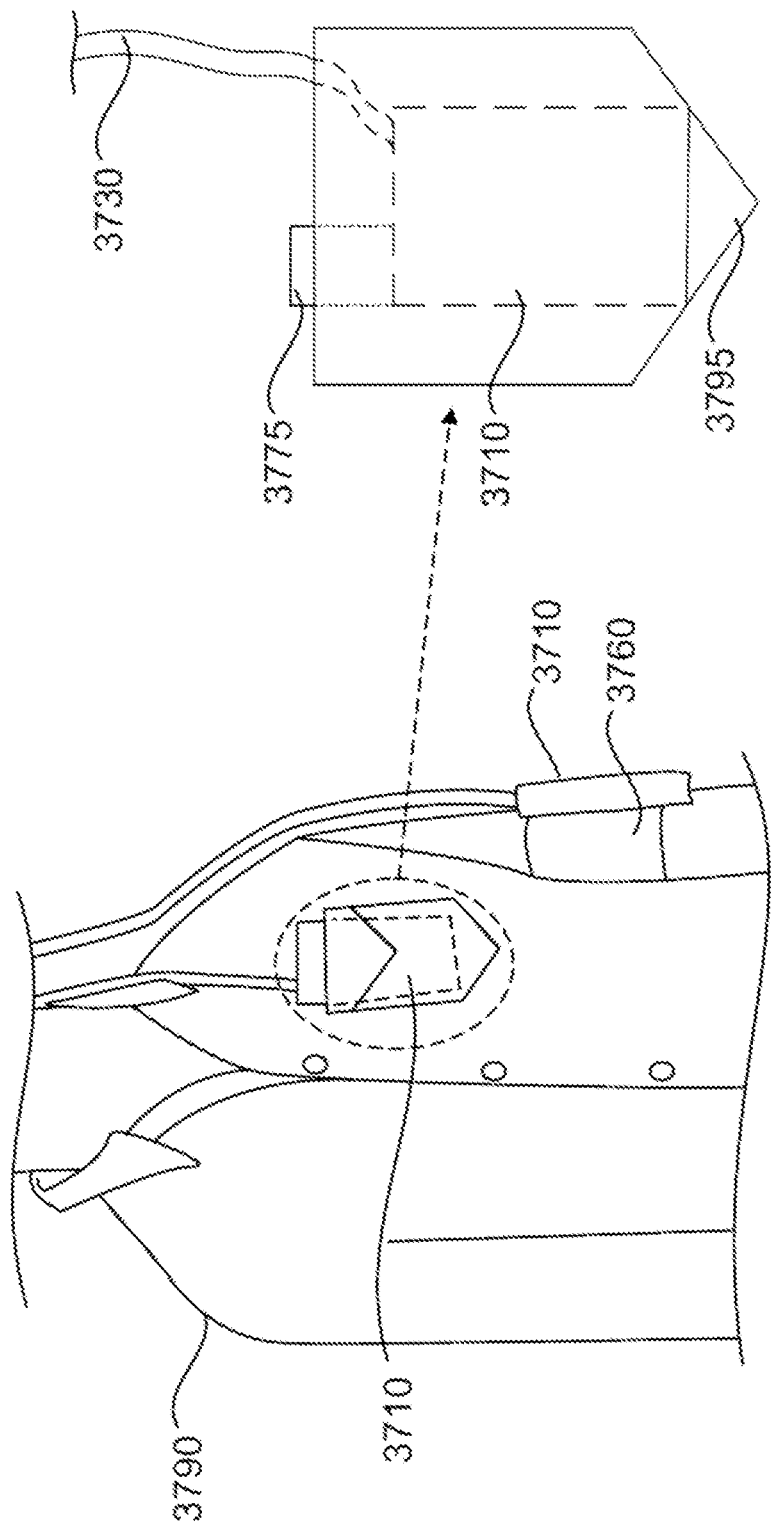

Turning to FIG. 37B, the compact blower 3710 may be constructed so that it may be attached to a user's body 3790 with a strap 3760. In some embodiments the width of the compact blower 3710 may be less than 10 mm, or more or less, allowing it to be placed in a pocket 3795. To allow for air to be drawn into the compact blower while placed in the pocket 3795 an extender may be attached. Referring to the blown up illustration of the pocket 3795 holding a compact blower 3710 in FIG. 37B, a filter extender 3775 may be attached to the intake filter 3770. As such, intake filter 3770 may draw air into the compact blower through the extender 3775 which sits outside of or just within the pocket. In some embodiments the compact blower may be placed close to the user's head to reduce the flow impedance introduced by the conduit 3730, as well as to reduce drag when the user moves their head.

As the air curtain system may be portable, it may be powered by battery power. Further, the unit should be capable of being hidden or camouflaged from view, so the user does not appear to be using a medical device. In some embodiments, the air curtain system may provide an air curtain while a user inhales, to minimize power usage.

The filters utilized to clean the air may come in the form of a cartridge which can easily be placed into and removed from the CAS. Different filters may provide different types of filtration depending on the needs of the user. For example, some filters may provide odour elimination while other cartridges provide bacteria removal. In some examples, multiple filters 103 may be utilized to increase filtering effectiveness and/or efficiency. As each filter provides filtration of different types of pollutants, multiple types of filters may be utilized at the same time. In some embodiments, the CAS may be self-configurable to automatically control the flow of the air through specific filters based on the particulates and/or volatiles which are in the user's environment. The filters may be easily replaced when they are not needed or they are no longer functioning properly. In some embodiments unrestricted filters which provide no, or very little impedance to airflow may be used.

One example filter type is a high-efficiency particulate air filter (HEPA Filter). To qualify as HEPA by US government standards, an air filter must remove 99.97% of 0.3 μm particles from the air that passes through the HEPA filter. A HEPA filter works by intercepting particle in the air as the air passes through the filter. As air passes through the HEPA filter, the particles in the air are impacted onto fibers and removed from the air.

Another example of a filter which can be utilized in a CAS is a polarized-media electret filter. Most polarized-media electronic air cleaners convert 24 volt current to safe DC voltage to establish a polarized electric field. As particles within the air pass through the electric field they become polarized. The polarized particles then adhere to a disposable fibre media pad.

An ionizer purifier is another type of filter which can be used in a CAS. Ionizer purifiers' use charged electrical surfaces or needles to generate electrically charged air or gas ions. These ions then attach to particles in the air as the air passes through the ionizer purifier. As the particles continue through the ionizer purifier, they are electrostatically attracted to a charged collector plate.

A thermodynamic sterilization filter may also be used. This technology may heat the air to around 200° C. (392° F.). As the air is heated the particles, such as bacteria, viruses, dust mite allergens, mould and fungus spores are incinerated. Possibly up to 99.9% of microbiological particles can be removed using a thermodynamic sterilization filter.

Activated carbon filters may also be used in a CAS. Activated carbon is a porous material that can adsorb volatile chemicals on a molecular basis. Activated carbon filters are usually used in compressed air and gas purification to remove oil vapours, odour, and other Volatile Organic Compounds from the air.

Electrostatic filters may also be used in a CAS. The electrostatic filter may work by sandwiching multiple layers of material together. The air may then be passed through these layers. As the air passes through the layers of material, particles in the air may be charged as a result of the friction between the particles and the filter layers. The charged particles may then attached to other layers within the filter which are of an opposite charge to the charged particles.

Photo catalytic oxidation filter systems are also possible to use in a CAS. Photo catalytic oxidation filter systems are able to completely oxidize and degrade organic contaminants. For example, volatile organic compounds with low concentrations, such as few hundred parts per million or less are the most likely to be completely oxidized. Photo catalytic oxidation filter systems use short-wave ultraviolet lights to energize the catalyst (usually titanium dioxide ($TiO2$)) and oxidize bacteria and viruses Table 3, below, provides an overview of filter types and the types of pollutants they may effectively remove.

TABLE 3

| | Pollution | |
| --- | --- | --- |
| Pollutants | Air Pollution Type | Effective Filter Types |
| Dust | Particulates | High-efficiency particulate air (HEPA) Filter |
| Bacteria/Virus | | Polarized-Media (Electret Filter) |
| Smog | | Ionizer Purifiers |
| Pollen/Spores/ Allergens | | Thermodynamic Sterilization |
| Volatile Organic Compounds (VOC) | Gases | Activated Carbon Filter |
| Gaseous Oxides (Nitrogen, Sulphur, etc) | | |
| Carbon Monoxide (CO) & Carbon Dioxide ($CO_2$) | | Catalytic Oxidation |
| Free Radicals | | |
| Chemical Gases (Ammonia, Methane, Toxic metal compounds) | | |

Clean air systems (CAS) may also contain sensors and wireless communications to monitor the system, the surrounding environment, and the user. Wireless communications can be in the form of GPS, Bluetooth, Wi-Fi, cellular data networks etc. Utilizing the sensors and information obtained through the wireless communication may allow the CAS to provide reactive protection based on the data received. The CAS may also monitor the health and environment of the user.

Reactive protection may be provided by the clean air system (CAS). For example, a CAS may continually monitor in real time for pollutants such as those listed in Table 3. If the CAS determines a pollutant is present the system may inform the user. The CAS may also use the information received from the sensors to provide warnings to a user. Such warnings may be generated by a smart pollution warning system implemented on the CAS. The smart pollution warning system may use readings from a pollution sensor, such as a PM 2.5 sensor, to project or display the current or historical readings of the sensor on the device in a visible or audible fashion. As such, the user, as well as other nearby bystanders may be informed of the pollution levels in their environment. In another example, the CAS may trigger warnings to indicate that the air temperature and pollutant content of a user's current location could trigger a health condition, such as an asthma attack. Further, the system may alert the user to increase filtering intensity or swap filter cartridges for more effective filtering of the detected pollutant.

Alternatively, the CAS may automatically adjust filtration based on the sensor readings. The clean air system may contain one or more air quality sensors coupled with a controller in a feedback loop. The controller can be configured to set operation of the one or more filters in response to a signal from the one or more air quality sensors. For example, if the air quality sensors sense a large amount of pollen, the controller may determine which type of filter is effective at removing pollen. As a HEPA filter is effective at removing pollen, the controller may cause the CAS to start filtering air through a HEPA filter. Alternatively, the controller may notify the user that the pollen count is high and that a HEPA filter should be used. The CAS may also alert a user that they have been in a polluted area for too long and that they should seek cleaner, less polluted areas.

The controller may also be configured with a location sensor, such as a GPS sensor and wireless communications (e.g. a Wi-Fi antenna and module) to access online databases and information. For example, the controller may use the GPS to detect the location of a user. Based on location data the controller may access a database of known pollutants in the area using wireless communications. After the controller determines the location and the pollutants in the area, the controller may set operation of one or more filters of the CAS to remove said pollutants from the supplied air. Alternatively, the controller may not set the operation of one or more filters, but instead inform the user to set operation of one or more filters.

The controller may also access daily and regional weather and air quality forecasts using the wireless communications. Based on the received weather and/or air quality data, the controller may set operation of one or more filters to protect the user from inhaling any harmful particles. Further, the controller may set an intensity level for filtration. Alternatively, the controller may not set the intensity or operation of one or more filters, but instead inform the user to set operation or intensity of one or more filters. The received weather and/or air quality data may be updated as a user changes locations.

Health and environment monitoring of the user may also be performed by the clean air system. For example, the controller may be coupled with one or more user sensors configured to detect physiological data of the user. Such data may be heart rate data, perspiration data, temperature data, breath rate data, $O_2$ saturation data, etc. The sensors may be any one or more of a heart rate sensor, moisture sensor, thermistor, flow sensor, oximeter, etc. The physiological data from the sensors the data may be recorded and provided back to the user. Communication to the user may occur on the CAS or may be accessed through an online database on a computer or smartphone. Additionally, the physiological data may be communicated to an online database comprising a profile of the user. Accordingly, the user may access the database and review the information in their profile. Further, the feedback signals can be used to switch the CAS on and off if the user has fallen asleep or woken up, respectively. In some embodiments, the CAS is always on. In some embodiments the physiological data may be analysed to determine user illnesses. For example, user data captured while the user asleep may be analysed to determine sleep disorder breathing.

The CAS may also include an eye tracking sensor. The eye tracking sensor and a corresponding algorithm may be employed to monitor what a user is focusing on. The purpose of the eye tracking sensor is to locate the user's eyes which are facial landmarks to determine the direction of the user's head for adjustment of the nozzles. For example, if the user turns their head to look at something, the nozzle will adjust to maintain air direction alignment with the entrance of the user's airways.

Real-time pollution and location data from a network of similar systems can be collected and sent to a database. This collected information can be utilized to create a real-time pollution intensity map. The real-time pollution intensity can show what the pollution level is for a specific location. Further, the map may be used to alert other users of dangerous spots around them. The map may also help researchers understand pollution trends in certain areas.

A smart pollution navigation program may also be implemented on the CAS. For example, based on location and pollution data received from the sensors, the CAS may provide navigation data, similar to that of a traffic map, and give directions to users and/or travellers to avoid certain areas which have high pollution levels. In one example, the CAS may receive a destination from a user. The CAS may then direct the user with on screen or voice navigation to the destination, avoiding routes which would make the user travel through areas with high pollution levels. In some embodiments, the CAS may be connected to a user's smart phone, and the phone's GPS and navigation software may be used in conjunction with the CAS to provide directions to a user. In one embodiment the smart pollution navigation program may monitor a user's location, and provide them with a notification that they are nearing or within an area with high pollution. In another embodiment, when the location sensor identifies that the user is in an unfamiliar location, such as when travelling, it can bring up air pollution safety tips for the location and automatically sense the pollution content and concentration and adjust the filtering appropriately.

The real-time pollution monitoring may also be converted into an index within an online user profile. This index may inform the user of how much pollution they have been in and how much pollution they have avoided. Further, the index may be able to provide a user with knowledge of the different types of pollutants they were exposed to. Further, the index may inform the user the percentage of oxygen breathed in over a time period. A daily percentage of oxygen breathed in broken over hourly periods may be communicated to the user. Such information enables the user to see the effectiveness of protection the CAS offers.

The CAS may further include one or more sensors configured to detect orientation of a user flow interface and/or to detect wind direction and wind speed. For example the one or more sensors may include an anemometer to detect wind and an accelerometer to detect a user flow interface orientation. Based on the information from the anemometer and accelerometer a computer processor may be able to calculate the optimal air nozzle angle and/or position. Further, the computer processor may determine the best air flow strength to get the best ratio of cleaned air delivered to the user. The computer processor may be connected to a non-transient memory for storage of recorded data.

Based on the results calculated by the processor, the controller of the apparatus may adjust operation of the CAS. For example, based on the detected wind and/or orientation of the user flow interface the processor may determine a change in operation of the flow generator is necessary. Accordingly, the controller may cause the flow generator to change flow velocity. The processor may also determine that based on the wind and/or orientation of the user flow interface that the air nozzles within the user flow interface need to change position and/or change angles. Accordingly, the controller can cause the nozzles to adjust to get the best ratio of cleaned air to a user.

In some cases it may be difficult for a user to determine if the CAS is working as it should. Accordingly, the CAS can be configured to give feedback to the user about whether the CAS is working as it should. As shown in FIG. 14, the CAS may include an aromatic dispenser that is in line with the flow of air. If the aromatic dispenser is activated, the dispenser may release an aromatic recognizable scent 1301 into the flow of cleaned air 1302. The scent may indicate to the user 1303 that the CAS is working and providing cleaned air. Additionally, the scented air may be followed by the user to assure they are breathing in cleaned air.

Figure 38:
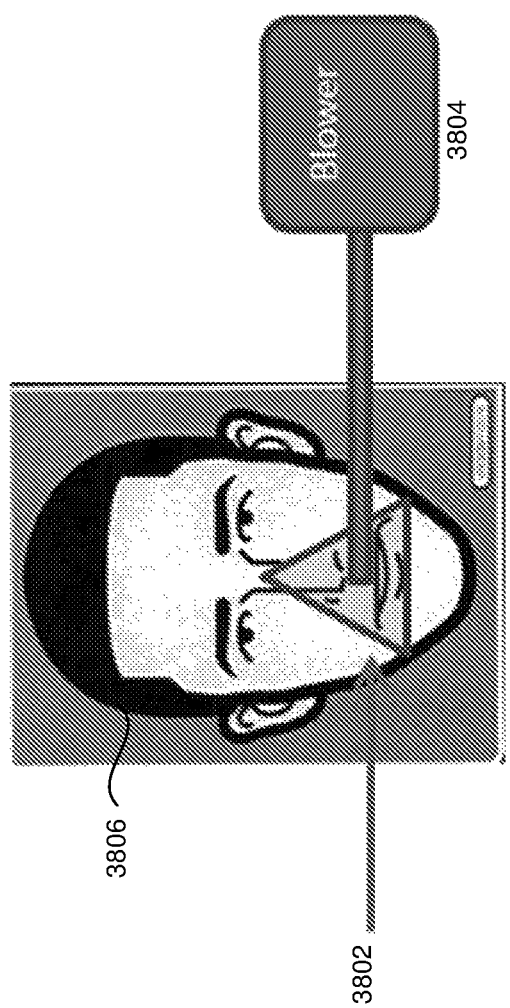
FIG. 38 is an illustration of a passive filter suitable for embodiments of the present technology.

In addition to, or as a replacement for the active Clean Air Systems described herein, a passive filter may be introduced to the system. For example, as shown in FIG. 38, a passive filter may be placed over the mouth and/or nose of a user 3806. By doing so, the blower 3804 of the CAS may be relieved of providing the entire amount of clean air to the user 3806 as the passive filter may supplement or replace the amount of clean air provided to the user. In some embodiments, if there is a low demand for the clean air filtering the blower 3804 may be turned off to conserve energy, and the user 3806 can rely on the passive filter 3802 for clean air. Further, the passive filter 3802 may provide a more comfortable experience to the user 3806, as the passive filter may provide sufficient air flow to the user without exerting excessive amounts of air to the user with a blower 3804.

The Clean Air System can be implemented as an integrated and connected system. In this regard, the CAS may mimic the connectivity of a fitness band or smart watch type device. As such, in addition to the providing clean air to the user, the CAS may be programmed to act like an extension of a smart phone. For example, the processor of the CAS may be programmed to communicate with a user's smart phone through a communications interface. The communications interface may be configured to receive and send signals from and to the smart phone through wired and wireless connections. Bluetooth, Wi-Fi, RF, cellular data networks, radio waves, etc., are example forms of wireless communications which can be used between the CAS and the smart phone.

Once a connection is established between the CAS and smart phone, a user may be able to send and receive SMS and MMS messages, as well as send and receive cellular phone calls. For example, the CAS may include a microphone(s), speaker(s), and/or headphone(s) where the user may communicate as if using a telephone. The CAS may also be programmed to recognize voice commands and to have camera capabilities, should a camera be installed within the CAS. As an integrated and connected system, the CAS device will be carried and/or worn by users most of the time, therefore increasing the likelihood the device is used, resulting in improved user health.

Air being directed to the nose and mouth of a user while they are speaking may distort the user's speech, dry the user's mouth, or otherwise make it uncomfortable to talk. To avoid such distortion and discomfort the CAS may include a speak mode. Speak mode may be implemented with the use of speech recognition software. The speech recognition software may enable the device to sense when the user is speaking and, in response, decrease or cease the supply of air to the mouth and nose while the user continues to speak. In some embodiments the speech software may automatically open up an exhaust valve, if present on the CAS, when the system detects a user is speaking.

The Clean Air System may also include other integrated intelligent health systems and features. For example, the CAS may include additional tracking capabilities to monitor usage and provide feedback to the user based on the usage of the CAS. Monitoring may be implemented through the use of sensors, such as pollution sensors, temperature sensors, physiological sensors, etc. The sensors may monitor the presence and concentration of pollution, such as those found in Table 3, at one or more locations. The CAS may also track the where and when the CAS was in operation. The monitored and tracked data may be stored in memory within the CAS system, or uploaded to a cloud based, or local, storage system.

The CAS may use the monitored information to provide feedback to the user. For example, based on the data collected the CAS may determine when and where the device was most beneficial, the number of hours the CAS was used, the amount of pollution removed from the user's breathing path (in grams, etc.,) filter efficiencies (i.e., how much particles and gases are being removed from the user's breaths), etc. The monitored and tracked data may be presented to a user in the form of graphs and charts containing the tracked measurements on a display of the CAS, or on a display of another device, such as a personal computer or smartphone. The monitored and tracked data may also be converted into an index within an online user profile. This index may be accessible by a user on the device or via another computing device, such as a smart phone or personal computer with a connection to the online profile.

The CAS may also include an exercise mode. The exercise mode may be activated manually by a user or automatically by the CAS. To automatically activate exercise mode the CAS may use data acquired from a collection of sensors, such as humidity data, air temperature data, flow data, and $CO_2$ concentration data. Once the received data indicates signs of exercise, such as an increase in relative humidity on exhalation breath, an increased minute ventilation, an increased exhale air temperature, etc., the device may automatically switch to exercise mode. Once in exercise mode the CAS, depending on its configuration, may activate an active exhaust valve. The exhaust valve may pull the user's exhaled air away. As exercise can also lead to an increased amount of $CO_2$ build up within interfaces which partially cover the user's mouth and/or nose may occur. Therefore, alternatively, or in addition to the active exhaust valve, an activated carbon filter can be introduced in exercise mode to decrease the $CO_2$ concentration. Further, while in exercise mode, the blower of the CAS may turn on or increase its output.

In some embodiments a cooling system can also be added to the CAS to cool down the inhaled air. Cooling system could be an additional valve with a blower and filter drawing cooler air from the environment. Alternatively, or in addition to the drawing cooler air from the environment, the CAS may include a Peltier chip which cools the air as it passes by the chip. The cooling system may be automatically started when the CAS switches to exercise mode, or manually activated by a user.

To assist users in reaching fitness goals, and to encourage use of the device, the CAS may provide breathing and/or usage targets. In this regard, the CAS may provide daily, monthly, yearly, etc., goals for a user of the device to strive for. For example, the CAS may provide a daily goal to use the device for two hours, or more or less. In another example, the device may direct a user to breathe at a target breathing rate for fifteen minutes, or more or less. Breathing and usage targets provide a feature which may be used to monitor respiratory health progress of the user (e.g., improvements in resting breathing rates.) The fitness goals, as well as progress towards these goals, may be included in an index within an online user profile. This index may be accessible by the user on the device or via another computing device, such as a smart phone or personal computer with a connection to the online profile. The fitness goals may be updated directly on the CAS or through accessing the user's online profile.

The CAS may also encourage proper or improved breathing by including an integrated inspiratory muscle training valve (IIMTV). In this regard, the CAS may activate the IIMTV when breathing training is requested. The IIMTV may require the user to reach a certain amount of inspiratory pressure prior to opening and allowing an inhalation of air by the user. In this embodiment, the CAS may be a sealed interface. Alternatively, the CAS may be an open interface and oxygen levels may be decreased to around 15% by increasing the percentage of other gas molecules such as nitrogen or carbon-dioxide, or lowering the air pressure so there are fewer air molecules per unit volume breathed in.

The CAS may further include one or more sensors configured to detect unintentional leaks in the system. For example, when a headgear such as a facemask is used to deliver air to a user, a seal should be maintained between the user and the mask for the device to maintain full effectiveness. When a sensor, such as a flow sensor, detects a leak between the mask and the user the device may inform the user that the mask should be tightened or replaced. Alternatively, the CAS may automatically trigger a tightening of a headgear through actuators in or mounted to the headgear when a leak is detected in an attempt to seal any leaks.

When first wearing a mask or other such flow interface, it may be difficult to get enough clean air into the mask because of the impedance present in the system. As such, a smart clean air ramp algorithm may be used by the controller. In this regard, the controller may be programmed to provide a maximum clean air flow to the flow interface, and then slowly ramp down the clean air flow once the user is comfortable with the level of clean air. A benefit of the configuration is that energy may be conserved as the blower does not operate at full speed for an extended period of time.

To further improve comfort for a user, an expiratory active valve (EAV) may be used to reduce the amount of $CO_2$ built up at a mask or other flow interface. In this regard, an EAV may be triggered to open upon the detection of a user exhaling. As such, the exhaled air will exit the clean air system, thereby removing the $CO_2$ immediately from the CAS, and reducing the stuffiness felt by the user. In some embodiments, the CAS may trigger the EAV to open when the $CO_2$ level at the user's mask is above a predetermined threshold value.

The integrated and connected CAS system may also sync with other integrated and connected CAS systems. By syncing multiple CAS systems together, users may monitor the usage of other user's devices within the synced group of devices. In this regard, each device may be assigned to a group, such as a group of family members, a group of friends, a group of colleagues, etc. Each CAS which is which is synced to a group may monitor the usage history of the other synced devices within the group. The usage history data which may be monitored may include the number of hours the device was used, breathing and/or usage targets, fitness targets, progress to achieving targets, exercise history, and other such information collected from sensors on the CASs.

In some embodiments the users of each device may be assigned an access level such as administrator, high, and base levels. Administrators may be able to control all of the features between synced CAS systems. As such, administrators may be able to control which devices may be added or removed from a synced group and the access levels of the users in the group. Administrators may also control what information users are able to share and/or monitor. For example, administrators may provide full access to monitor the shared information to users assigned to a high level, while limiting the data a base user may view and/or share. In one example, a group may include five family members including two parents and three children. Both parents may be given administrator level access, an older child may be given a high access level and the two younger children may be given a base access level. As such, the parents may monitor and control all of their children's usage. The older sibling, with a high access level, may be able to select what information he wishes to share and may monitor his two younger sibling's devices. The two younger siblings with base level access may only be able to view their own personal information and be blocked from viewing the other users in the family group.

In some embodiments where the CAS includes headphones or hands free talk devices, the microphone and headphone set can act as walkie talkie devices and connect with other clean air systems in proximity. Conversations may be enabled between all CAS devices within range or to only those assigned to certain synced groups, such as a synced group of family members.

In some embodiments the CAS may perform baby monitoring functions. For example, a CAS may be attached to a crib or placed in proximity to a baby. The information gathered by the sensors on the CAS monitoring the baby may be forwarded to a caretaker or uploaded to a storage location, such as a cloud storage location. The caretaker's CAS device may display the forwarded information, or the forwarded information may be accessed from the cloud storage with another computing device.

Figure 39:
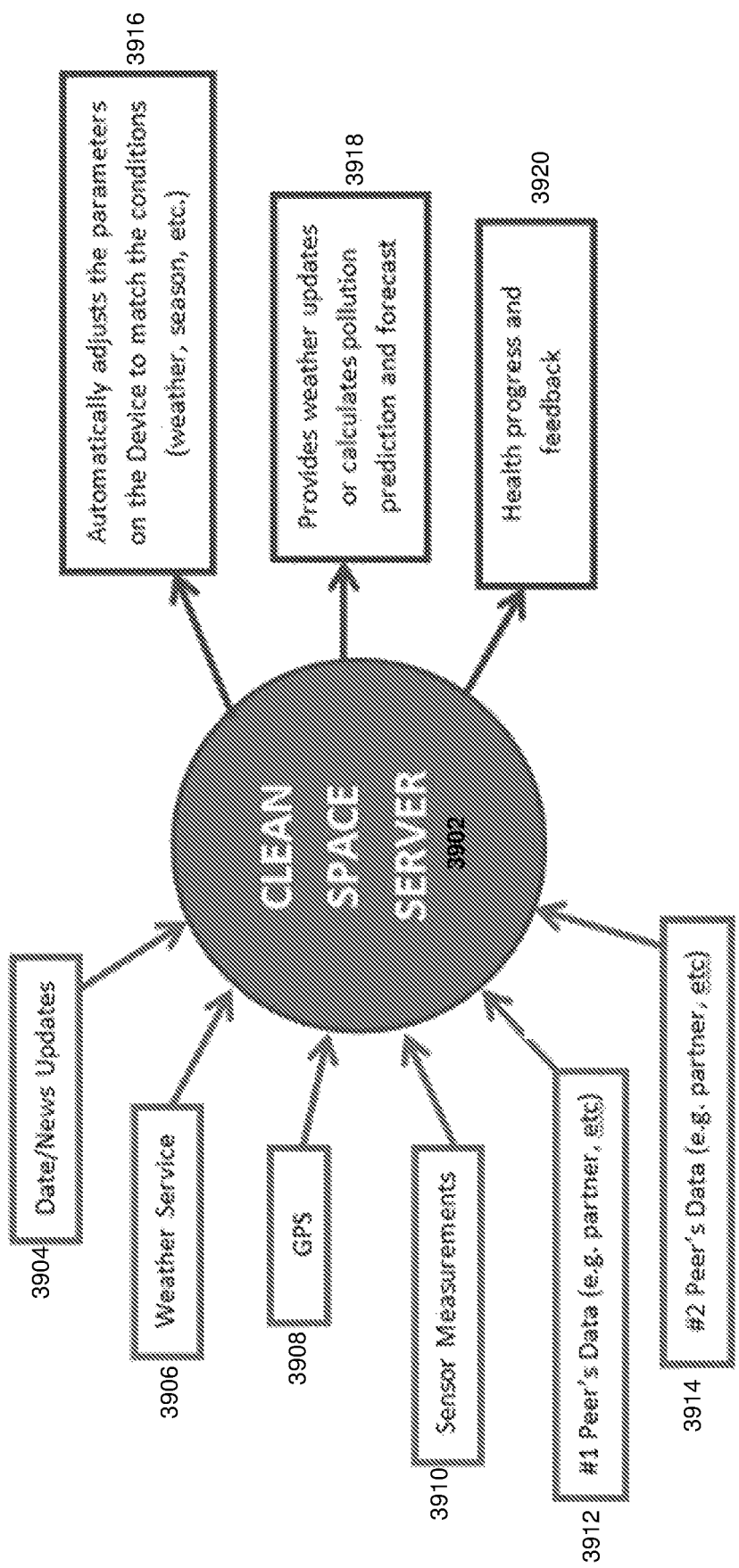
FIG. 39 is a block diagram illustrating a clean air server system suitable for embodiments of the present technology.

A clean space server may aggregate information and provide information to the CAS devices. For example, as shown in FIG. 39, a clean space server (CSS) 3902 may receive information from a variety of sources. Based on the received information, the CSS may send customised updates and reports to CAS devices, as well as automatically adjust operating parameters of the CAS devices.

The CSS may be comprised of one or more servers. The servers may be connected to one or more networks, such as a local area network (LAN) or the internet. The CSS may aggregate and store information from a variety of sources connected via the one or more networks. The information received from the variety of sources may include date, time, and news updates 3904, weather updates from weather services 3906, location information from GPS 1908 devices (which may be integrated into CAS devices), sensor measurements 3910 from CAS devices or from other sensors, CAS information from peer CAS devices 3912 and 3914 (i.e., member's CAS devices synced to a group).

From the variety of sources the CSS 3902 may from automatically adjust the parameters on specific CAS devices to match the weather conditions as shown in block 3916, provide weather updates or calculate pollution prediction and forecast as shown in block 3918, and provide health progress and feedback as shown in block 3920.

In one embodiment the CSS 3902 may use information received from the date, time, and news updates 3904, the weather service 3906, GPS 3908, and sensor measurements to adjust the operation of a CAS device. In this regard, based on received GPS signal 3908 and sensor measurements 3910 from the CAS device, the CSS may analyse the weather data received from weather service 3906 for a specific time and date received from the date, news, and time updates 3904 source. The CSS 3902 may then determine which parameters on the CAS should be adjusted to provide protection to the user based on the received information. In one example, the CSS 3902 may use the GPS of the CAS to detect the location of a user. Based on location data the CSS may access a database of known pollutants in the area at a certain time through the weather service 3906 or news updates 3904. After the CSS determines the location, time, and the pollutants in the area, the CSS may set operation of one or more filters of the CAS to remove said pollutants from the supplied air. Alternatively, the CSS may not set the operation of one or more filters, but instead inform the user to set operation of one or more filters.

The CSS may also access daily and regional weather and air quality forecasts using the weather service 3906. Based on the received weather and/or air quality data, the CSS may set operation of one or more filters to protect the user from inhaling any harmful particles. Further, the CSS may set an intensity level for filtration. Alternatively, the CSS may not set the intensity or operation of one or more filters, but instead inform the user to set operation or intensity of one or more filters. The received weather and/or air quality data may be updated as a user changes locations.

Sensory Entertainment Technologies

An air curtain system or other user flow interface can be implemented in an entertainment system to provide further sensory feedback to a user. Such an entertainment system may include some or all of the functionality as described in the air flow system, with our without air cleaning. However, the entertainment system may also include the controls to stimulate smell, touch, and/or taste senses, such as via the provided/generated air flow.

Figure 15:

As shown in FIG. 1 an entertainment system may include a flow generator 1603, smart clean air filtering 103, and a user flow interface 104. The flow generator may be any motor as described above and can include filters and sensors. If cleaning functionality is included, the entertainment system may be configured like a clean air system as shown in FIG. 14 with one or more filters. Dirty air 1401 may be pulled into a flow generator by first being passed through a pre-filter 1402. The pre-filter 1402 removes particles from the air which may damage the motor 1403. The motor 1403, as shown in FIG. 14, may then push the air through a primary filter 1404. The primary filter 1404 may remove unwanted particulates from the air. The filtered air may then be output to a user through a user flow interface 104 as cleaned air 1405. However, the entertainment system typically includes an additional sensory particle dispenser 1502, as shown in FIG. 15. In some embodiments the one or more filters may be replaced with scent cartridges that may be triggered in synchrony with an entertainment scenario (e.g., ocean waves cause a salty, ocean smell to be released from the scent cartridges into the air.) The entertainment system may further comprise a controller to control operation of the flow generator 1603. The controller may adjust the flow rate of the flow generator as well as air pressure generated by the flow generator.

The entertainment system may be able to connect to/communicate with various multimedia systems, such as televisions, DVD players, game/entertainment consoles, etc. through a communications interface. The communications interface is configured to receive entertainment signals from the multimedia systems through wired and wireless connection. Bluetooth, Wi-Fi, RF, cellular data networks, radio waves, etc., are example forms of wireless communications which can be used between the entertainment system and the multimedia systems.

The multimedia systems may be programmed to provide signals to the flow entertainment system. The entertainment medium being provided by the multimedia system, such as a movie, TV show, or video game, the user is using may have the 4D stimulation triggers programmed at different stages of the medium. These signals may be an indication of when to trigger the stimulation by the entertainment system. Such signals may also indicate the amount of stimulation and what type of stimulation should be provided. The signals are received by the controller and the controller may cause the entertainment system to provide the stimulation indicated within the signals such as by control of the flow generator and/or additional sensory feedback (e.g., smell, taste, tactile).

For example, while the user is watching a cooking show, a signal from the medium may be sent to the multimedia system. The multimedia system may then indicate to the entertainment system to release a strawberry scent from the additional sensory particle dispenser 1502, which corresponds to a strawberry being shown on the TV. In some embodiments, the release of a sensory particle into the air may result in the user tasting the sensory particle. For example, the entertainment system may release a sensory particle related to a strawberry which, when breathed in by a user, causes the user to smell a strawberry scent and taste a strawberry flavour. In another example, as a user is playing a video game the video game may indicate that the multimedia system should send a stimulation trigger to the entertainment system. The stimulation trigger may cause the entertainment system to release a smoke smell corresponding to a bomb which may have just exploded on screen from the additional sensory particle dispenser 1502.

The flow entertainment system can also use bio-feedback to trigger the stimulation. As described in regard to the CAS, above, such data may be heart rate data, perspiration data, temperature data, breath rate data, $O_2$ saturation data, etc. The sensors being used may be any one or more of a heart rate sensor, moisture sensor, thermistor, flow sensor, oximeter, etc. The 4D entertainment system may also include an eye tracking sensor. The eye tracking sensor may be on a user flow interface or may be a separate device. The eye tracking sensor and a corresponding algorithm running on a process may be employed to monitor what a user is looking at and focusing on Using the information received from the sensors, the flow entertainment system may be able to trigger stimulation or relaxing effects on a user. For example, a user who is watching a TV show may be starting to fall asleep. The eye tracking sensor may send a signal to the flow entertainment system that the user is falling asleep. In response to the received signal, the flow entertainment system may also provide a sleep enabler, such as releasing a lavender scent to calm the user and assist them in falling asleep easier. Continuing with this example, the eye tracking sensor may sense that a user has fallen asleep. Accordingly, the eye tracking sensor may send a signal to the flow entertainment system indicating that the flow entertainment system should be switched off or placed in standby power mode as the user is no longer using it. When the user wakes up, the eye tracking sensor may send a signal to the flow entertainment system to turn back on.

The controller of the flow entertainment system may also communicate the physiological data to a multimedia system. Accordingly, a user may be able to access their physiological data through the multimedia system. Further, the multimedia system may be able to utilize the physiological data to determine whether to send a flow stimulation trigger. For example, if a user's heart rate is rising while watching a horror movie, the multimedia system may send a stimulation trigger to the flow entertainment system indicating the heat of provided air should be raised to induce sweat.

The additional sensory particle dispenser 1502 may include an aromatic dispenser. The aromatic dispenser may be configured to selectively activate the release of aromatics from the aromatic dispenser into the cleaned air in response to a stimulation trigger being received by the flow entertainment system. The aromatic dispenser may house many small replaceable reservoirs or cartridges which hold perfumes. The perfumes may comprise smell and/or taste particles. These reservoirs or cartridges may be easily removed and replaced as new aromatics are needed or when the reservoirs or cartridges are depleted.

The aromatic dispenser may typically include electrical or mechanical mechanisms such as a pump or a thermo trigger to release the perfumes in small doses. The aromatic dispenser may release specific perfumes based on received stimulation triggers. For example a scene in a movie may include a scene where a character walks past a hotdog cart in the rain. The movie medium may contain an indication decoded by the multimedia system and sent as an entertainment trigger to the flow entertainment system. The entertainment trigger may cause the pumps or triggers with the aromatic dispenser to release a hotdog scent along with a rain scent. By allowing the user to smell what they are seeing they can be more immersed in the movie. In some embodiments, the flow entertainment system may blow the perfumes at a user's mouth and/or lips such that the user can taste the taste particles within the perfume.

The additional sensory particle dispenser 1502 may also include a droplet generator. A droplet generator may be used to inject droplets of liquid, such as water, into the cleaned air 1501 in response to a stimulation trigger being received by the flow entertainment system. The liquid droplets may be used to raise the humidity of the air being delivered to the user. For example, a scene in a movie may include a scene where a character is walking in the rain. The movie medium may send an indication to the multimedia system to send an entertainment trigger to the flow entertainment system. The entertainment trigger may cause the droplet generator to release droplets of water into the air signal raising the humidity and moisture of the air being sent to the user. The user may even then feel an imitation of the rain they are viewing in the movie. The droplet generator may house many small replaceable reservoirs or cartridges which hold one or more different liquids. The liquids may include smell and/or taste particles. These reservoirs or cartridges may be easily removed and replaced as new liquids are needed or when the reservoirs or cartridges are empty or depleted. In some embodiments the additional sensory particle dispenser 1502 may include an ultrasonic transducer, which may atomise droplets of liquid. The atomised droplets of liquid may then be released into the air signal.

The additional sensory particle dispenser 1502 may optionally include at least one heating or cooling element. The heating or cooling element may be used to change a temperature of the directed flow of air by having the directed flow of air pass by the heating or cooling element which is set to a specific temperature. The heating or cooling element may be used in response to an entertainment stimulation trigger being received by the flow entertainment system. For example, a video about arid deserts may carry a 4D signal indicating an air temperature of 40 degrees Celsius should be simulated and provided to the user. In another example, a video about Antarctica may carry a 4D signal indicating an air temperature of −20 degrees Celsius should be simulated and provided to the user. In a further example, the entertainment trigger may cause the droplet generator to release droplets of water into the air raising the humidity and moisture of the air, while at the same time decreasing or increasing the temperature of the air, to create a dreary atmosphere or humid atmosphere, respectively. The air may be directed towards the user's body, such as their chest, neck, face, etc., to increase the sensations.

When the additional sensory particle dispenser senses that cartridges or reservoirs of perfumes or liquids are empty, an indication may be sent to the user. The indication may appear on the 4D entertainment system, on the multimedia system, and/or within the user's online profile.

In addition to utilizing the additional sensory particle dispenser 1502 in response to entertainment/stimulation triggers, the flow entertainment system may control changes to the flow rate of the flow generator. Further, the flow entertainment system may adjust flow direction and location of the flow. For example, if a user is playing a video game and they are flying in an open helicopter, the flow entertainment system may receive an entertainment/stimulation trigger from the video game system. In response to receiving the stimulation trigger, the entertainment system may adjust the flow rate generated by the flow generator to a higher flow. Additionally, adjustable nozzles on a user flow interface may be mechanically aimed (e.g., with one or more electromechanical actuators) more directly at the user's face to simulate being in or near the helicopter, and to simulate the wind direction by selectively emitting flow from a combination of nozzles. Similarly, the flow entertainment system may be used in simulators, such as driving or flight simulators, to provide airflow at certain speeds based upon the speed of travel in the simulator. Further, the flow entertainment system may release certain scents based on the action within the simulators, such as the smell of burning rubber when tires spin on a car in the driving simulator. In other embodiments, the flow entertainment system may be used to mimic screenshots moving quickly in a multimedia medium, such as a movie or videogame. For example, as screenshots of a car driving are displayed, the entertainment system may output a flow of air to user to mimic the movement. Such flow output may be coupled with other multimedia signals, such as surround sound.

User Flow Interfaces (UI)

Various personal spatial respiratory interfaces (e.g., user flow interfaces) may be implemented in the system to direct air to the user. The user flow interface may allow cleaned air and/or air with sensory characteristics such as particles, scent, humidity, temperature, etc. to be delivered to the user's nose and/or mouth. The user flow interface 104 of an air curtain system, such as a clean air system 101 or flow entertainment system 102 may be hidden in or concealed by an item of clothing (e.g. scarf or turtle neck sweater). Alternatively, it may be camouflaged to visually appear like a fashion accessory rather than a medical device. The user flow interface 104 should not make unnecessary contact with the face or head, nor should it seal against the face. Accordingly, the user flow interface 104 should not limit the user's line of sight. Also, the user flow interface 104 should not be visually and/or acoustically detectable by third parties. By providing user flow interfaces in different forms, the interfaces may be emotionally unobtrusive, and therefore more acceptable for use in society.

Figure 16:
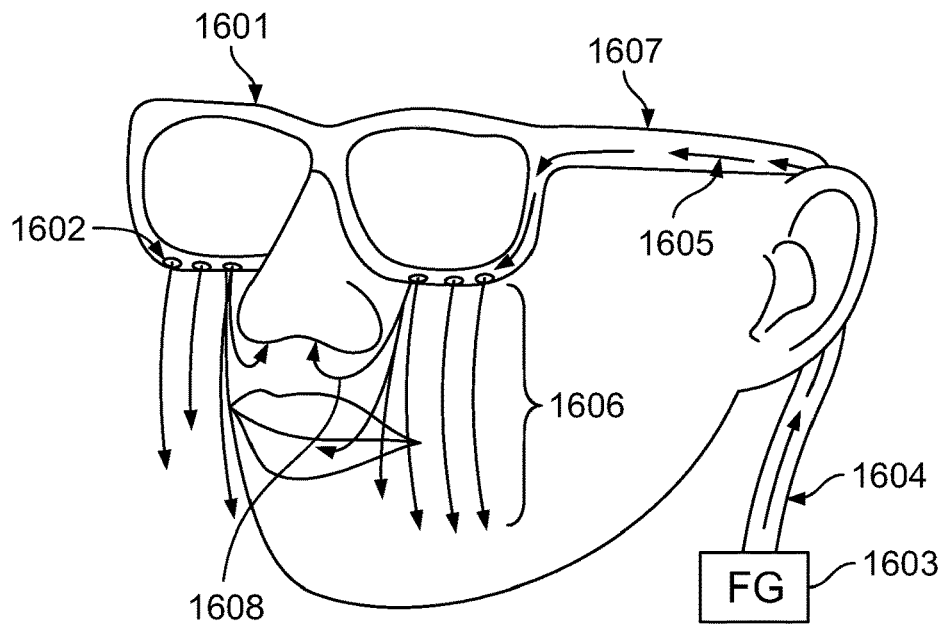
Figure 17:
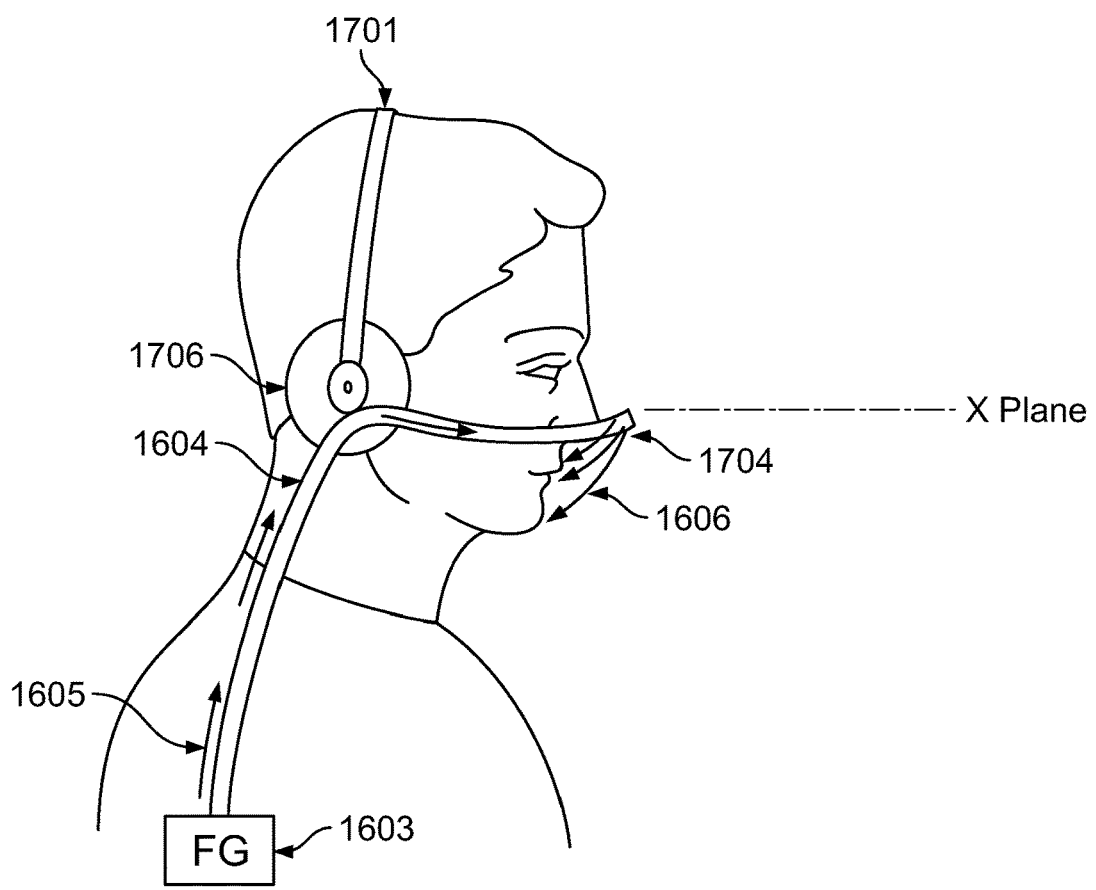

A possible user flow interface 104 is shown in FIG. 16. A pair of glasses 1601 or sunglasses may be used to channel air 1605 from a flow generator 1603. The glasses 1601 may connect to the flow generator 1603 using an air delivery conduit 1604. The air delivery conduit may channel the air from the flow generator 1605 into a tube which is on or within one or more of the arms 1607 of the glasses. The air 1605 may then travel through the tube to one or more holes 1602 positioned underneath the lenses of the glasses.

As the air 1605 flows out of the holes 1602, it may create an air curtain 1606 to the side of the nares and around the mouth of a user. The Coanda effect may assist in directing the air against the user's skin and therefore into the nares or mouth when a breath is taken. As such, when a breath is taken by the user, air from the air curtain 1606 may be directed into the user's nares, as shown by arrow 1608. As the air is being delivered underneath the eyes, no irritation of the user's eyes is caused by the air curtain 1606. While glasses are shown in FIG. 16, the user flow interface could be goggles, a visor, etc.

A headset may also be used as a user flow interface 104 for the delivery of air to the user may be achieved by channelling air 1605 from the flow generator 1603 into headset 1701 worn on the head of a user. The air may be carried through an air delivery conduit 1604 from the flow generator 1603 to a dispenser 1704 located at the end of the headset. The dispenser 1704 may release the air and create an air curtain in front of the user's mouth and/or nose. The headset may be worn over the head with the headgear or attached just on the ear with an earcup 1706. The direction of the air delivered may be below the x plane so the air is not directed into the eyes. Further, the headset may be placed in a horizontal plane across the nose so to not block vision of the user. The headset may be used for interactive video games, phone calls, or other activities normally performed with a headset while still delivering air. In some embodiments the flow generator 1603 may be positioned within the earcup 1706, with or without audio components. In this regard, the headset 1701 may be configured to appear as a working headset, but only operate as a flow interface.

Figure 18:
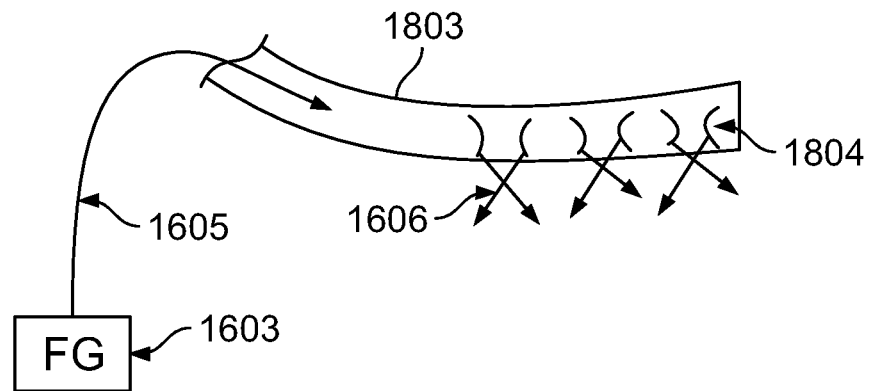

In certain embodiments of a user flow interface, the air delivery nozzles may be angled into each other in pairs. FIG. 18 shows pairs of air delivery nozzles 1804 which are delivering air 1606 from a flow generator 1603. The air from the flow generator 1605 may travel to the user flow interface 1803 and be released out the air delivery nozzles 1804. The air delivery nozzles 1804 direct the air 1605 so that paired streams may collide as they are released from the user flow interface 1803. When the air collides, it softens the impact of the air against a user's skin. This may allow for a more pleasant breathing experience. The air nozzle design shown in FIG. 18 may be utilized on many types of user flow interfaces contained herein in including a headset and glasses.

Figure 19:
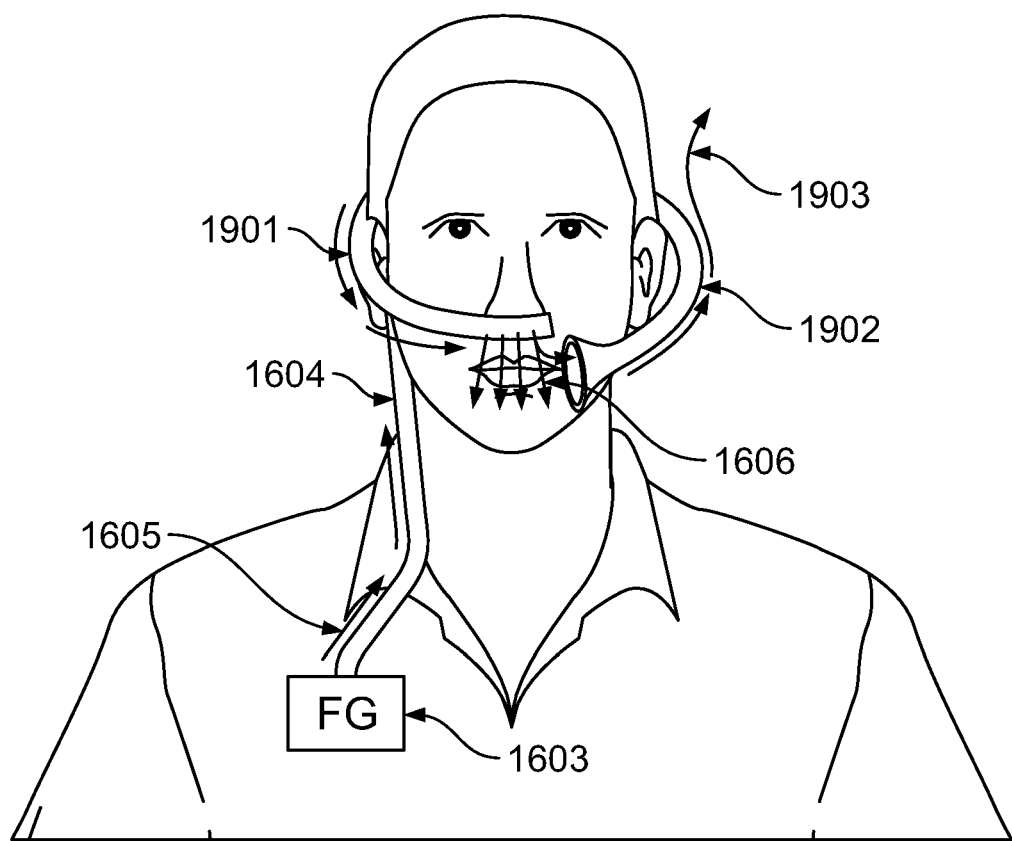

An exhaust may be utilized to remove air from around the user's nose and mouth. As shown in FIG. 19, an exhaust 1902 may be placed next to an air curtain 1606 being created by a user flow interface 1901. The air 1605 may be carried through an air delivery conduit 1604 from the flow generator 1603 to a dispenser at the end of a headset. The air from an air curtain 1606 may be sucked away from the user's breathing area by the exhaust 1902. This allows the system to get rid of scents, humidity, particles, etc. quickly than simply letting them dissipate away from the user. Accordingly, this may be useful in an entertainment environment where quick sensory changes may be necessary. While the exhaust 1902 shown in FIG. 19 is shown as being a headpiece, the exhaust 1902 may be any type of interface including glasses, hats, collars, etc. In some embodiments, the exhaust may be used to protect other individuals, or the user, from being exposed to germs or harmful airborne bacteria. In one example, when a sick user exhales, the exhaust may filter the exhaled air prior to releasing it into the atmosphere. As such, any germs which may be exhaled through breathing, sneezing, coughing, etc., from the sick user may be captured by the exhaust. Similarly, when the user is near other individuals the system may filter to remove airborne germs and/or bacteria prior to the air reaching the user.

Figure 20:
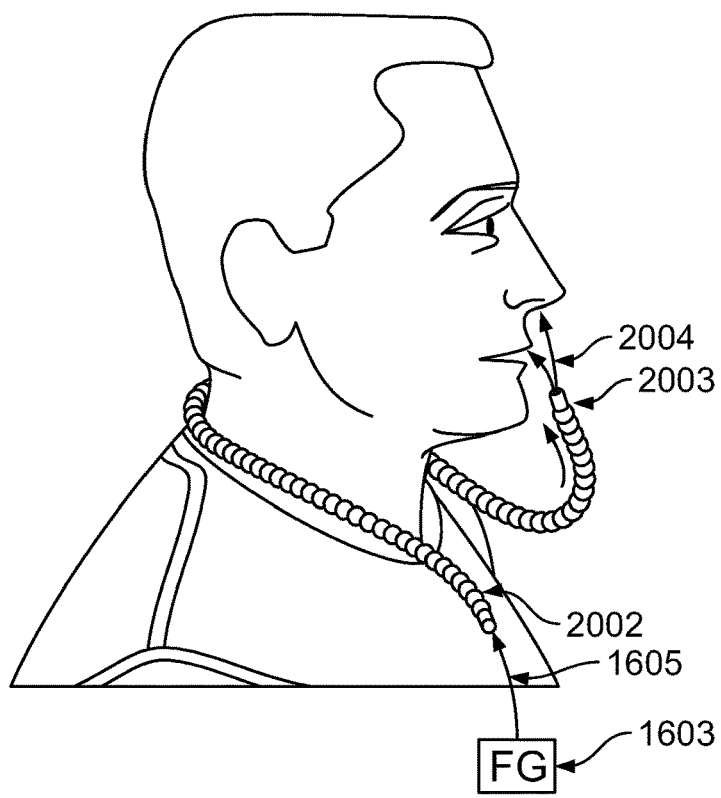
FIG. 20 is an example of a self-adjustable/repositionable goose neck for delivery of air suitable for some embodiments of the present technology.

A goose neck tube which sits off the face and around the neck and shoulders of a user, as shown in FIG. 20, may be used. The goose neck 2002 may receive air 1605 from a flow generator 1603. In one embodiment the goose neck may be self-adjustable and repositionable. Alternatively, a mechatronic system may be installed to automatically move the nozzle 2003 in response to a user's head movements. A head tracking or face tracking optical system may be installed within the system to locate the user's nose/mouth. As the tracking system tracks the user's nose/mouth mechanical actuators may make adjustment to the nozzle 2003 to target the airflow 2004 at the user's nose/mouth area.

Figure 21:
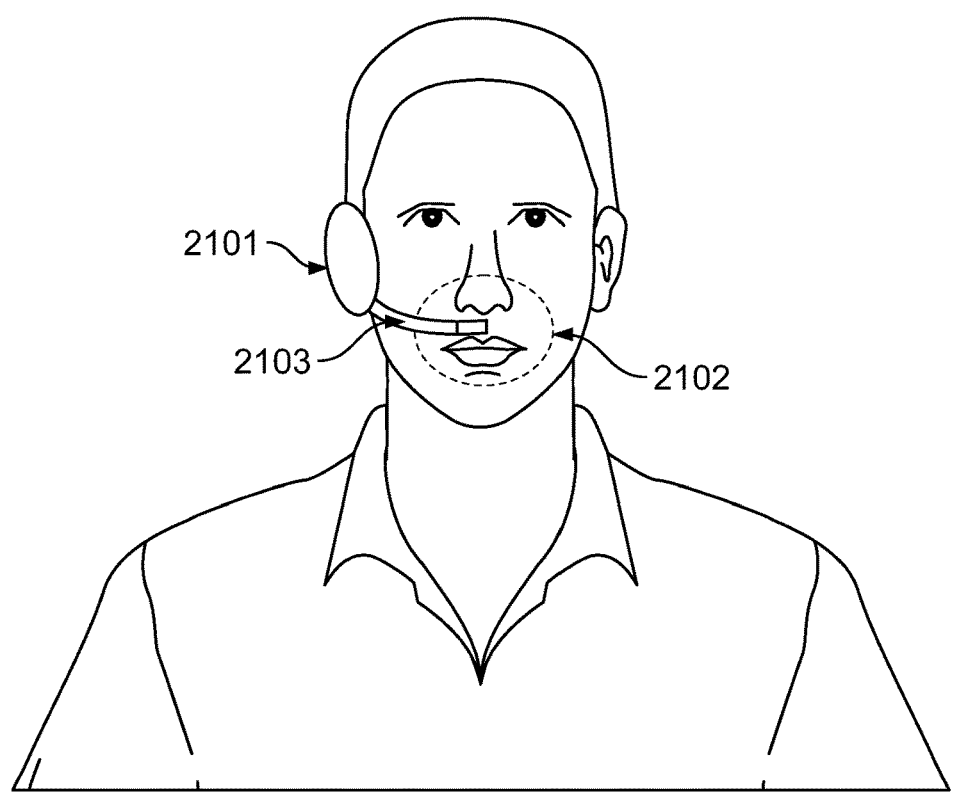
FIG. 21 is an example of a zone where delivery of air may be targeted suitable for some versions of the present technology.

The mouth and nose region may be the target area of the user flow interfaces. FIG. 21 shows the target region 2102 of a user utilizing a headset 2101 user flow interface 103. As the air is released from the arm 2103 of the headset it may be directed at the target zone. The target zone may be clear of the eyes and only around the mouth and nose to avoid irritation of the eyes. While the user flow interface 103 is a headset, any type of user flow interface may be used.

Figure 22:
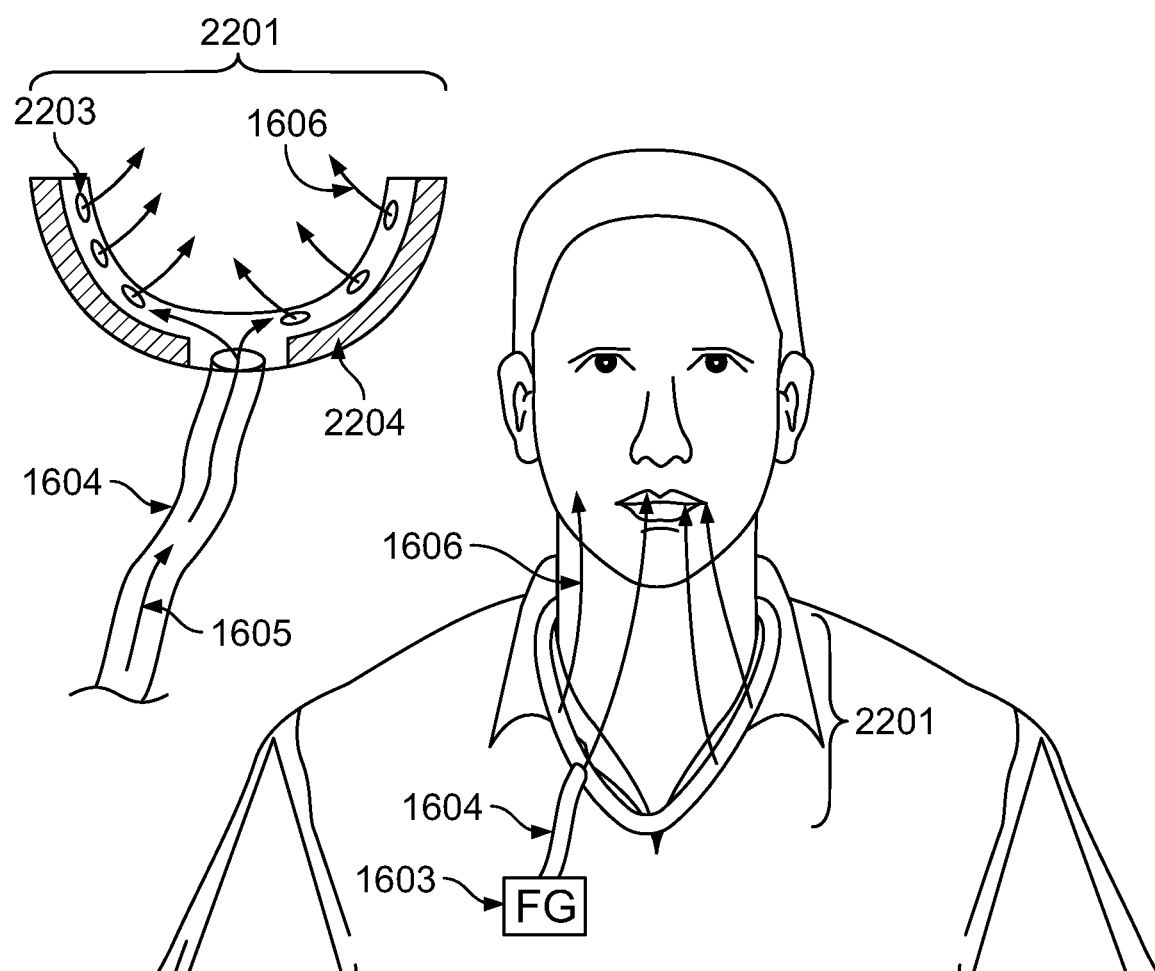
FIG. 22 is an illustration of a hidden cloth interface suitable for some versions of the present technology.

A hidden user flow interface which may be attached to clothing is shown in FIG. 22. The hidden user flow interface 2201 may be comprised of a thin tube structure ranging from about 1 cm to 5 cm in diameter and made from a soft material such as textile, silicone, plastic, etc. The hidden user flow interface 2201 may have nozzles 2203 for delivering an air curtain to a user. The hidden user flow interface 2201 may be designed to be hidden and attached to the inside of a shirt or blouse, etc. The hidden user flow interface may be camouflaged into clothing or may be embedded into clothing. The hidden user flow interface 2201 may be held in place under the collar of the shirt with adhesives, mechanical clips, or sewn into the fabric of the shirt. The air 1605 delivered to the hidden user flow interface is via an air delivery conduit 1604 from the flow generator, which may be hidden under or within the shirt, worn on a belt, attached with an armband or secured in some way to the user. An air curtain 1606 may then be delivered up towards the nose and mouth of the user. The Coanda effect helps bring the flow along the skin and into the nose and mouth of the user. In this regard, the air curtain 1606 may follow the curves of the user's face, including the user's neck and chin, to flow up towards the nose and mouth of the user.

Figure 23:
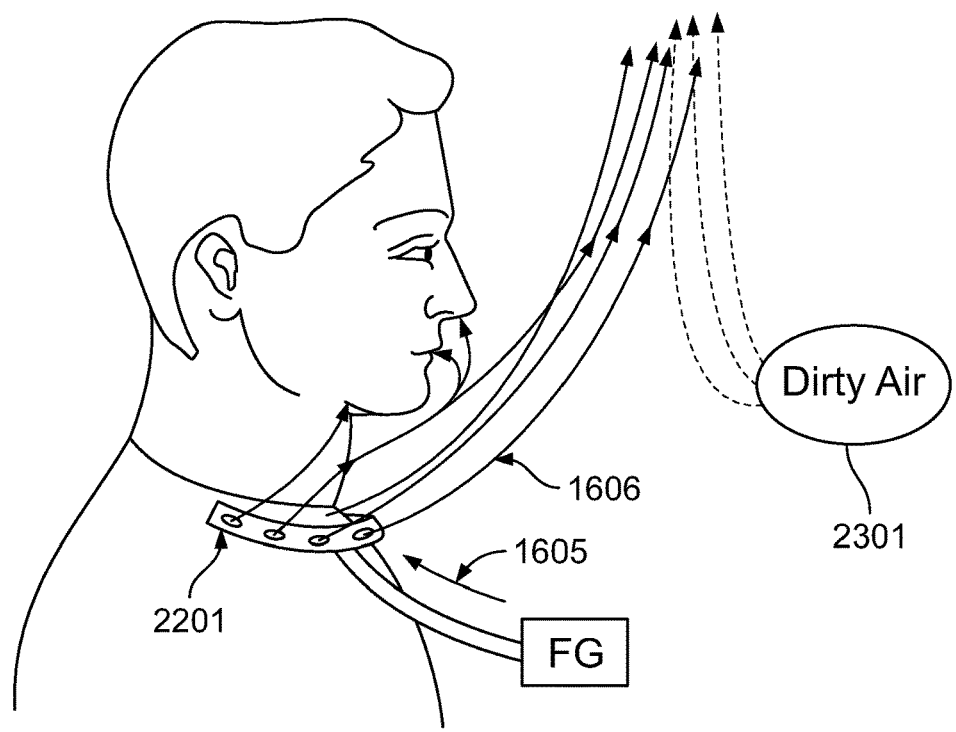
FIG. 23 is a side view of a hidden cloth interface suitable for some embodiments of the present technology.

The air curtain 1606 from the hidden user flow interface 2201 may be directed up and away from a user's face as shown in FIG. 23. The stream is not directed into the user's face so no discomfort is cause. Further, the upward air stream may create a fluid barrier or separation barrier between the dirty air 2301 and the cleaned air 1605 being breathed in. As the cleaned air 1605 is sent towards the user in an air curtain 1606 entraps dirty air 2301 and directs it away from the user. The user may then breathe in only the desired cleaned air towards the end of the air curtain 1606. In some embodiments the cleaned air may contain scents, particles, etc., which may be added or introduced into the cleaned air by an air curtain system. This may indicate to the user that cleaned air is being breathed if the scent is detected. To avoid olfactory fatigue, the CAS may change the scent periodically in order for the user to avoid getting desensitized to the same scent. The direction of the air curtain 1606 may be adjusted manually, or alternatively, may be permanently set into a specific direction.

Figure 24:
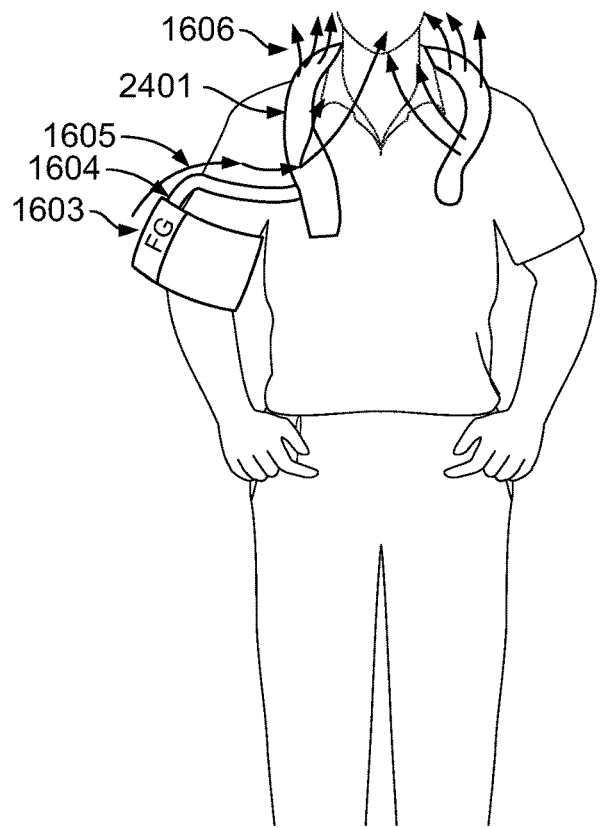
FIG. 24 is an illustration of a hidden cloth interface housed within a scarf suitable for some versions of the present technology.

A user flow interface 104 may be in the form of a scarf. In FIG. 24, a scarf 2401 housing a delivery interface is shown. This scarf is draped around the users shoulder and delivers air to the user in a similar fashion to the user flow interface under the collar. By putting the delivery interface within the scarf 2401, it is possible for the scarf to remain a fashionable item, which would not appear to be a medical device to a third party. As shown in FIG. 24, a flow generator 1603 may be attached by an arm band to the user's arm. An air delivery conduit 1604 may carry air 1605 to the user flow interface. The user flow interface may deliver an air curtain to the user 1606. The interface may be a closed loop semi-moulded to the contour of the user's body. This allows the user an easier set up the next time they want to wear it. The material of the user flow interface can also be made from a low temperature TPE. As the user wear's the scarf, the TPE may mould itself to the user's contour through the use of the user's body heat.

Figure 25:
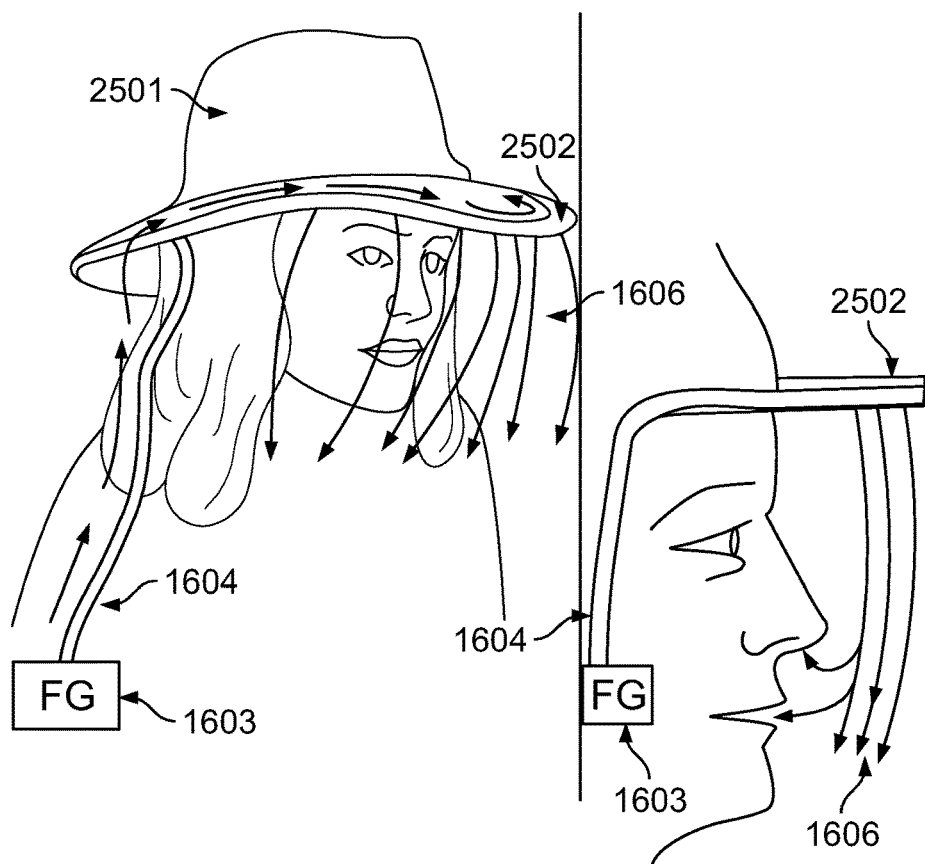
FIG. 25 is an illustration of a user flow interface including a hat for delivery of air suitable for some embodiments of the present technology.

FIG. 25 shows a user flow interface 104 in the form of a hat 2501. The hat 2501 may be connected to a flow generator 1603 by an air delivery conduit 1605. On the brim of the hat may be holes which direct an air curtain 1606 down across the user's face. Having the air curtain flow down across the user's face is based on the same principles as the collar embodiment above, but reversed.

Figure 26:
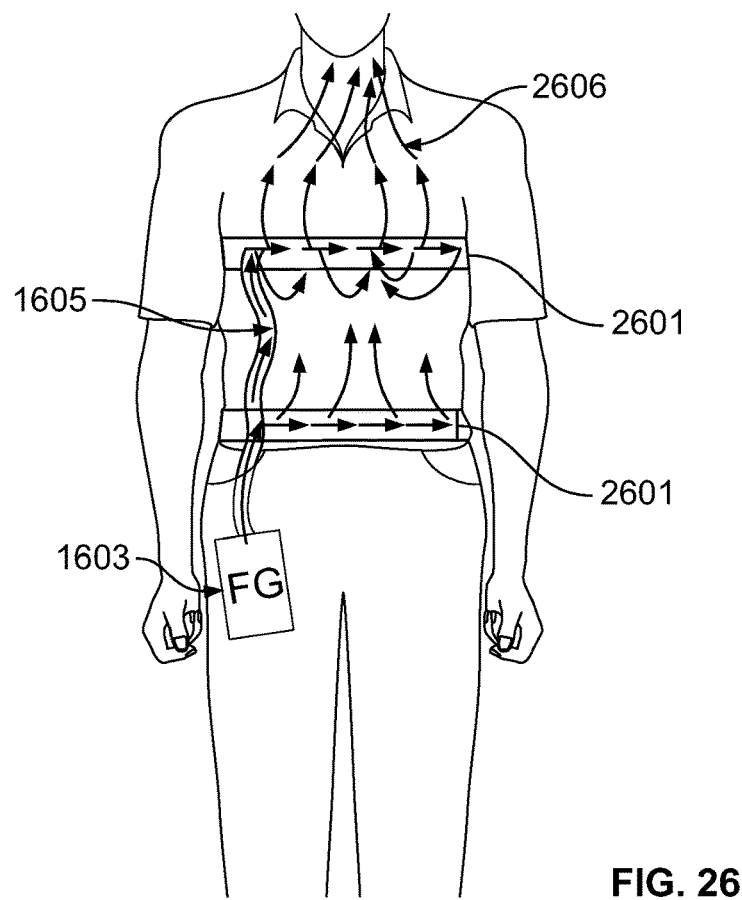
FIG. 26 is an illustration of a user flow interface including a strap for delivery of air suitable for some embodiments of the present technology.
Figure 27:
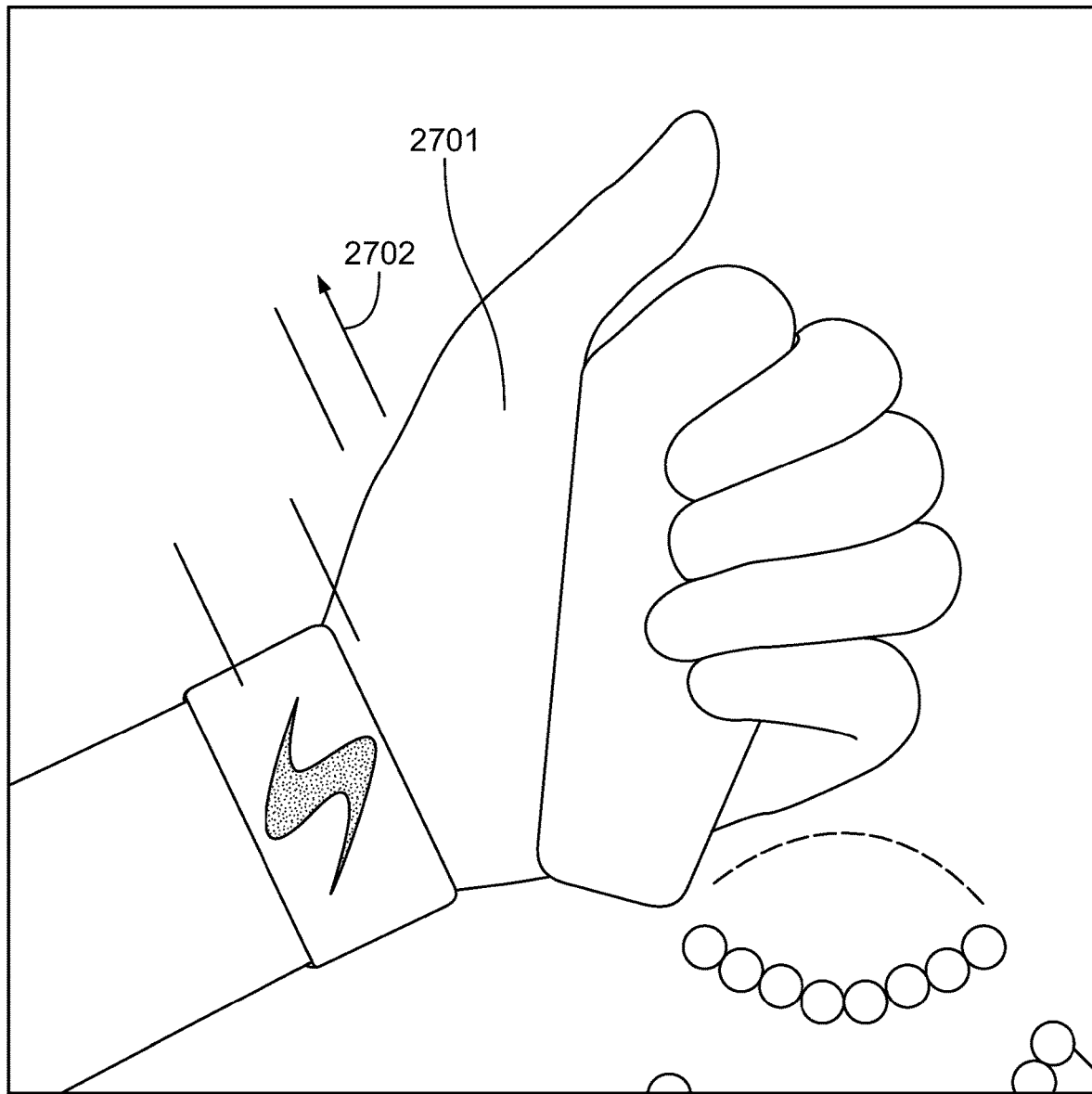
FIG. 27 is an illustration of a user flow interface including a glove suitable for some embodiments of the present technology.

A user flow interface 104 may be in the form of a strap or straps 2601 which can be worn across the top of the chest or anywhere below the waist as shown in FIG. 26. In this embodiment, air 1605 from a flow generator 1603 may be forced through the shirt and may escape at the top of the collar to provide air 2606 to the user. The air may carry deodorant to reduce body odour at the same time.

Figures 40A, 40B, 40C:
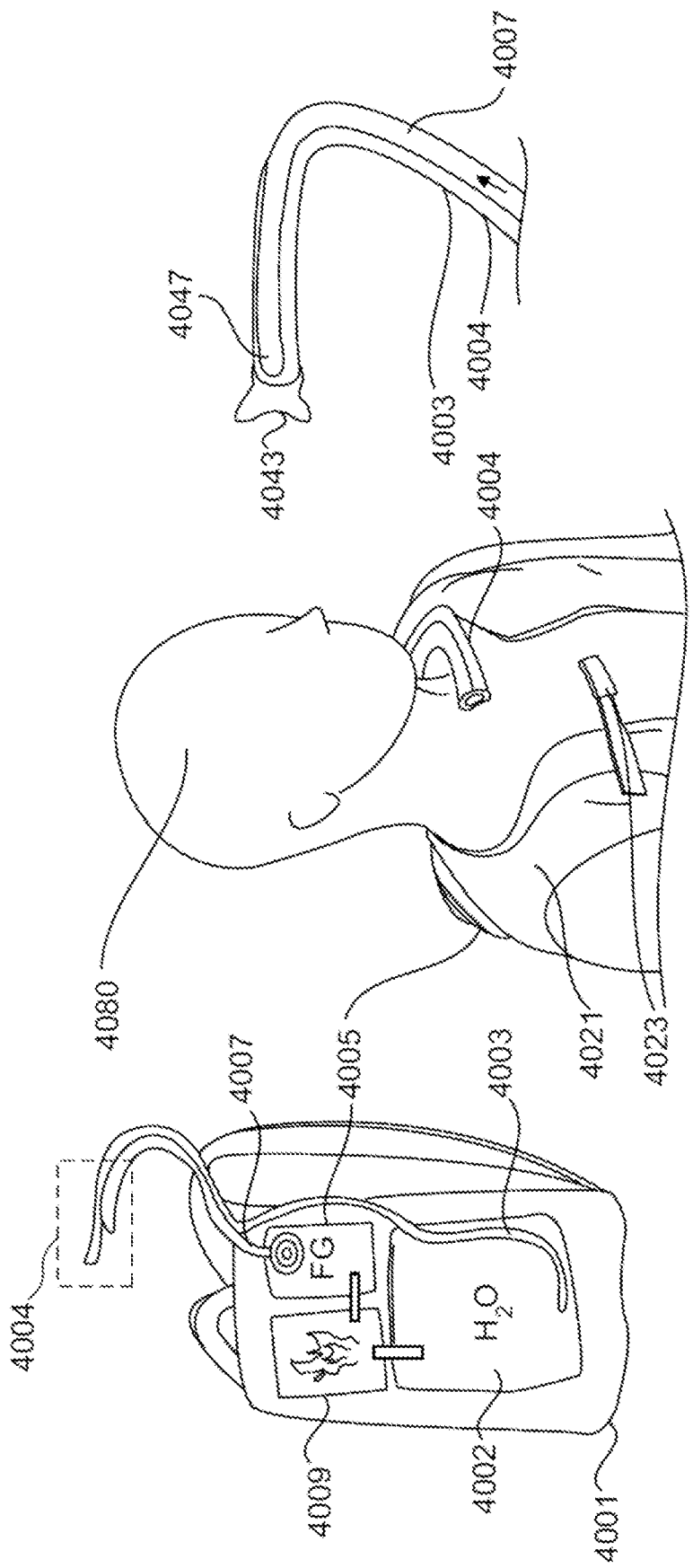
FIGS. 40A-40C illustrate a user flow interface including a hydration back pack suitable for some versions of the present technology.

FIG. 40A shows a user flow interface 104 in the form of a hydration backpack 4001. The hydration backpack 4001 may contain a water pack 4002 for delivering water to a user via water conduit 4003 to a dual interface 4004. The hydration backpack may also include a flow generator 4005 for delivering clean air via an air delivery conduit 4007 to the dual interface 4004. The hydration backpack 4001 may also include a humidifier 4009 for humidifying the clean air delivered by the flow generator 4005. In this regard, the humidifier 4009 may draw water from the water pack 4002 and one or more heating elements within the humidifier may vaporize the water. The flow generator may pass the cleaned air through the vaporized water, thereby adding humidity to the cleaned air. In other embodiments, humidity can also be introduced to the system via a separate water wick cartridge.

As shown in FIG. 40B, the hydration backpack 4001 may be carried on the back of a user 4080. The hydration backpack 4001 may include shoulder straps 4021 and a chest strap 4023 for securing the strap onto the back of the user 4080. When the hydration backpack 4001 is worn on the user's back, air located behind the user may be drawn into the flow generator 4005. The dual interface 4004 may wrap around from the user's back to below the user's chin. The position of the dual interface 4004 may be adjustable. For example, the water and air delivery conduits, as well as the dual interface 4004 may be semi-rigid, allowing the conduits and dual interface to be positioned in front of the user's mouth and nose when delivery air and at the user's mouth when the user requires a sip of water.

The dual interface 4004, as shown in FIG. 40C, may include delivery mechanisms for delivering both water from the water pack 4002 and cleaned air from the flow generator 4005. In this regard, the air delivery conduit 4007 and water conduit 4003 may be connected together at the dual interface 4004. The dual interface 4004 may include a mouthpiece 4043 from which a user may sip water from the water pack 4002 via the water conduit 4003. The dual interface may also include an air nozzle 4047 which may direct cleaned air received via the air delivery conduit 4007, as an air curtain across the user's face. In some embodiments, a head tracking or face tracking optical system may be installed within the system to locate the user's nose/mouth. As the tracking system tracks the user's nose/mouth mechanical actuators may make adjustment to the air nozzle 4047 to target the airflow at the user's nose/mouth area.

Figure 41:
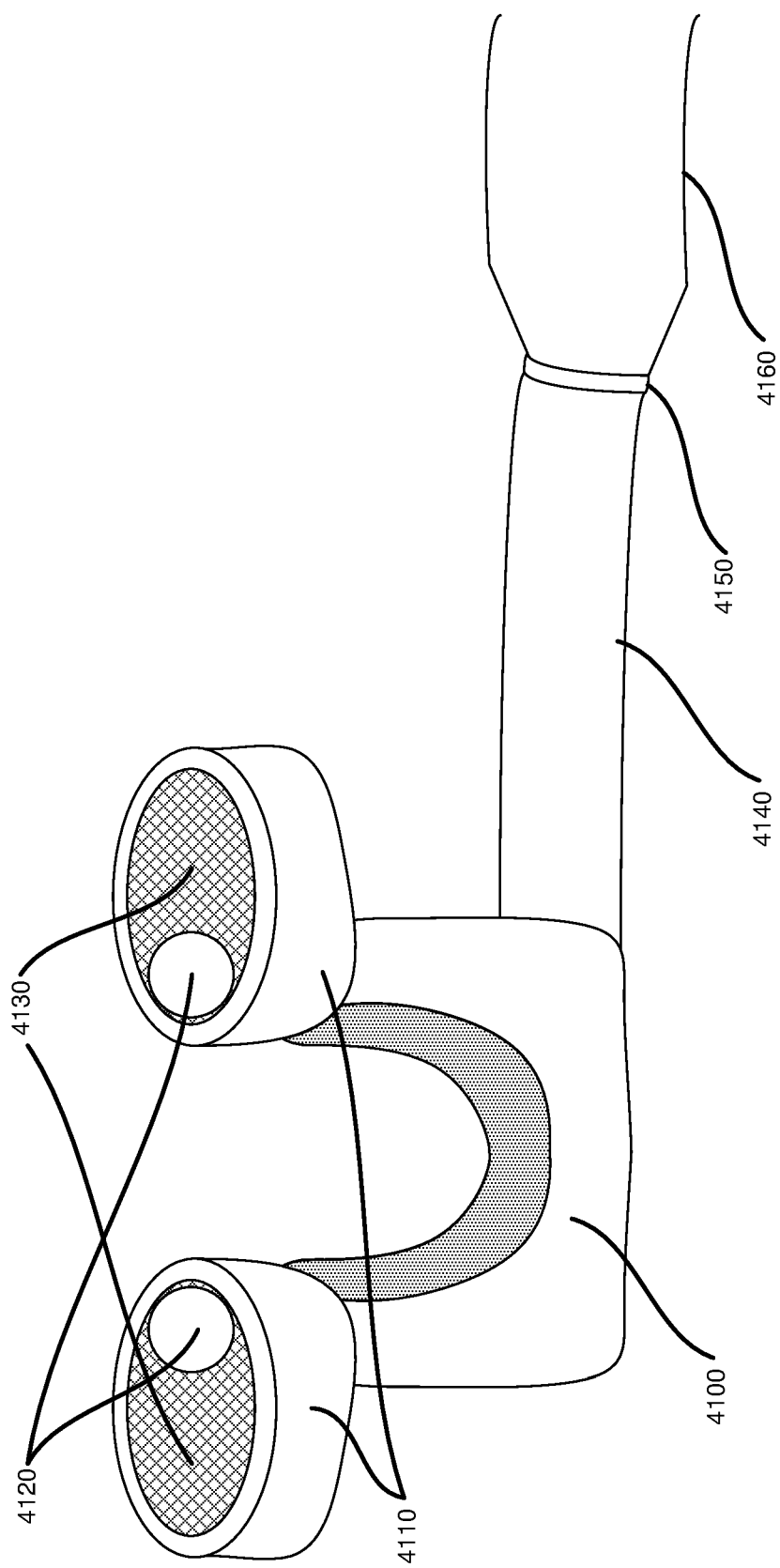
FIG. 41 is an illustration of a user flow interface including a nose clip suitable for some versions of the present technology.

The user interface may be in the form of a nose clip 4100, as shown in FIG. 41. The nose clip may be comprised of two rigid rings 4110 which are configured to fit within the nares of the user. The rigid rings 4110 may form a seal with the user's nares, preventing air from leaking around the rigid rings and into or out of the user's nose. The rigid rings 4110 may contain clean air nozzles 4120 and a pollution filter 4130, and/or a heat moisture exchange (HMX0 filter for breathing comfort. The clean air nozzles may direct clean air provided from a flow generator into the user's nasal passages. The pollution filter may allow the user to breath in air from outside of the system, as well as allow exhaled air to exit the system. The pollution filter 4130 may also block pollution or other airborne objects from entering the user's nares when the user inhales.

The nose clip 4100 may include a connection tube 4140 for connecting the nose clip to a conduit 4160 which may deliver clean air from a flow generator. A connector 4150 may be used to join the connection tube 4140 to the conduit 4160. The nose clip 4100 and connection tube 4140 may be manufactured from lightweight, low density, clear material. For example, the nose clip 4100 and connection tube 4140 may be manufactured from a lightweight plastic material which may assist in reducing the inertia and momentum of the device when the user in moving, such as when the user is exercising. Likewise, the conduit may also be manufactured from a material which is rigid enough to hold its shape, but soft enough to follow the movements of the user's body. The nose clip 4100 and connection tube 4140 may be separable, thereby enabling either piece to be replaced and/or replenished. In another embodiment, the connector 4150, connection tube 4140, nose clip 4100, rigid rings 4110, nozzles 412, and filter 4130 are consumable items intended to be replenished and replaced.

Figure 42:
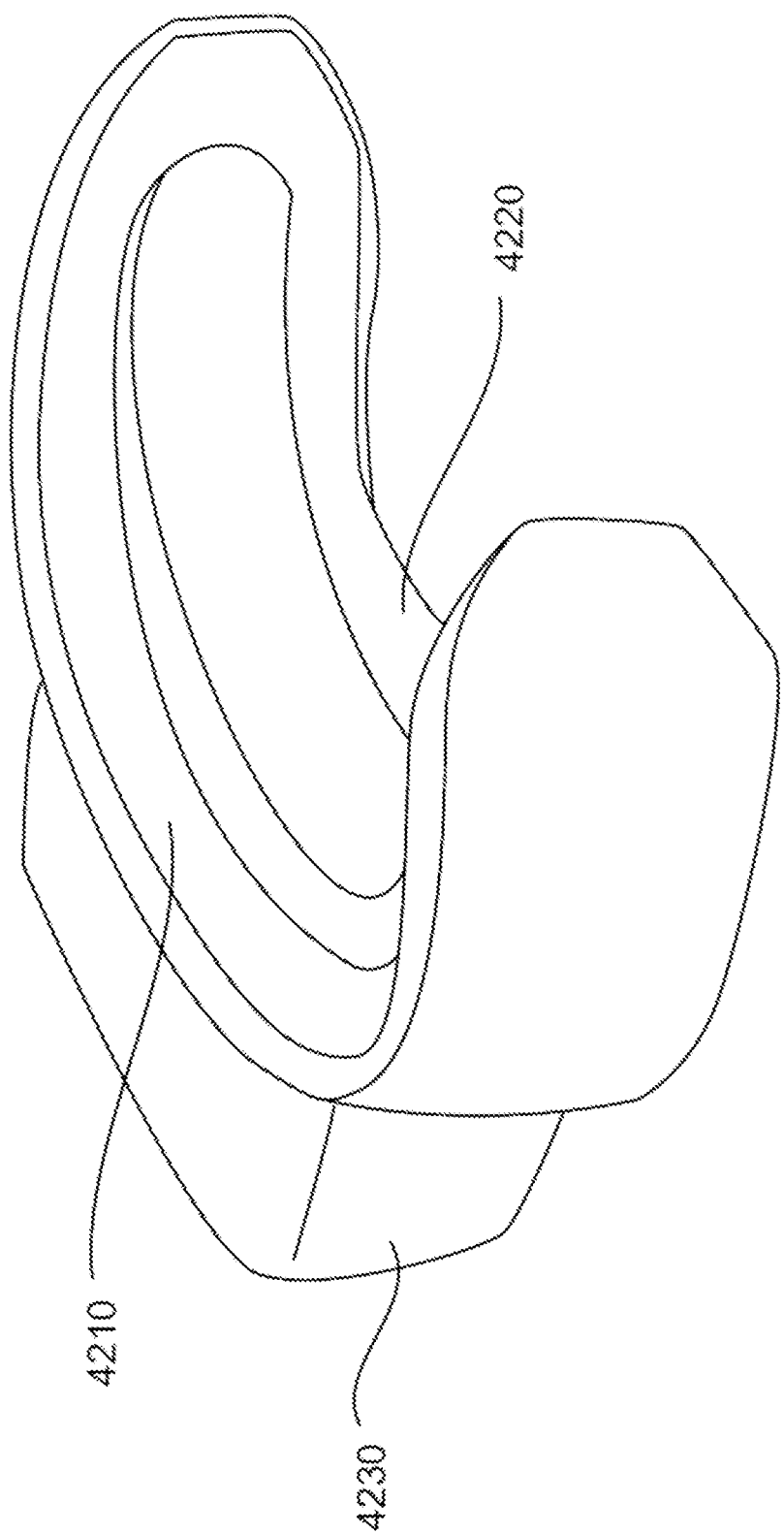
FIG. 42 is an illustration of a user flow interface including a mouth piece suitable for some versions of the present technology.

The user interface may be in the form of a mouth guard, as shown in FIG. 42. The mouthguard may be comprised of a top mouth piece 4210, a bottom mouth piece 4220, and a filter 4230 positioned between the top mouth piece and bottom mouth piece. The top mouth piece may be held between the top teeth, lips, and gums of a user, and the bottom mouth piece may be held between the bottom teeth lips, and gums of the user. The filter 4230 may be any type of filter, such as an air pollution filter. In one embodiment, the filter 4230 is not positioned within the patient's mouth and is exterior of the mouth to avoid contact with the patient and avoid contamination by the particles trapped in the filter 4230. The filter 4230 is detachable and is a consumable item intended to be replenished and replaced. The mouthguard may provide oral pollution protection when a user breathes through their mouth. For example, during times of heavy exertion (e.g., exercise,) a user may tend to breathe through their mouth. The filter in the mouthguard may protect the user from pollution and/or other airborne bacteria during these times. In some embodiments the mouthguard may be used in conjunction with other interfaces, to provide extra oral protection against pollution and/or other airborne bacteria.

A user flow interface 104 may be in the form of a sport band. As shown in FIGS. 43A and 43B, the sport band 4301 may wrap around a user's head 4320. At the back of the sports band 4301 may be a housing 4305 for positioning a flow generator, humidifier, batteries, and other blower components within the band of the sports band 4301. In some embodiments an air conduit may connect an external blower and the sport band 4301, allowing the blower components to be removed from the sports band. In the front of the sport band 4301 an air nozzle 4303 may be positioned. Turning to FIG. 43B, the sport band may be positioned to rest on the user's ear 4322. In this regard, the weight of the housing 4305 may pull the sport band downward onto the user's ear 4322, allowing the air nozzle 4303 to be elevated off of the user's face, in front of the user's mouth and/or nose.

A user flow interface 104 may be in the form of a sliding mask. As shown in FIG. 44, the sliding mask 4400 may have a movable front plate 4410. The moveable front plate 4410 may be moved to the side of the mask to create an opening to the user's mouth and/or nose, as shown by arrows 4420. Such an opening may be convenient for when a user desires to eat or speak. The moveable front plate 4410 may be moved manually or automatically with actuators. The sliding mask 4400 may include a passive filter for providing passive protection from pollution and other elements. In some embodiments the sliding mask may include a nozzle for delving clean air received from a flow generator.

For interfaces suitable for the entertainment field, the user flow interface (e.g. an entertainment interface) may be taken away from the head and face. Most entertainment devices and consoles require a controller. The user flow interface can be embedded into this controller and the extra sensory elements added within. Further, the user flow interface 104 may be a glove 2701. Air 2702 may be released from the glove 2701. The air may include scents and small particulates as described above. The scents and small particulates may be distributed from inbuilt smell cartridges within the glove.

Figure 28:
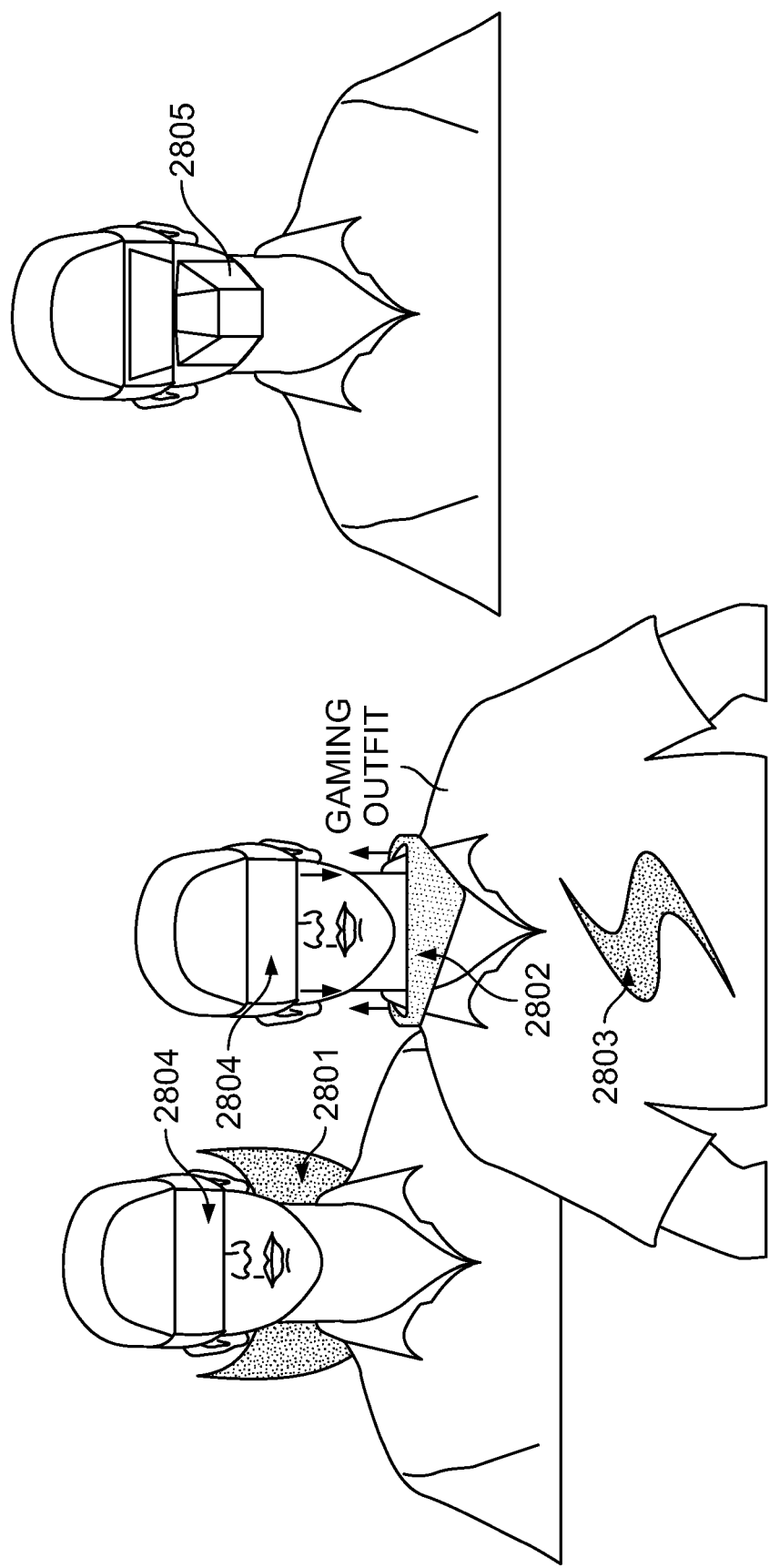
FIG. 28 is an illustration of a user flow interface including a collar, shirt, goggle, and mask suitable for some versions of the present technology.

Entertainment interfaces may come in the form of clothing as well. For example, as shown in FIG. 28, air interfaces can be collars 2801 and 2802, goggles 2804, shirts 2803 and masks 2805. In some embodiments, air may be sent up from a collar 2801 and 2802 and down from a visor 2804. The entertainment interfaces may also enable the system to trigger other sensory effects, such as squeezing the user, heating and cooling the user, and getting the user wet. In some embodiments the entertainment interfaces may be attached to other users or to inanimate objects, such as chairs, desks, beds, etc. In one example, the entertainment device may be worn by a user to an individual's left. When triggered, the entertainment device may blow air, or another sensory effect, in the direction of the individual, resulting in the sensation be felt by both the user and the individual. Similarly, when the entertainment device is attached to an object, such as a chair, the air or other sensory effects may be provided to more than one individual based.

The user flow interface 104 may be configured as a mock e-cigarette. In this regard, the mock e-cigarette may mimic the appearance and operation of an actual e-cigarette. For example, a passive filter and/or flow generator may be placed within the mock e-cigarette. When a user of the user inhales on the mock e-cigarette, instead of delivering smoke, the mock e-cigarette may deliver cleaned air from the flow generator.

Figure 29:
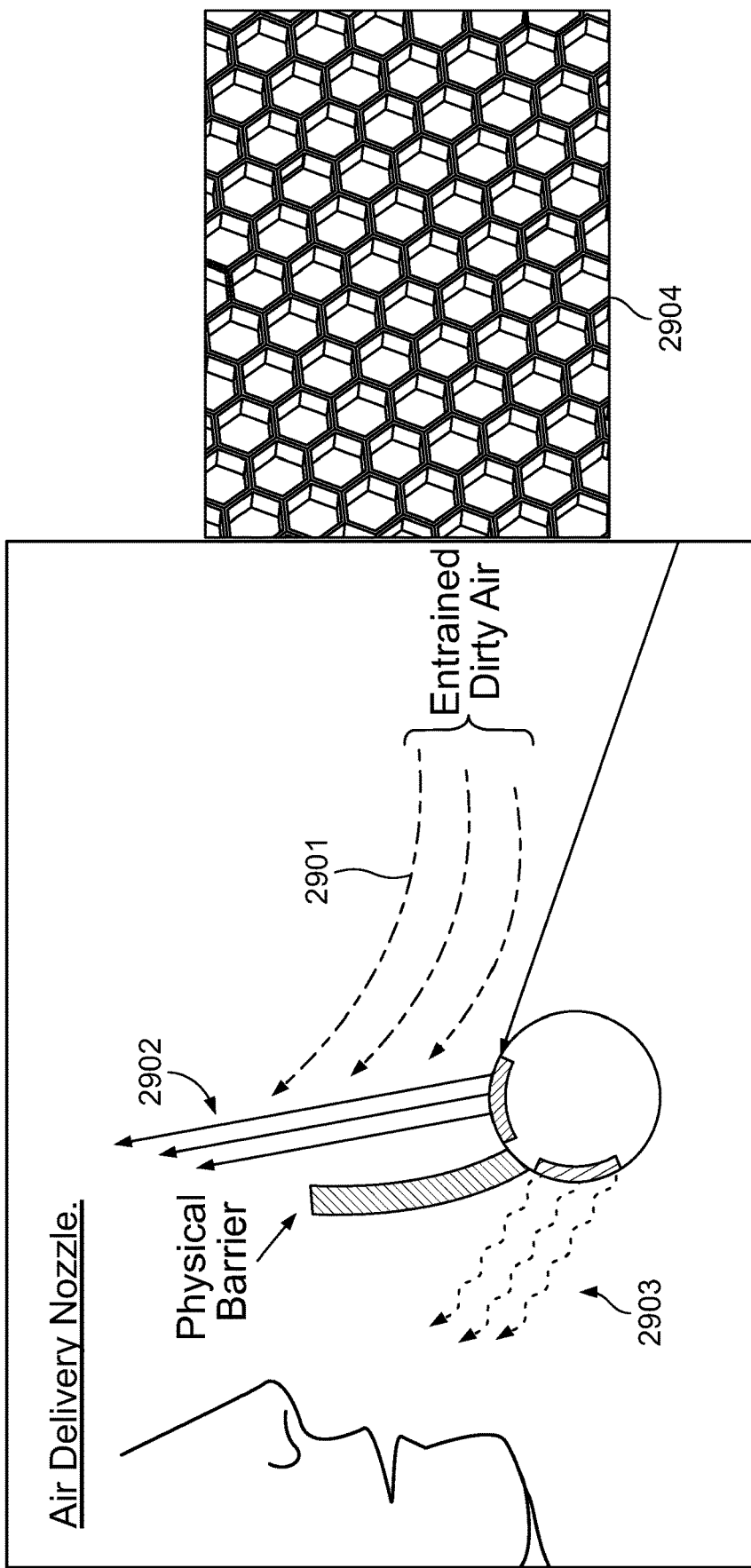
FIG. 29 is an illustration of a two nozzle dispensing design suitable for the present technology.
Figure 30:
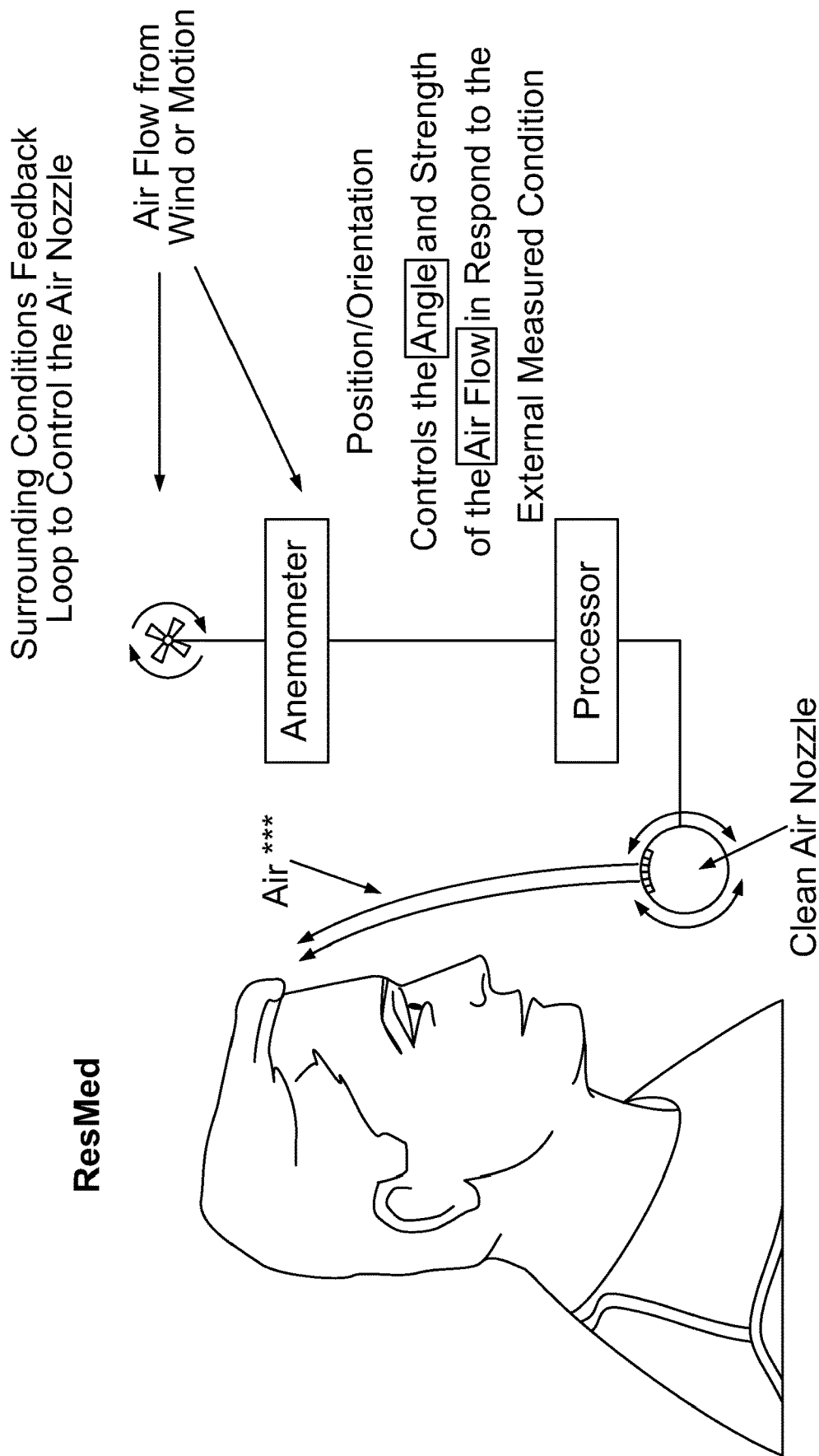
FIG. 30 is an illustration of an anemometer for adjusting airflow position and strength suitable for an embodiment of the present technology.

The user flow interfaces may include nozzles for dispensing the air. These nozzles may include 2 air outputs as shown in FIG. 29. The diagram above shows the 2 nozzle dispensing design. This design solves the problem of entrained dirty air being breathed in by the user. In this system a first nozzle may release a high velocity laminar flow creating an air curtain 2902. This air curtain may entrain the dirty air 2901 and removes it from the pocket of air the user may breathe. The laminar flow can be created by forcing the flow through a laminarising barrier like a honey comb filter 2904. A second nozzle behind the first nozzle may provide a low velocity air, which the user may breathe. As the laminar flow removes all dirty air from in front of the user, the low velocity air is free of undesired particles. Between the two outlets, a small physical barrier may be placed to stop entrainment of the low velocity air into the air curtain.

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A personal portable respiratory apparatus to provide cleaned air to a user, the apparatus comprising:
   a flow generator including a blower, the flow generator configured to generate a filtered or conditioned flow of air;
   a personal spatial respiratory interface coupled to the flow generator, the personal spatial respiratory interface comprising an outlet for the flow generator, the personal spatial respiratory interface configured to direct the flow of air within a breathing proximity of a user;
   a set of filters comprising different types of filters for filtering the flow of air; and
   a controller configured to determine filters in the set of filters for filtering the flow of air based on received data that is associated with aspects of the air in the user's environment,
   wherein the personal portable respiratory apparatus is configured to communicate with a remote smart phone or tablet so that the smart phone or tablet operates to control the flow generator.

2. The personal portable respiratory apparatus of claim 1, wherein the apparatus comprises a smart pollution navigation program configured to monitor a user's location with the smart phone, and configured to provide the user with a notification that the user is nearing or within an area with high pollution.

3. The personal portable respiratory apparatus of claim 1, wherein the apparatus is configured to be controlled with a graphical user interface (GUI) displayed on the smart phone or tablet.

4. The personal portable respiratory apparatus of claim 1, further comprising a communications interface configured to send and receive signals to and from the smart phone or tablet.

5. The personal portable respiratory apparatus of claim 1, wherein the apparatus is configured to provide changes in humidity and temperature to the user.

6. The personal portable respiratory apparatus of claim 1, wherein the apparatus forms a compact blower that is attachable to a user's body.

7. The personal portable respiratory apparatus of claim 1, further comprising one or more sensors configured to detect orientation of the personal spatial respiratory interface.

8. The personal portable respiratory apparatus of claim 1, further comprising a controller coupled to the flow generator, wherein the controller is configured to use GPS to detect a location of the user.

9. The personal portable respiratory apparatus of claim 8, further comprising a GPS sensor.

10. The personal portable respiratory apparatus of claim 8, wherein the controller is configured to access a database of known pollutants in an area of the user using wireless communications based on location data.

11. The personal portable respiratory apparatus of claim 1, wherein the controller is configured to set operation of the set of filters based on the received data.

12. The personal portable respiratory apparatus of claim 1, wherein the set of filters includes a high-efficiency particulate air (HEPA) filter.

13. The personal portable respiratory apparatus of claim 1, wherein the set of filters includes a polarized-media electret filter.

14. The personal portable respiratory apparatus of claim 1, wherein the set of filters includes an ionizer purifier.

15. The personal portable respiratory apparatus of claim 1, wherein the set of filters includes a thermodynamic sterilization filter.

16. The personal portable respiratory apparatus of claim 1, wherein the set of filters includes an activated carbon filter.

17. The personal portable respiratory apparatus of claim 1, wherein the set of filters includes a catalytic oxidation filter.

18. The personal portable respiratory apparatus of claim 1, wherein the set of filters includes two or more of a high-efficiency particulate air (HEPA) filter, an electret filter, an ionizer purifier, a thermodynamic sterilization filter, an activated carbon filter, and a catalytic oxidation filter.

* * * * *

UNITED STATES PATENT AND TRADEMARK OFFICE
CERTIFICATE OF CORRECTION

| | |
|---|---|
| PATENT NO. | : 12,194,322 B2 |
| APPLICATION NO. | : 18/315586 |
| DATED | : January 14, 2025 |
| INVENTOR(S) | : Tzu-Chin Yu et al. |

Page 1 of 1

It is certified that error appears in the above-identified patent and that said Letters Patent is hereby corrected as shown below:

On the Title Page

Item (72), the 9th inventor's name:
Now reads: "Phillip Rodney Kwok"; should read --Philip Rodney Kwok--

Signed and Sealed this
Twenty-fifth Day of March, 2025

Coke Morgan Stewart
*Acting Director of the United States Patent and Trademark Office*